(12) United States Patent
Chen et al.

(10) Patent No.: US 8,227,571 B2
(45) Date of Patent: Jul. 24, 2012

(54) INSULINOTROPIC PEPTIDE SYNTHESIS USING SOLID AND SOLUTION PHASE COMBINATION TECHNIQUES

(75) Inventors: Lin Chen, Superior, CO (US);
Yeun-Kwei Han, Louisville, CO (US);
Christopher R. Roberts, Berthoud, CO (US)

(73) Assignee: Roche Palo Alto LLC, South San Francisco, CA (US)

( * ) Notice: Subject to any disclaimer, the term of this patent is extended or adjusted under 35 U.S.C. 154(b) by 784 days.

(21) Appl. No.: 12/316,309

(22) Filed: Dec. 11, 2008

(65) Prior Publication Data

US 2009/0292108 A1    Nov. 26, 2009

Related U.S. Application Data

(60) Provisional application No. 61/007,238, filed on Dec. 11, 2007.

(51) Int. Cl.
*C07K 14/00*    (2006.01)
(52) U.S. Cl. .......... 530/324; 530/308; 530/338
(58) Field of Classification Search .......... 530/324, 530/308, 338
See application file for complete search history.

(56) References Cited

U.S. PATENT DOCUMENTS

| | | | | |
|---|---|---|---|---|
| 6,903,186 | B1 * | 6/2005 | Dong | 530/324 |
| 2008/0004429 | A1 * | 1/2008 | Roberts et al. | 530/330 |
| 2009/0149628 | A1 * | 6/2009 | King et al. | 530/303 |
| 2009/0292106 | A1 * | 11/2009 | Werbitzky et al. | 530/308 |

OTHER PUBLICATIONS

Wohr, J. Am. Chem. Soc. 118, 9218-9227, 1996.*
Keller, M., J. Am. Chem. Soc. 120, 2714-20, 1998.*
Tam, James P., Journal of the American Chemical Society 121(39), 9013-9022, 1999.*

* cited by examiner

*Primary Examiner* — David Lukton
(74) *Attorney, Agent, or Firm* — Brian L. Buckwalter

(57) ABSTRACT

The present invention relates to the preparation of insulinotropic peptides that are synthesized using a solid and solution phase ("hybrid") approach. Generally, the approach includes synthesizing three different peptide intermediate fragments using solid phase chemistry. Solution phase chemistry is then used to add additional amino acid material to the third fragment which is then coupled to the second fragment and then the first fragment in solution. Alternatively, a different second fragment is coupled to the first fragment in the solid phase. Then, solution phase chemistry is then used to add additional amino acid material to a different third fragment. Subsequently, this different third fragment is coupled to the coupled first and different second fragment in the solution phase. The use of a pseudoproline in one of the fragments eases solid phase synthesis of that fragment and also eases subsequent solution phase coupling of this fragment to the other fragments. The present invention is very useful for forming insulinotropic peptides such as GLP-1(7-36) and its natural and non-natural counterparts.

2 Claims, No Drawings

INSULINOTROPIC PEPTIDE SYNTHESIS USING SOLID AND SOLUTION PHASE COMBINATION TECHNIQUES

CROSS-REFERENCE TO RELATED APPLICATIONS

This application claims the benefit of priority to U.S. Ser. 61/007,238 filed on Dec. 11, 2007, the contents of which are hereby incorporated in their entirety by reference.

FIELD OF THE INVENTION

The invention relates to methods for preparing insulinotropic peptides, particularly glucagon-like peptide-1 (GLP-1) and counterparts thereof, using solid- and solution-phase processes. The present invention further relates to intermediate peptide fragments that can be used in these methods.

BACKGROUND OF THE INVENTION

Many methods for peptide synthesis are described in the literature (for example, see U.S. Pat. No. 6,015,881; Mergler et al. (1988) Tetrahedron Letters 29:4005-4008; Mergler et al. (1988) Tetrahedron Letters 29:4009-4012; Kamber et al. (eds), Peptides, Chemistry and Biology, ESCOM, Leiden (1992) 525-526; Riniker et al. (1993) Tetrahedron Letters 49:9307-9320; Lloyd-Williams et al. (1993) Tetrahedron Letters 49:11065-11133; and Andersson et al. (2000) Biopolymers 55:227-250. The various methods of synthesis are distinguished by the physical state of the phase in which the synthesis takes place, namely liquid phase or solid phase.

In solid phase peptide synthesis (SPPS), an amino acid or peptide group is bound to a solid support resin. Then, successive amino acids or peptide groups are attached to the support-bound peptide until the peptide material of interest is formed. The support-bound peptide is then typically cleaved from the support and subject to further processing and/or purification. In some cases, solid phase synthesis yields a mature peptide product; in other cases the peptide cleaved from the support (i.e., a "peptide intermediate fragment") is used in the preparation of a larger, mature peptide product.

Peptide intermediate fragments generated from solid phase processes can be coupled together in the solid phase or in a liquid phase synthetic process (herein referred to as "solution phase synthesis"). Solution phase synthesis can be particularly useful in cases where the synthesis of a useful mature peptide by solid phase is either impossible or not practical. For example, in solid phase synthesis, longer peptides eventually may adopt an irregular conformation while still attached to the solid support, making it difficult to add additional amino acids or peptide material to the growing chain. As the peptide chain becomes longer on the support resin, the efficiency of process steps such as coupling and deprotection may be compromised. This, in turn, can result in longer processing times to compensate for these problems, in addition to incremental losses in starting materials, such as activatable amino acids, co-reagents, and solvents. These problems can increase as the length of the peptide increases.

Therefore, it is relatively uncommon to find mature peptides of greater than 30 amino acids in length synthesized in a single fragment using only a solid phase procedure. Instead, individual fragments may be separately synthesized on the solid phase, and then coupled in the solid and/or solution phase to build the desired peptide product. This approach requires careful selection of fragment candidates. While some general principles can guide fragment selection, quite often empirical testing of fragment candidates is required. Fragment strategies that work in one context may not work in others. Even when reasonable fragment candidates are uncovered, process innovations may still be needed for a synthesis strategy to work under commercially reasonable conditions. Therefore, peptide synthesis using hybrid schemes are often challenging, and in many cases it is difficult to predict what problems are inherent in a synthesis scheme until the actual synthesis is performed.

In solution phase coupling, two peptide intermediate fragments, or a peptide intermediate fragment and a reactive amino acid, are coupled in an appropriate solvent, usually in the presence of additional reagents that promote the efficiency and quality of the coupling reaction. The peptide intermediate fragments are reactively arranged so the N-terminal of one fragment becomes coupled to the C-terminal of the other fragment, or vice versa. In addition, side chain protecting groups, which are present during solid phase synthesis, are commonly retained on the fragments during solution phase coupling to ensure the specific reactivity of the terminal ends of the fragments. These side chain protecting groups are typically not removed until a mature peptide has been formed.

Modest improvements in one or more steps in the overall synthetic scheme can amount to significant improvements in the preparation of the mature peptide. Such improvements can lead to a large overall saving in time and reagents, and can also significantly improve the purity and yield of the final product.

While the discussion of the importance of improvements in hybrid synthesis is applicable to any sort of peptide produced using these procedures, it is of particular import in the context of peptides that are therapeutically useful and that are manufactured on a scale for commercial medical use. Synthesis of larger biomolecular pharmaceuticals, such as therapeutic peptides, can be very expensive. Because of the cost of reagents, synthesis time, many synthesis steps, in addition to other factors, very small improvements in the synthetic process of these larger biomolecular pharmaceuticals can have a significant impact on whether it is even economically feasible to produce such a pharmaceutical. Such improvements are necessary due to these high production costs for larger biomolecular pharmaceuticals as supported by the fact that, in many cases, there are few, if any, suitable therapeutic alternatives for these types of larger biomolecular pharmaceuticals.

This is clearly seen in the case of the glucagon-like peptide-1 (GLP-1) and its counterparts. These peptides have been implicated as possible therapeutic agents for the treatment of type 2 non-insulin-dependent diabetes mellitus as well as related metabolic disorders, such as obesity. Gutniak, M. K., et al., Diabetes Care 1994:17:1039-44.

Lopez et al. determined that native GLP-1 was 37 amino acid residues long. Lopez, L. C., et al., *Proc. Natl. Acad. Sci. USA.*, 80:5485-5489 (1983). This determination was confirmed by the work of Uttenthal, L. O., et al., J. Clin. Endocrinal. Metabol., 61:472-479 (1985). Native GLP-1 may be represented by the notation GLP-1 (1-37). This notation indicates that the peptide has all amino acids from 1 (N-terminus) through 37 (C-terminus). Native GLP-1 (1-37) has the amino acid sequence according to SEQ ID NO. 1:

HDEFERHAEGTFTSDVSSYLEGQAAKEFIAWLVKGRG

It has been reported that native GLP-1 (1-37) is generally unable to mediate insulin biosynthesis, but biologically important fragments of this peptide do have insulinotropic properties. For example, the native 31-amino acid long peptide GLP-1 (7-37) according to SEQ ID NO. 2

HAEGTFTSDVSSYLEGQAAKEFIAWLVKGRG is insulinotropic and has the amino acids from the 7 (N-terminus) to the 37 (C-terminus) position of native GLP-1. GLP-1 (7-37) has a terminal glycine. When this glycine is absent, the resultant peptide is still insulinotropically active and is referred to as GLP-1 (7-36) according to SEQ ID NO. 3:

HAEGTFTSDVSSYLEGQAAKEFIAWLVKGR

GLP-1 (7-36) often exists with the C-terminal arginine in amidated form, and this form may be represented by the notation GLP-1 (7-36)-$NH_2$.

GLP-1 (1-37) generally is converted into an insulinotropically active counterpart thereof in vivo. For instance, GLP-1 (1-37) is naturally converted to GLP-1 (7-37) in vivo. This peptide, in turn, can also undergo additional processing by proteolytic removal of the C-terminal glycine to produce GLP-1 (7-36), which often exists in the amidated form GLP-1(7-36)-$NH_2$. Accordingly, therapeutic treatments may involve administration of GLP-1 (1-37) or a counterpart thereof, with the expectation that an insulinotropically active derivative thereof forms in vivo. More commonly, however, therapeutic treatments under investigation involve administration of the insulinotropically active GLP-1 fragments themselves.

According to U.S. Pat. No. 6,887,849, the insulinotropic activity of GLP-1(7-37), GLP-1(7-36) and GLP-1(7-36)-$NH_2$ appears to be specific for the pancreatic beta cells, where these peptides appear to induce biosynthesis of insulin. This makes these peptides and pharmaceutically acceptable counterparts thereof useful in the study of the pathogenesis of adult onset diabetes mellitus, a condition characterized by hyperglycemia in which the dynamics of insulin secretion are abnormal. Moreover, these glucagon-like peptides would be useful in the therapy and treatment of this disease, and in the therapy and treatment of hyperglycemia. According to EP 1137667 B1, these peptides or pharmaceutically acceptable counterparts thereof may also be useful for treating other types of diabetes, obesity, glucagonomas, secretory disorders of the airway, metabolic disorder, arthritis, osteoporosis, central nervous system disease, restenosis, neurodegenerative disease, renal failure, congestive heart failure, neophrotic syndrome, cirrhosis, pulmonary edema, hypertension, and/or disorders where a reduction in food intake is desired.

Native GLP-1 (1-37) and the native, insulinotropically active counterparts thereof according to SEQ ID NO. 1 through 3 are metabolically unstable, having a plasma half-life of only 1 to 2 minutes in vivo. Exogenously administered GLP-1 also is rapidly degraded. This metabolic instability has limited the therapeutic potential of native GLP-1 and native fragments thereof.

Synthetic counterparts of the GLP-1 peptides with improved stability have been developed. For instance, the peptide according to SEQ ID NO. 4 is described in EP 1137667 B1:

HAibEGTFTSDVSSYLEGQAAKEFIAWLVKAibR

This peptide is similar to the native GLP-1 (7-36), except that the achiral residue of alpha-aminoisobutyric acid (shown schematically by the abbreviation Aib) appears at the 8 and 35 positions in place of the corresponding native amino acids at these positions. The achiral alpha-aminoisobutric acid also is known as methylalanine. This peptide may be designated by the formula $(Aib^{8,35})$GLP-1 (7-36) or, in amidated form, $(Aib^{8,35})$GLP-1 (7-36)-$NH_2$.

EP 1137667 B1 states that the peptide according to SEQ ID NO. 4 and its counterparts can be built as a single fragment using solid phase techniques. The single fragment synthesis approach suggested by EP 1137667 B1 is problematic. As one issue, this approach may lead to high levels of epimerization in the final amino acid coupling, e.g., histidine in the case of $(Aib^{8,35})$GLP-1 (7-36) for instance. Additionally, impurities may be hard to remove during chromatographic purification, and the yield may tend to be too low. Consequently, improved strategies for synthesizing peptides according to SEQ ID NO. 4 are needed in order to be able to manufacture this peptide and counterparts thereof in commercially acceptable yields, purities, and quantities.

In addition to these concerns, issues relating to product recovery and product purity for the large-scale production of peptides, as well as reagent handling, storage and disposal, can greatly impact the feasibility of the peptide synthesis scheme. Thus, there is a continuing need for peptide synthesis processes capable of efficiently producing peptide materials of commercial interest in large batch quantities with improved yields.

SUMMARY OF THE INVENTION

The present application relates to the preparation of insulinotropic peptides that are synthesized using a solid and solution phase ("hybrid") approach. In one method, the approach includes synthesizing three different peptide intermediate fragments using solid phase chemistry. Solution phase chemistry is then used to add additional amino acid material to one of the fragments. The fragments are then coupled together in the solution phase. The use of a pseudoproline in one of the fragments eases the solid phase synthesis of that fragment and also eases the subsequent solution phase coupling of this fragment to other fragments. The present invention is very useful for forming insulinotropic peptides such as GLP-1, GLP-1 (7-36) and natural and non-natural counterparts of these, particularly GLP-1 (7-36) and its natural and non-natural counterparts.

In one aspect, the application provides a method of making an insulinotropic peptide, comprising the steps of:
a) providing a first peptide fragment including the amino acid sequence of (SEQ ID NO. 5)

Z-QAAKEFIAWLVKX$^{35}$-B' wherein
$X^{35}$ is an achiral, optionally sterically hindered amino acid residue;
Z is an N-terminal protecting group;
B' is —OH; and
one or more residues of said sequence optionally includes side chain protection;
b) coupling the first peptide fragment in solution to arginine amide in order to provide a second peptide fragment including the amino acid sequence of (SEQ ID NO. 6)

Z-QAAKEFIAWLVKX$^{35}$R-NH$_2$ wherein

Z is an N-terminal protecting group;

$X^{35}$ is an achiral, optionally sterically hindered amino acid residue; and one or more residues of said sequence optionally includes side chain protection;

c) removing the N-terminal protecting group to afford a third peptide fragment including the amino acid sequence of (SEQ ID NO. 6)

Z-QAAKEFIAWLVKX³⁵R-NH₂ wherein

Z is H—;

$X^{35}$ is an achiral, optionally sterically hindered amino acid residue; and one or more residues of said sequence optionally includes side chain protection;

d) providing a fourth peptide fragment including the amino acid sequence of (SEQ ID NO. 7)

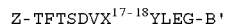
Z-TFTSDVX¹⁷⁻¹⁸YLEG-B' wherein $X^{17-18}$ is a dipeptide residue of a pseudoproline;

Z is an N-terminal protecting group;

B' is —OH; and one or more residues of said sequence optionally includes side chain protection;

e) coupling the fourth peptide fragment to the third peptide fragment in solution in order to provide a fifth peptide fragment including the amino acid sequence of (SEQ ID NO. 8)

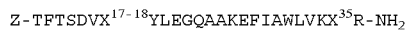
Z-TFTSDVX¹⁷⁻¹⁸YLEGQAAKEFIAWLVKX³⁵R-NH₂ wherein

Z is an N-terminal protecting group;

$X^{17-18}$ is a dipeptide residue of a pseudoproline;

$X^{35}$ is an achiral, optionally sterically hindered amino acid residue; and one or more residues of said sequence optionally includes side chain protection;

f) removing the N-terminal protecting group to afford a sixth peptide fragment including the amino acid sequence of (SEQ ID NO. 8)

Z-TFTSDVX¹⁷⁻¹⁸YLEGQAAKEFIAWLVKX³⁵R-NH₂ wherein

Z is H—;

$X^{17-18}$ is a dipeptide residue of a pseudoproline;

$X^{35}$ is an achiral, optionally sterically hindered amino acid residue; and one or more residues of said sequence optionally includes side chain protection;

g) providing a seventh peptide fragment including the amino acid sequence of (SEQ ID NO. 9)

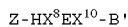
Z-HX⁸EX¹⁰-B' wherein $X^8$ and $X^{10}$ are each independently achiral, optionally sterically hindered amino acid residues;

Z is an N-terminal protecting group;

B' is —OH; and each of H and E optionally includes side chain protection; and h) coupling the seventh peptide fragment to the sixth peptide fragment in solution to provide an insulinotropic peptide including the amino acid sequence of (SEQ ID NO. 10)

Z-HX⁸EX¹⁰TFTSDVX¹⁷⁻¹⁸YLEGQAAKEFIAWLVKX³⁵R-NH₂ wherein

Z is an N-terminal protecting group;

$X^{17-18}$ is a dipeptide residue of a pseudoproline;

$X^8$, $X^{10}$ and $X^{35}$ are each independently achiral, optionally sterically hindered amino acid residues; and one or more residues of said sequence optionally includes side chain protection.

In another aspect, the application provides the above method, further comprising the steps of:

i) removing the N-terminal protecting group of the insulinotropic peptide to afford the insulinotropic peptide including amino acid sequence of (SEQ ID NO. 10)

Z-HX⁸EX¹⁰TFTSDVX¹⁷⁻¹⁸YLEGQAAKEFIAWLVKX³⁵R-NH₂ wherein

Z is H—;

$X^{17-18}$ is a dipeptide residue of a pseudoproline;

$X^{35}$ $X^8$, $X^{10}$ and $X^{35}$ are each independently achiral, optionally sterically hindered amino acid residues; and one or more residues of said sequence optionally includes side chain protection; and j) contacting the insulinotropic peptide resulting from step i) with acid in order to deprotect the amino acid side chains to afford the deprotected insulinotropic peptide including amino acid sequence of (SEQ ID NO. 11)

Z-HX⁸EX¹⁰TFTSDVSSYLEGQAAKEFIAWLVKX³⁵R-NH₂ wherein

Z is H—; and $X^8$, $X^{10}$ and $X^{35}$ are each independently achiral, optionally sterically hindered amino acid residues.

In yet another aspect, the application provides the above method, wherein the deprotected insulinotropic peptide has the amino acid sequence (SEQ. ID No. 12)

HAibEGTFTSDVSSYLEGQAAKEFIAWLVKAibR

In one aspect, the application provides a method of making an insulinotropic peptide, comprising the steps of:

a) providing a first peptide fragment including the amino acid sequence of (SEQ ID NO. 5)

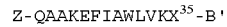
Z-QAAKEFIAWLVKX³⁵-B' wherein $X^{35}$ is an achiral, optionally sterically hindered amino acid residue;

Z is an N-terminal protecting group;

B' is a solid phase resin; and one or more residues of said sequence optionally includes side chain protection;

b) removing the N-terminal protecting group to afford a second peptide fragment including the amino acid sequence of (SEQ ID NO. 5)

$$Z\text{-QAAKEFIAWLVKX}^{35}\text{-B'}$$

wherein
Z is H—;
B' is a solid phase resin;
$X^{35}$ is an achiral, optionally sterically hindered amino acid residue; and
one or more residues of said sequence optionally includes side chain protection;
c) providing a third peptide fragment in solution including the amino acid sequence of (SEQ ID NO. 7)

$$Z\text{-TFTSDVX}^{17\text{-}18}\text{YLEG-B'}$$

wherein
$X^{17\text{-}18}$ is a dipeptide residue of a pseudoproline;
Z is an N-terminal protecting group;
B' is —OH; and
one or more residues of said sequence optionally includes side chain protection;
d) coupling the third peptide fragment in solution to the second peptide fragment in solid phase in order to provide a fourth peptide fragment including the amino acid sequence of (SEQ ID NO. 13)

$$Z\text{-TFTSDVX}^{17\text{-}18}\text{YLEGQAAKEFIAWLVKX}^{35}\text{-B'}$$

wherein
Z is an N-terminal protecting group;
B' is a solid phase resin;
$X^{17\text{-}18}$ is a dipeptide residue of a pseudoproline;
$X^{35}$ is an achiral, optionally sterically hindered amino acid residue; and
one or more residues of said sequence optionally includes side chain protection;
e) removing the fourth peptide fragment from the solid phase resin and coupling the fourth peptide fragment in solution to arginine amide in order to provide a fifth peptide fragment including the amino acid sequence of (SEQ ID NO. 8)

$$Z\text{-TFTSDVX}^{17\text{-}18}\text{YLEGQAAKEFIAWLVKX}^{35}\text{R-NH}_2$$

wherein
Z is an N-terminal protecting group;
$X^{17\text{-}18}$ is a dipeptide residue of a pseudoproline;
$X^{35}$ is an achiral, optionally sterically hindered amino acid residue; and
one or more residues of said sequence optionally includes side chain protection;
f) removing the N-terminal protecting group to afford a sixth peptide fragment including the amino acid sequence of (SEQ ID NO. 8)

$$Z\text{-TFTSDVX}^{17\text{-}18}\text{YLEGQAAKEFIAWLVKX}^{35}\text{R-NH}_2$$

wherein
Z is H—;
$X^{17\text{-}18}$ is a dipeptide residue of a pseudoproline;
$X^{35}$ is an achiral, optionally sterically hindered amino acid residue; and one or more residues of said sequence optionally includes side chain protection;
g) providing a seventh peptide fragment including the amino acid sequence of (SEQ ID NO. 9)

$$Z\text{-HX}^8\text{EX}^{10}\text{-B'}$$

wherein
$X^8$ and $X^{10}$ are each independently achiral, optionally sterically hindered amino acid residues;
Z is an N-terminal protecting group;
B' is —OH; and
each of H and E optionally includes side chain protection; and
h) coupling the seventh peptide fragment to the sixth peptide fragment in solution to provide an insulinotropic peptide including the amino acid sequence of (SEQ ID NO. 10)

$$Z\text{-HX}^8\text{EX}^{10}\text{TFTSDVX}^{17\text{-}18}\text{YLEGQAAKEFIAWLVKX}^{35}\text{R-NH}_2$$

wherein
Z is an N-terminal protecting group;
$X^{17\text{-}18}$ is a dipeptide residue of a pseudoproline;
$X^8$, $X^{10}$ and $X^{35}$ are each independently achiral, optionally sterically hindered amino acid residues; and
one or more residues of said sequence optionally includes side chain protection.

In another aspect, the application provides the above method, further comprising the steps of:
i) removing the N-terminal protecting group of the insulinotropic peptide to afford the insulinotropic peptide including amino acid sequence of (SEQ ID NO. 10)

$$Z\text{-HX}^8\text{EX}^{10}\text{TFTSDVX}^{17\text{-}18}\text{YLEGQAAKEFIAWLVKX}^{35}\text{R-NH}_2$$

wherein
Z is H—;
$X^{17\text{-}18}$ is a dipeptide residue of a pseudoproline;
$X^{35}$ $X^8$, $X^{10}$ and $X^{35}$ are each independently achiral, optionally sterically hindered amino acid residues; and
one or more residues of said sequence optionally includes side chain protection; and
j) contacting the insulinotropic peptide resulting from step i) with acid to deprotect the amino acid side chains to afford the deprotected insulinotropic peptide including amino acid sequence of (SEQ ID NO. 11)

$$Z\text{-HX}^8\text{EX}^{10}\text{TFTSDVSSYLEGQAAKEFIAWLVKX}^{35}\text{R-NH}_2$$

wherein
Z is H—; and
$X^8$, $X^{10}$ and $X^{35}$ are each independently achiral, optionally sterically hindered amino acid residues.

In yet another aspect, the application provides the above method, wherein the deprotected insulinotropic peptide has the amino acid sequence (SEQ. ID No. 12)

$$\text{HAibEGTFTSDVSSYLEGQAAKEFIAWLVKAibR-NH}_2$$

In one aspect, the application provides a method of making an insulinotropic peptide, comprising the steps of:
a) providing a first peptide fragment or counterpart thereof including the amino acid sequence of (SEQ ID NO. 13)

wherein
Z is an N-terminal protecting group;
B' is —OH;
X$^{17-18}$ is a dipeptide residue of a pseudoproline;
X$^{35}$ is an achiral, optionally sterically hindered amino acid residue; and
one or more residues of said sequence optionally include side chain protection;
b) coupling the first peptide fragment in solution to arginine amide in order to provide a second peptide fragment including the amino acid sequence of (SEQ ID NO. 8)

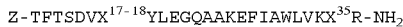

wherein
Z is an N-terminal protecting group;
X$^{17-18}$ is a dipeptide residue of a pseudoproline;
X$^{35}$ is an achiral, optionally sterically hindered amino acid residue; and
one or more residues of said sequence optionally includes side chain protection;
c) removing the N-terminal protecting group to afford a third peptide fragment including the amino acid sequence of (SEQ ID NO. 8)

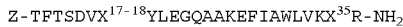

wherein
Z is H—;
X$^{17-18}$ is a dipeptide residue of a pseudoproline;
X$^{35}$ is an achiral, optionally sterically hindered amino acid residue; and
one or more residues of said sequence optionally includes side chain protection;
d) providing a fourth peptide fragment including the amino acid sequence of (SEQ ID NO. 9)

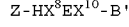

wherein
X$^8$ and X$^{10}$ are each independently achiral, optionally sterically hindered amino acid residues;
Z is an N-terminal protecting group;
B' is —OH; and
each of H and E optionally includes side chain protection; and
e) coupling the fourth peptide fragment to the third peptide fragment in solution to provide an insulinotropic peptide including the amino acid sequence of (SEQ ID NO. 10)

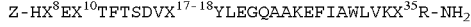

wherein
Z is an N-terminal protecting group;
X$^{10-18}$ is a dipeptide residue of a pseudoproline;
X$^8$, X$^{10}$ and X$^{35}$ are each independently achiral, optionally sterically hindered amino acid residues; and one or more residues of said sequence optionally includes side chain protection.

In another aspect, the application provides the above method, further comprising the steps of:
i) removing the N-terminal protecting group of the insulinotropic peptide to afford the insulinotropic peptide including amino acid sequence of (SEQ ID NO. 10)

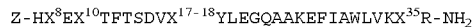

wherein
Z is H—;
X$^{17-18}$ is a dipeptide residue of a pseudoproline;
X$^{35}$ X$^8$, X$^{10}$ and X$^{35}$ are each independently achiral, optionally sterically hindered amino acid residues; and
one or more residues of said sequence optionally includes side chain protection; and
j) contacting the insulinotropic peptide resulting from step i) with acid to deprotect the amino acid side chains to afford the deprotected insulinotropic peptide including amino acid sequence of (SEQ ID NO. 11)

wherein
Z is H—; and
X$^8$, X$^{10}$ and X$^{35}$ are each independently achiral, optionally sterically hindered amino acid residues.

In yet another aspect, the application provides the above method, wherein the deprotected insulinotropic peptide has the amino acid sequence (SEQ. ID No. 12)

In one aspect, any of the above methods may employ N-terminus histidine protecting groups selected from the group consisting of Boc, CBz, DTS, Rdtc (R=Alkyl or Aryl), DBFmoc (2,7-di-t-butylFmoc), Alloc, pNZ (p-nitrobenzyl ester), Nsc ([[2-[(4-nitrophenyl)sulfonyl]ethoxy]carbonyl]-), Msc (2-methylsulfonylethoxycarbonyl), MBz (4-methoxy-CBz), [(1-[1,1'-biphenyl]-4-yl-1-methylethoxy)carbonyl], [[2,2-bis(4-nitrophenyl)ethoxy]carbonyl], [(phenylmethoxy)carbonyl], [(1,1-dimethylpropoxy)carbonyl], and [[(4-methoxyphenyl)methoxy]carbonyl], wherein if the N-terminus histidine protecting group may be removed in the global side-chain deprotection step using acid, prior removal of the N-terminus histidine protecting group is not required.

In one aspect, the application provides a peptide of the amino acid sequence (SEQ. ID NO. 14)

wherein
Z is selected from H— and Fmoc-;
B' is —OH or solid phase resin;
X$^{17-18}$ is a dipeptide residue of a pseudoproline; and
one or more residues of said sequence optionally include side chain protection.

In another aspect, the application provides the above peptide, wherein the dipeptide residue of a pseudoproline is a Ser-Ser residue of a pseudoproline.

In one aspect, the application provides a peptide of the amino acid sequence (SEQ. ID NO. 15)

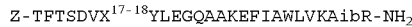
Z-TFTSDVX$^{17-18}$YLEGQAAKEFIAWLVKAibR-NH$_2$ wherein

Z is selected from H— and Fmoc-;

X$^{17-18}$ is a dipeptide residue of a pseudoproline; and one or more residues of said sequence optionally include side chain protection.

In another aspect, the application provides the above peptide, wherein the dipeptide residue of a pseudoproline is a Ser-Ser residue of a pseudoproline.

The present application relates to the preparation of insulinotropic peptides that are synthesized using a solid and solution phase ("hybrid") approach. Generally, the approach includes synthesizing three different peptide intermediate fragments using solid phase chemistry. Solution phase chemistry is then used to add additional amino acid material to one of the fragments. The fragments are then coupled together in the solution phase. The use of a pseudoproline in one of the fragments eases the solid phase synthesis of that fragment and also eases the subsequent solution phase coupling of this fragment to other fragments. The present invention is very useful for forming insulinotropic peptides such as GLP-1, GLP-1(7-36) and natural and non-natural counterparts of these, particularly GLP-1(7-36) and its natural and non-natural counterparts.

In one aspect, the application provides a method of making an insulinotropic peptide, comprising the steps of:

a) providing a first peptide fragment including the amino acid sequence of (SEQ ID NO. 16)

Z-FIAWLVKX$^{35}$-B' wherein

X$^{35}$ is an achiral, optionally sterically hindered amino acid residue;

Z is an N-terminal protecting group Fmoc-;

B' is a solid phase resin; and one or more residues of said sequence optionally includes side chain protection;

b) cleaving the first peptide fragment of step a) from the solid phase resin to yield the first peptide fragment in solution (SEQ ID NO. 16)

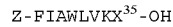
Z-FIAWLVKX$^{35}$-OH c) coupling the first peptide fragment in solution to arginine amide in order to provide a second peptide fragment including the amino acid sequence of (SEQ ID NO. 17)

Z-FIAWLVKX$^{35}$R-NH$_2$ wherein

Z is an N-terminal protecting group;

X$^{35}$ is an achiral, optionally sterically hindered amino acid residue; and one or more residues of said sequence optionally includes side chain protection;

d) removing the N-terminal protecting group to afford a third peptide fragment including the amino acid sequence of (SEQ ID NO. 17)

Z-FIAWLVKX$^{35}$R-NH$_2$ wherein

Z is H—;

X$^{35}$ is an achiral, optionally sterically hindered amino acid residue; and one or more residues of said sequence optionally includes side chain protection.

In one aspect, the application provides a peptide prepared according to the above method having the amino acid sequence (SEQ ID NO. 17)

Z-FIAWLVKX$^{35}$R-NH$_2$ wherein

Z is an N-terminal protecting group; and

X$^{35}$ is an achiral, optionally sterically hindered amino acid residue; and one or more residues of said sequence optionally includes side chain protection.

In one variation of the above peptide, X$^{35}$ is Aib.

In one aspect, the application provides a peptide prepared according to the above method having the amino acid sequence (SEQ ID NO. 16)

Z-FIAWLVKX$^{35}$-B' wherein

B' is solid phase resin or —OH;

Z is an N-terminal protecting group; and

X$^{35}$ is an achiral, optionally sterically hindered amino acid residue; and one or more residues of said sequence optionally includes side chain protection.

In one variation of the above peptide, X$^{35}$ is Aib.

In one aspect, the application provides a method of making an insulinotropic peptide, comprising the steps of:

a) providing a peptide fragment including the amino acid sequence of (SEQ ID NO. 18)

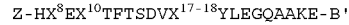
Z-HX$^8$EX$^{10}$TFTSDVX$^{17-18}$YLEGQAAKE-B' wherein

X$^8$ and X$^{10}$ are each independently achiral, optionally sterically hindered amino acid residues;

X$^{17-18}$ is a dipeptide residue of a pseudoproline;

Z is an N-terminal protecting group;

B' is a solid phase resin; and one or more residues of said sequence optionally includes side chain protection; and b) cleaving the peptide fragment of step a) from the solid phase resin to yield the peptide fragment in solution (SEQ ID NO. 18)

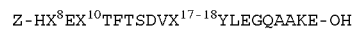
Z-HX$^8$EX$^{10}$TFTSDVX$^{17-18}$YLEGQAAKE-OH

In one aspect, the application provides a method comprising the steps of:

a) providing a first peptide fragment including the amino acid sequence of (SEQ ID NO. 16)

$$Z\text{-FIAWLVKX}^{35}\text{-B'}$$

wherein
$X^{35}$ is an achiral, optionally sterically hindered amino acid residue;
Z is an N-terminal protecting group Fmoc-;
B' is a solid phase resin; and
one or more residues of said sequence optionally includes side chain protection;

b) cleaving the first peptide fragment of step a) from the solid phase resin to yield the first peptide fragment in solution (SEQ ID NO. 16)

$$Z\text{-FIAWLVKX}^{35}\text{-OH}$$

c) coupling the first peptide fragment in solution to arginine amide in order to provide a second peptide fragment including the amino acid sequence of (SEQ ID NO. 17)

$$Z\text{-FIAWLVKX}^{35}\text{R-NH}_2$$

wherein
Z is an N-terminal protecting group;
$X^{35}$ is an achiral, optionally sterically hindered amino acid residue; and
one or more residues of said sequence optionally includes side chain protection;

d) removing the N-terminal protecting group to afford a third peptide fragment including the amino acid sequence of (SEQ ID NO. 17)

$$Z\text{-FIAWLVKX}^{35}\text{R-NH}_2$$

wherein
Z is H—;
$X^{35}$ is an achiral, optionally sterically hindered amino acid residue; and
one or more residues of said sequence optionally includes side chain protection; and e) providing a fourth peptide fragment including the amino acid sequence of (SEQ ID NO. 18)

$$Z\text{-HX}^8\text{EX}^{10}\text{TFTSDVX}^{17\text{-}18}\text{YLEGQAAKE-B'}$$

wherein
$X^8$ and $X^{10}$ are each independently achiral, optionally sterically hindered amino acid residues;
$X^{17\text{-}18}$ is a dipeptide residue of a pseudoproline;
Z is an N-terminal protecting group;
B' is a solid phase resin; and
one or more residues of said sequence optionally includes side chain protection; and f) cleaving the fourth peptide fragment of step e) from the solid phase resin to yield the fourth peptide fragment in solution (SEQ ID NO. 18)

$$Z\text{-HX}^8\text{EX}^{10}\text{TFTSDVX}^{17\text{-}18}\text{YLEGQAAKE-OH}$$

In one aspect, the application provides a method of making an insulinotropic peptide, comprising the step of:

a) coupling a first peptide fragment to a second peptide fragment in solution in order to provide a third peptide fragment including the amino acid sequence of (SEQ ID NO. 26)

$$Z\text{-HX}^8\text{EX}^{10}\text{TFTSDVX}^{17\text{-}18}\text{YLEGQAAKEFIAWLVKX}^{35}\text{R-NH}_2$$

wherein
Z is an N-terminal protecting group;
$X^8$ and $X^{10}$ are each independently achiral, optionally sterically hindered amino acid residues;
$X^{17\text{-}18}$ is a dipeptide residue of a pseudoproline;
$X^{35}$ is an achiral, optionally sterically hindered amino acid residue; and
one or more residues of said sequence optionally includes side chain protection.

In one aspect, the application provides a method comprising the step of:

a) providing a first peptide fragment including the amino acid sequence of (SEQ ID NO. 16)

$$Z\text{-FIAWLVKX}^{35}\text{-B'}$$

wherein
$X^{35}$ is an achiral, optionally sterically hindered amino acid residue;
Z is an N-terminal protecting group Fmoc-;
B' is a solid phase resin; and
one or more residues of said sequence optionally includes side chain protection;

b) cleaving the first peptide fragment of step a) from the solid phase resin to yield the first peptide fragment in solution (SEQ ID NO. 16)

$$Z\text{-FIAWLVKX}^{35}\text{-OH}$$

c) coupling the first peptide fragment in solution to arginine amide in order to provide a second peptide fragment including the amino acid sequence of (SEQ ID NO. 17)

$$Z\text{-FIAWLVKX}^{35}\text{R-NH}_2$$

wherein
Z is an N-terminal protecting group;
$X^{35}$ is an achiral, optionally sterically hindered amino acid residue; and
one or more residues of said sequence optionally includes side chain protection;

d) removing the N-terminal protecting group to afford a third peptide fragment including the amino acid sequence of (SEQ ID NO. 17)

$$Z\text{-FIAWLVKX}^{35}\text{R-NH}_2$$

wherein
Z is H—;
$X^{35}$ is an achiral, optionally sterically hindered amino acid residue; and
one or more residues of said sequence optionally includes side chain protection; and e) providing a fourth peptide fragment including the amino acid sequence of (SEQ ID NO. 18)

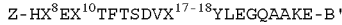

wherein
$X^8$ and $X^{10}$ are each independently achiral, optionally sterically hindered amino acid residues;
$X^{17-18}$ is a dipeptide residue of a pseudoproline;
Z is an N-terminal protecting group;
B' is a solid phase resin; and
one or more residues of said sequence optionally includes side chain protection; and f) cleaving the fourth peptide fragment of step e) from the solid phase resin to yield the fourth peptide fragment in solution (SEQ ID NO. 18)

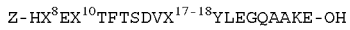

g) coupling the fourth peptide fragment to the third peptide fragment in solution in order to provide a fifth peptide fragment including the amino acid sequence of (SEQ ID NO. 26)

wherein
Z is an N-terminal protecting group;
$X^8$ and $X^{10}$ are each independently achiral, optionally sterically hindered amino acid residues;
$X^{17-18}$ is a dipeptide residue of a pseudoproline;
$X^{35}$ is an achiral, optionally sterically hindered amino acid residue; and
one or more residues of said sequence optionally includes side chain protection.

In one aspect, the application provides a method comprising the step of:

a) providing a first peptide fragment including the amino acid sequence of (SEQ ID NO. 16)

wherein
$X^{35}$ is an achiral, optionally sterically hindered amino acid residue;
Z is an N-terminal protecting group Fmoc-;
B' is a solid phase resin; and
one or more residues of said sequence optionally includes side chain protection;

b) cleaving the first peptide fragment of step a) from the solid phase resin to yield the first peptide fragment in solution (SEQ ID NO. 16)

c) coupling the first peptide fragment in solution to arginine amide in order to provide a second peptide fragment including the amino acid sequence of (SEQ ID NO. 17)

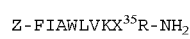

wherein
Z is an N-terminal protecting group;
$X^{35}$ is an achiral, optionally sterically hindered amino acid residue; and
one or more residues of said sequence optionally includes side chain protection;

d) removing the N-terminal protecting group to afford a third peptide fragment including the amino acid sequence of (SEQ ID NO. 17)

wherein
Z is H—;
$X^{35}$ is an achiral, optionally sterically hindered amino acid residue; and
one or more residues of said sequence optionally includes side chain protection; and e) providing a fourth peptide fragment including the amino acid sequence of (SEQ ID NO. 18)

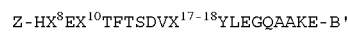

wherein
$X^8$ and $X^{10}$ are each independently achiral, optionally sterically hindered amino acid residues;
$X^{17-18}$ is a dipeptide residue of a pseudoproline;
Z is an N-terminal protecting group;
B' is a solid phase resin; and
one or more residues of said sequence optionally includes side chain protection; and f) cleaving the fourth peptide fragment of step e) from the solid phase resin to yield the fourth peptide fragment in solution (SEQ ID NO. 18)

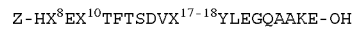

g) coupling the fourth peptide fragment to the third peptide fragment in solution in order to provide a fifth peptide fragment including the amino acid sequence of (SEQ ID NO. 26)

wherein
Z is an N-terminal protecting group;
$X^8$ and $X^{10}$ are each independently achiral, optionally sterically hindered amino acid residues;
$X^{17-18}$ is a dipeptide residue of a pseudoproline;
$X^{35}$ is an achiral, optionally sterically hindered amino acid residue; and
one or more residues of said sequence optionally includes side chain protection;

h) removing the N-terminal protecting group to afford a sixth peptide fragment including the amino acid sequence of (SEQ ID NO. 26)

wherein
Z is H—;
$X^8$ and $X^{10}$ are each independently achiral, optionally sterically hindered amino acid residues;
$X^{17-18}$ is a dipeptide residue of a pseudoproline;
$X^{35}$ is an achiral, optionally sterically hindered amino acid residue; and
one or more residues of said sequence optionally includes side chain protection.

In one aspect, the application provides a method comprising the step of:

a) providing a first peptide fragment including the amino acid sequence of (SEQ ID NO. 16)

Z-FIAWLVKX³⁵-B' wherein
X³⁵ is an achiral, optionally sterically hindered amino acid residue;
Z is an N-terminal protecting group Fmoc-;
B' is a solid phase resin; and
one or more residues of said sequence optionally includes side chain protection;

b) cleaving the first peptide fragment of step a) from the solid phase resin to yield the first peptide fragment in solution (SEQ ID NO. 16)

Z-FIAWLVKX³⁵-OH c) coupling the first peptide fragment in solution to arginine amide in order to provide a second peptide fragment including the amino acid sequence of (SEQ ID NO. 17)

Z-FIAWLVKX³⁵R-NH₂ wherein
Z is an N-terminal protecting group;
X³⁵ is an achiral, optionally sterically hindered amino acid residue; and
one or more residues of said sequence optionally includes side chain protection;

d) removing the N-terminal protecting group to afford a third peptide fragment including the amino acid sequence of (SEQ ID NO. 17)

Z-FIAWLVKX³⁵R-NH₂ wherein
Z is H—;
X³⁵ is an achiral, optionally sterically hindered amino acid residue; and
one or more residues of said sequence optionally includes side chain protection; and e) providing a fourth peptide fragment including the amino acid sequence of (SEQ ID NO. 18)

Z-HX⁸EX¹⁰TFTSDVX¹⁷⁻¹⁸YLEGQAAKE-B' wherein
X⁸ and X¹⁰ are each independently achiral, optionally sterically hindered amino acid residues;
X¹⁷⁻¹⁸ is a dipeptide residue of a pseudoproline;
Z is an N-terminal protecting group;
B' is a solid phase resin; and
one or more residues of said sequence optionally includes side chain protection; and f) cleaving the fourth peptide fragment of step e) from the solid phase resin to yield the fourth peptide fragment in solution (SEQ ID NO. 18)

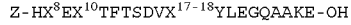
Z-HX⁸EX¹⁰TFTSDVX¹⁷⁻¹⁸YLEGQAAKE-OH g) coupling the fourth peptide fragment to the third peptide fragment in solution in order to provide a fifth peptide fragment including the amino acid sequence of (SEQ ID NO. 26)

Z-HX⁸EX¹⁰TFTSDVX¹⁷⁻¹⁸YLEGQAAKEFIAWLVKX³⁵R-NH₂ wherein
Z is an N-terminal protecting group;
X⁸ and X¹⁰ are each independently achiral, optionally sterically hindered amino acid residues;
X¹⁷⁻¹⁸ is a dipeptide residue of a pseudoproline;
X³⁵ is an achiral, optionally sterically hindered amino acid residue; and
one or more residues of said sequence optionally includes side chain protection;

h) removing the N-terminal protecting group to afford a sixth peptide fragment including the amino acid sequence of (SEQ ID NO. 26)

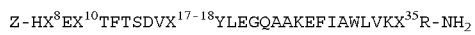
Z-HX⁸EX¹⁰TFTSDVX¹⁷⁻¹⁸YLEGQAAKEFIAWLVKX³⁵R-NH₂ wherein
Z is H—;
X⁸ and X¹⁰ are each independently achiral, optionally sterically hindered amino acid residues;
X¹⁷⁻¹⁸ is a dipeptide residue of a pseudoproline;
X³⁵ is an achiral, optionally sterically hindered amino acid residue; and
one or more residues of said sequence optionally includes side chain protection; and i) contacting the insulinotropic peptide resulting from step h) with acid in order to deprotect the amino acid side chains to afford the deprotected insulinotropic peptide including amino acid sequence of (SEQ ID NO. 19)

Z-HX⁸EX¹⁰TFTSDVSSYLEGQAAKEFIAWLVKX³⁵R-NH₂ wherein
Z is H—; and
X⁸, X¹⁰ and X³⁵ are each independently achiral, optionally sterically hindered amino acid residues.

In one aspect, the application provides the above method wherein the deprotected insulinotropic peptide has the amino acid sequence (SEQ. ID No. 12)

HAibEGTFTSDVSSYLEGQAAKEFIAWLVKAibR

In one aspect, the application provides a peptide of the amino acid sequence (SEQ. ID NO. 18)

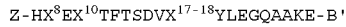
Z-HX⁸EX¹⁰TFTSDVX¹⁷⁻¹⁸YLEGQAAKE-B' wherein
Z is selected from H— and Fmoc-;
B' is —OH or solid phase resin;
X¹⁷⁻¹⁸ is a dipeptide residue of a pseudoproline; and
one or more residues of said sequence optionally include side chain protection.

In one variation of the above peptide, the dipeptide residue of a pseudoproline is a Ser-Ser residue of a pseudoproline.

In one aspect, the application provides a method of making an insulinotropic peptide, comprising the steps of:

a) providing a first peptide fragment including the amino acid sequence of (SEQ ID NO. 5)

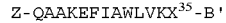
Z-QAAKEFIAWLVKX$^{35}$-B' wherein

X$^{35}$ is an achiral, optionally sterically hindered amino acid residue;

Z is an N-terminal protecting group;

B' is —OH; and one or more residues of said sequence optionally includes side chain protection;

b) coupling the first peptide fragment in solution to arginine amide in order to provide a second peptide fragment including the amino acid sequence of (SEQ ID NO. 6)

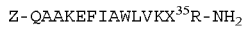
Z-QAAKEFIAWLVKX$^{35}$R-NH$_2$ wherein

Z is an N-terminal protecting group;

X$^{35}$ is an achiral, optionally sterically hindered amino acid residue; and one or more residues of said sequence optionally includes side chain protection;

c) removing the N-terminal protecting group to afford a third peptide fragment including the amino acid sequence of (SEQ ID NO. 6)

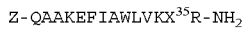
Z-QAAKEFIAWLVKX$^{35}$R-NH$_2$ wherein

Z is H—;

X$^{35}$ is an achiral, optionally sterically hindered amino acid residue; and one or more residues of said sequence optionally includes side chain protection;

d) providing a fourth peptide fragment including the amino acid sequence of (SEQ ID NO. 7)

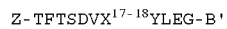
Z-TFTSDVX$^{17-18}$YLEG-B' wherein

X$^{17-18}$ is a dipeptide residue of a pseudoproline;

Z is an N-terminal protecting group;

B' is —OH; and one or more residues of said sequence optionally includes side chain protection;

e) coupling the fourth peptide fragment to the third peptide fragment in solution in order to provide a fifth peptide fragment including the amino acid sequence of (SEQ ID NO. 8)

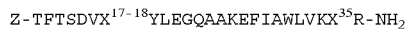
Z-TFTSDVX$^{17-18}$YLEGQAAKEFIAWLVKX$^{35}$R-NH$_2$ wherein

Z is an N-terminal protecting group;

X$^{17-18}$ is a dipeptide residue of a pseudoproline;

X$^{35}$ is an achiral, optionally sterically hindered amino acid residue; and one or more residues of said sequence optionally includes side chain protection;

f) removing the N-terminal protecting group to afford a sixth peptide fragment including the amino acid sequence of (SEQ ID NO. 8)

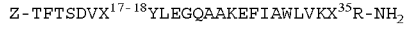
Z-TFTSDVX$^{17-18}$YLEGQAAKEFIAWLVKX$^{35}$R-NH$_2$ wherein

Z is H—;

X$^{17-18}$ is a dipeptide residue of a pseudoproline;

X$^{35}$ is an achiral, optionally sterically hindered amino acid residue; and one or more residues of said sequence optionally includes side chain protection;

g) providing a seventh peptide fragment including the amino acid sequence of (SEQ ID NO. 9)

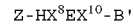
Z-HX$^8$EX$^{10}$-B' wherein

X$^8$ and X$^{10}$ are each independently achiral, optionally sterically hindered amino acid residues;

Z is an N-terminal protecting group;

B' is —OH; and each of H and E optionally includes side chain protection; and h) coupling the seventh peptide fragment to the sixth peptide fragment in solution to provide an insulinotropic peptide including the amino acid sequence of (SEQ ID NO. 10)

Z-HX$^8$EX$^{10}$TFTSDVX$^{17-18}$YLEGQAAKEFIAWLVKX$^{35}$R-NH$_2$ wherein Z is an N-terminal protecting group;

X$^{17-18}$ is a dipeptide residue of a pseudoproline;

X$^8$, X$^{10}$ and X$^{35}$ are each independently achiral, optionally sterically hindered amino acid residues; and one or more residues of said sequence optionally includes side chain protection.

An "N-terminal protecting group" means a group selected from the group consisting of Acr (acrylyl), Bz (benzoyl), Ac (acetyl), Trt (trityl) Boc (t-butyloxycarbonyl), CBz (benzyloxy-carbonyl or Z), Dts (dithiasuccinoyl), Rdtc (R=Alkyl or Aryl, dtc=dithiocarbamate), DBFmoc (2,7-di-t-butylFmoc or 1,7-di-t-butylfluoren-9-ylmethoxycarbonyl), Alloc (allyloxycarbonyl), pNZ (p-nitrobenzyloxycarbonyl), Nsc ([[2-[(4-nitrophenyl)sulfonyl]-ethoxy]carbonyl]), Msc (2-methylsulfonylethoxycarbonyl), MBz (4-methoxyCBz), Poc (2-phenylpropyl(2)-oxycarbonyl), Bpoc [(1-[1,1'-biphenyl]-4-yl-1-methylethoxy)carbonyl], Bnpeoc [[2,2-bis(4-nitrophenyl)-ethoxy]carbonyl], CBz [(phenylmethoxy)carbonyl], Aoc [(1,1-dimethylpropoxy)carbonyl], and Moz [[(4-methoxyphenyl)methoxy]carbonyl]. Preferred N-terminal protecting groups are Fmoc, Bpoc, Trt, Poc and Boc.

An "achiral, optionally sterically hindered amino acid residue" is an amino acid that may be derived from the native achiral glycine or another achiral amino acid. Preferably, the achiral, optionally sterically hindered amino acid residue is selected from the group consisting of glycine (G), 2-methylalanine (Aib) and 2-phenylmethyl-phenylalanine. Most preferably, the achiral, optionally sterically hindered amino acid residue is selected from G or Aib.

In a preferred aspect, the application provides a method of making an insulinotropic peptide, comprising the steps of:

a) providing a first peptide fragment including the amino acid sequence of (SEQ ID NO. 5)

$$Z\text{-QAAKEFIAWLVKX}^{35}\text{-B'}$$

wherein $X^{35}$ is an achiral, optionally sterically hindered amino acid residue;

Z is N-terminal protecting group Fmoc-;

B' is —OH; and one or more residues of said sequence optionally includes side chain protection;

b) coupling the first peptide fragment in solution to arginine amide in order to provide a second peptide fragment including the amino acid sequence of (SEQ ID NO. 6)

$$Z\text{-QAAKEFIAWLVKX}^{35}\text{R-NH}_2$$

wherein

Z is N-terminal protecting group Fmoc-;

$X^{35}$ is an achiral, optionally sterically hindered amino acid residue; and one or more residues of said sequence optionally includes side chain protection;

c) removing the N-terminal protecting group to afford a third peptide fragment including the amino acid sequence of (SEQ ID NO. 6)

$$Z\text{-QAAKEFIAWLVKX}^{35}\text{R-NH}_2$$

wherein

Z is H—;

$X^{35}$ is an achiral, optionally sterically hindered amino acid residue; and one or more residues of said sequence optionally includes side chain protection;

d) providing a fourth peptide fragment including the amino acid sequence of (SEQ ID NO. 7)

$$Z\text{-TFTSDVX}^{17\text{-}18}\text{YLEG-B'}$$

wherein $X^{17\text{-}18}$ is a dipeptide residue of a pseudoproline;

Z is N-terminal protecting group Fmoc-;

B' is —OH; and one or more residues of said sequence optionally includes side chain protection;

e) coupling the fourth peptide fragment to the third peptide fragment in solution in order to provide a fifth peptide fragment including the amino acid sequence of (SEQ ID NO. 8)

$$Z\text{-TFTSDVX}^{17\text{-}18}\text{YLEGQAAKEFIAWLVKX}^{35}\text{R-NH}_2$$

wherein

Z is N-terminal protecting group Fmoc-;

$X^{17\text{-}18}$ is a dipeptide residue of a pseudoproline;

$X^{35}$ is an achiral, optionally sterically hindered amino acid residue; and one or more residues of said sequence optionally includes side chain protection;

f) removing the N-terminal protecting group to afford a sixth peptide fragment including the amino acid sequence of (SEQ ID NO. 8)

$$Z\text{-TFTSDVX}^{17\text{-}18}\text{YLEGQAAKEFIAWLVKX}^{35}\text{R-NH}_2$$

wherein

Z is H—;

$X^{17\text{-}18}$ is a dipeptide residue of a pseudoproline;

$X^{35}$ is an achiral, optionally sterically hindered amino acid residue; and one or more residues of said sequence optionally includes side chain protection;

g) providing a seventh peptide fragment including the amino acid sequence of (SEQ ID NO. 9)

$$Z\text{-HX}^8\text{EX}^{10}\text{-B'}$$

wherein $X^8$ and $X^{10}$ are each independently achiral, optionally sterically hindered amino acid residues;

Z is N-terminal protecting group Fmoc-;

B' is —OH; and each of H and E optionally includes side chain protection; and h) coupling the seventh peptide fragment to the sixth peptide fragment in solution to provide an insulinotropic peptide including the amino acid sequence of (SEQ ID NO. 10)

$$Z\text{-HX}^8\text{EX}^{10}\text{TFTSDVX}^{17\text{-}18}\text{YLEGQAAKEFIAWLVKX}^{35}\text{R-NH}_2$$

wherein

Z is N-terminal protecting group Fmoc-;

$X^{17\text{-}18}$ is a dipeptide residue of a pseudoproline;

$X^8$, $X^{10}$ and $X^{35}$ are each independently achiral, optionally sterically hindered amino acid residues; and one or more residues of said sequence optionally includes side chain protection.

In another aspect, the application provides the above method, further comprising the steps of:

i) removing the N-terminal protecting group of the insulinotropic peptide to afford the insulinotropic peptide including amino acid sequence of (SEQ ID NO. 10)

$$Z\text{-HX}^8\text{EX}^{10}\text{TFTSDVX}^{17\text{-}18}\text{YLEGQAAKEFIAWLVKX}^{35}\text{R-NH}_2$$

wherein

Z is H—;

$X^{17\text{-}18}$ is a dipeptide residue of a pseudoproline;

$X^8$, $X^{10}$ and $X^{35}$ are each independently achiral, optionally sterically hindered amino acid residues; and one or more residues of said sequence optionally includes side chain protection; and j) contacting the insulinotropic peptide resulting from step i) with acid in order to deprotect the amino acid side chains to afford the deprotected insulinotropic peptide including amino acid sequence of (SEQ ID NO. 11)

$$Z\text{-HX}^8\text{EX}^{10}\text{TFTSDVSSYLEGQAAKEFIAWLVKX}^{35}\text{R-NH}_2$$

wherein

Z is H—; and $X^8$, $X^{10}$ and $X^{35}$ are each independently achiral, optionally sterically hindered amino acid residues.

In yet another aspect, the application provides the above method, wherein the deprotected insulinotropic peptide has the amino acid sequence (SEQ. ID No. 12)

In one aspect, the application provides a method of making an insulinotropic peptide, comprising the steps of:
a) providing a first peptide fragment including the amino acid sequence of (SEQ ID NO. 5)

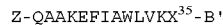

wherein
$X^{35}$ is an achiral, optionally sterically hindered amino acid residue;
Z is an N-terminal protecting group;
B' is a solid phase resin; and
one or more residues of said sequence optionally includes side chain protection;
b) removing the N-terminal protecting group to afford a second peptide fragment including the amino acid sequence of (SEQ ID NO. 5)

wherein
Z is H—;
B' is a solid phase resin;
$X^{35}$ is an achiral, optionally sterically hindered amino acid residue; and
one or more residues of said sequence optionally includes side chain protection;
c) providing a third peptide fragment in solution including the amino acid sequence of (SEQ ID NO. 7)

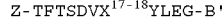

wherein
$X^{17-18}$ is a dipeptide residue of a pseudoproline;
Z is an N-terminal protecting group;
B' is —OH; and
one or more residues of said sequence optionally includes side chain protection;
d) coupling the third peptide fragment in solution to the second peptide fragment in solid phase in order to provide a fourth peptide fragment including the amino acid sequence of (SEQ ID NO. 13)

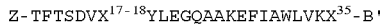

wherein
Z is an N-terminal protecting group;
B' is a solid phase resin;
$X^{17-18}$ is a dipeptide residue of a pseudoproline;
$X^{35}$ is an achiral, optionally sterically hindered amino acid residue; and
one or more residues of said sequence optionally includes side chain protection;
e) removing the fourth peptide fragment from the solid phase resin and coupling the fourth peptide fragment in solution to arginine amide in order to provide a fifth peptide fragment including the amino acid sequence of (SEQ ID NO. 8)

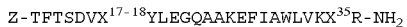

wherein
Z is an N-terminal protecting group;
$X^{17-18}$ is a dipeptide residue of a pseudoproline;
$X^{35}$ is an achiral, optionally sterically hindered amino acid residue; and
one or more residues of said sequence optionally includes side chain protection;
f) removing the N-terminal protecting group to afford a sixth peptide fragment including the amino acid sequence of (SEQ ID NO. 8)

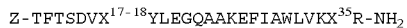

wherein
Z is H—;
$X^{17-18}$ is a dipeptide residue of a pseudoproline;
$X^{35}$ is an achiral, optionally sterically hindered amino acid residue; and
one or more residues of said sequence optionally includes side chain protection;
g) providing a seventh peptide fragment including the amino acid sequence of (SEQ ID NO. 9)

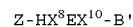

wherein
$X^8$ and $X^{10}$ are each independently achiral, optionally sterically hindered amino acid residues;
Z is an N-terminal protecting group;
B' is —OH; and
each of H and E optionally includes side chain protection; and
h) coupling the seventh peptide fragment to the sixth peptide fragment in solution to provide an insulinotropic peptide including the amino acid sequence of (SEQ ID NO. 10)

wherein
Z is an N-terminal protecting group;
$X^{17-18}$ is a dipeptide residue of a pseudoproline;
$X^8$, $X^{10}$ and $X^{35}$ are each independently achiral, optionally sterically hindered amino acid residues; and
one or more residues of said sequence optionally includes side chain protection.

In a preferred aspect, the application provides a method of making an insulinotropic peptide, comprising the steps of:
a) providing a first peptide fragment including the amino acid sequence of (SEQ ID NO. 5)

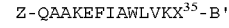

wherein
$X^{35}$ is an achiral, optionally sterically hindered amino acid residue;
Z is N-terminal protecting group Fmoc-;
B' is a solid phase resin; and
one or more residues of said sequence optionally includes side chain protection;
b) removing the N-terminal protecting group to afford a second peptide fragment including the amino acid sequence of (SEQ ID NO. 5)

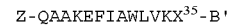

wherein

Z is H—;

B' is a solid phase resin;

$X^{35}$ is an achiral, optionally sterically hindered amino acid residue; and one or more residues of said sequence optionally includes side chain protection;

c) providing a third peptide fragment in solution including the amino acid sequence of (SEQ ID NO. 7)

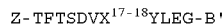

wherein $X^{17-18}$ is a dipeptide residue of a pseudoproline;

Z is N-terminal protecting group Fmoc-;

B' is —OH; and one or more residues of said sequence optionally includes side chain protection;

d) coupling the third peptide fragment in solution to the second peptide fragment in solid phase in order to provide a fourth peptide fragment including the amino acid sequence of (SEQ ID NO. 13)

wherein

Z is N-terminal protecting group Fmoc-;

B' is a solid phase resin;

$X^{17-18}$ is a dipeptide residue of a pseudoproline;

$X^{35}$ is an achiral, optionally sterically hindered amino acid residue; and one or more residues of said sequence optionally includes side chain protection;

e) removing the fourth peptide fragment from the solid phase resin and coupling the fourth peptide fragment in solution to arginine amide in order to provide a fifth peptide fragment including the amino acid sequence of (SEQ ID NO. 8)

wherein

Z is N-terminal protecting group Fmoc-;

$X^{17-18}$ is a dipeptide residue of a pseudoproline;

$X^{35}$ is an achiral, optionally sterically hindered amino acid residue; and one or more residues of said sequence optionally includes side chain protection;

f) removing the N-terminal protecting group to afford a sixth peptide fragment including the amino acid sequence of (SEQ ID NO. 8)

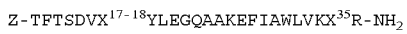

wherein

Z is H—;

$X^{17-18}$ is a dipeptide residue of a pseudoproline;

$X^{35}$ is an achiral, optionally sterically hindered amino acid residue; and one or more residues of said sequence optionally includes side chain protection;

g) providing a seventh peptide fragment including the amino acid sequence of (SEQ ID NO. 9)

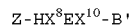

wherein $X^8$ and $X^{10}$ are each independently achiral, optionally sterically hindered amino acid residues;

Z is N-terminal protecting group Fmoc-;

B' is —OH; and each of H and E optionally includes side chain protection; and h) coupling the seventh peptide fragment to the sixth peptide fragment in solution to provide an insulinotropic peptide including the amino acid sequence of (SEQ ID NO. 10)

wherein

Z is N-terminal protecting group Fmoc-;

$X^{17-18}$ is a dipeptide residue of a pseudoproline;

$X^8$, $X^{10}$ and $X^{35}$ are each independently achiral, optionally sterically hindered amino acid residues; and one or more residues of said sequence optionally includes side chain protection.

In another aspect, the application provides the above method, further comprising the steps of:

i) removing the N-terminal protecting group of the insulinotropic peptide to afford the insulinotropic peptide including amino acid sequence of (SEQ ID NO. 10)

wherein

Z is H—;

$X^{17-18}$ is a dipeptide residue of a pseudoproline;

$X^8$, $X^{10}$ and $X^{35}$ are each independently achiral, optionally sterically hindered amino acid residues; and one or more residues of said sequence optionally includes side chain protection; and j) contacting the insulinotropic peptide resulting from step i) with acid to deprotect the amino acid side chains to afford the deprotected insulinotropic peptide including amino acid sequence of (SEQ ID NO. 11)

wherein

Z is H—; and $X^8$, $X^{10}$ and $X^{35}$ are each independently achiral, optionally sterically hindered amino acid residues.

In yet another aspect, the application provides the above method, wherein the deprotected insulinotropic peptide has the amino acid sequence (SEQ. ID No. 12)

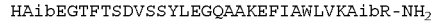

A "solid phase resin" means any type of support suitable in the practice of solid phase peptide synthesis that can be made from one or more polymers, copolymers or combinations of polymers such as polyamide, polysulfamide, substituted polyethylenes, polyethyleneglycol, phenolic resins, polysaccharides, or polystyrene and that typically includes a linking moiety to which the growing peptide is coupled during synthesis. Preferably, the solid phase resin is selected from the group consisting of 2-chlorotrityl chloride (2-CTC) resin, trityl chloride resin, 4-methyltrityl chloride resin, 4-methoxytrityl chloride resin, 4-aminobutan-1-ol 2-chlorotrityl resin, 4-aminomethylbenzoyl 2-chlorotrityl resin, 3-aminopropan-1-ol 2-chlorotrityl resin, bromoacetic acid 2-chlorotrityl resin, cyanoacetic acid 2-chlorotrityl resin, 4-cyanobenzoic acid 2-chlorotrityl resin, glicinol 2-chlorotrityl resin, propionic 2-chlorotrityl resin, ethyleneglycol 2-chlorotrityl resin, N-Fmoc hydroxylamine 2-chlorotrityl resin, hydrazine 2-chlorotrityl resin, polystyrene-divinylbenzene resin (PS resin) with 4-hydroxymethylphenyloxymethyl anchoring groups, and 4-hydroxymethyl-3-methoxyphenoxybutyric acid resin. Most preferably, the solid phase resin is 2-chlorotrityl chloride (2-CTC) resin.

In one aspect, the application provides a method of making an insulinotropic peptide, comprising the steps of:

a) providing a first peptide fragment or counterpart thereof including the amino acid sequence of (SEQ ID NO. 13)

wherein

Z is an N-terminal protecting group;

B' is —OH;

$X^{17-18}$ is a dipeptide residue of a pseudoproline;

$X^{35}$ is an achiral, optionally sterically hindered amino acid residue; and one or more residues of said sequence optionally include side chain protection;

b) coupling the first peptide fragment in solution to arginine amide in order to provide a second peptide fragment including the amino acid sequence of (SEQ ID NO. 8)

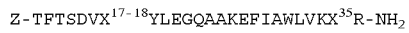

wherein

Z is an N-terminal protecting group;

$X^{17-18}$ is a dipeptide residue of a pseudoproline;

$X^{35}$ is an achiral, optionally sterically hindered amino acid residue; and one or more residues of said sequence optionally includes side chain protection;

c) removing the N-terminal protecting group to afford a third peptide fragment including the amino acid sequence of (SEQ ID NO. 8)

wherein

Z is H—;

$X^{17-18}$ is a dipeptide residue of a pseudoproline;

$X^{35}$ is an achiral, optionally sterically hindered amino acid residue; and one or more residues of said sequence optionally includes side chain protection;

d) providing a fourth peptide fragment including the amino acid sequence of (SEQ ID NO. 9)

wherein $X^8$ and $X^{10}$ are each independently achiral, optionally sterically hindered amino acid residues;

Z is an N-terminal protecting group;

B' is —OH; and each of H and E optionally includes side chain protection; and e) coupling the fourth peptide fragment to the third peptide fragment in solution to provide an insulinotropic peptide including the amino acid sequence of (SEQ ID NO. 10)

wherein

Z is an N-terminal protecting group;

$X^{17-18}$ is a dipeptide residue of a pseudoproline;

$X^8$, $X^{10}$ and $X^{35}$ are each independently achiral, optionally sterically hindered amino acid residues; and one or more residues of said sequence optionally includes side chain protection.

In a preferred aspect, the application provides a method of making an insulinotropic peptide, comprising the steps of:

a) providing a first peptide fragment or counterpart thereof including the amino acid sequence of (SEQ ID NO. 13)

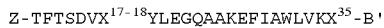

wherein

Z is N-terminal protecting group Fmoc-;

B' is —OH;

$X^{17-18}$ is a dipeptide residue of a pseudoproline;

$X^{35}$ is an achiral, optionally sterically hindered amino acid residue; and one or more residues of said sequence optionally include side chain protection;

b) coupling the first peptide fragment in solution to arginine amide in order to provide a second peptide fragment including the amino acid sequence of (SEQ ID NO. 8)

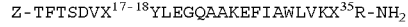

wherein

Z is N-terminal protecting group Fmoc-;

$X^{17-18}$ is a dipeptide residue of a pseudoproline;

$X^{35}$ is an achiral, optionally sterically hindered amino acid residue; and one or more residues of said sequence optionally includes side chain protection;

c) removing the N-terminal protecting group to afford a third peptide fragment including the amino acid sequence of (SEQ ID NO. 8)

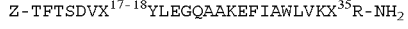

wherein

Z is H—;

$X^{17-18}$ is a dipeptide residue of a pseudoproline;

$X^{35}$ is an achiral, optionally sterically hindered amino acid residue; and one or more residues of said sequence optionally includes side chain protection;

d) providing a fourth peptide fragment including the amino acid sequence of (SEQ ID NO. 9)

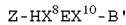

wherein
$X^8$ and $X^{10}$ are each independently achiral, optionally sterically hindered amino acid residues;
Z is N-terminal protecting group Fmoc-;
B' is —OH; and
each of H and E optionally includes side chain protection; and
e) coupling the fourth peptide fragment to the third peptide fragment in solution to provide an insulinotropic peptide including the amino acid sequence of (SEQ ID NO. 10)

wherein
Z is N-terminal protecting group Fmoc-;
$X^{17-18}$ is a dipeptide residue of a pseudoproline;
$X^8$, $X^{10}$ and $X^{35}$ are each independently achiral, optionally sterically hindered amino acid residues; and
one or more residues of said sequence optionally includes side chain protection.

In another aspect, the application provides the above method, further comprising the steps of:
i) removing the N-terminal protecting group of the insulinotropic peptide to afford the insulinotropic peptide including amino acid sequence of (SEQ ID NO. 10)

wherein
Z is H—;
$X^{17-18}$ is a dipeptide residue of a pseudoproline;
$X^8$, $X^{10}$ and $X^{35}$ are each independently achiral, optionally sterically hindered amino acid residues; and
one or more residues of said sequence optionally includes side chain protection; and
j) contacting the insulinotropic peptide resulting from step i) with acid to deprotect the amino acid side chains to afford the deprotected insulinotropic peptide including amino acid sequence of (SEQ ID NO. 11)

wherein
Z is H—; and
$X^8$, $X^{10}$ and $X^{35}$ are each independently achiral, optionally sterically hindered amino acid residues.

In yet another aspect, the application provides the above method, wherein the deprotected insulinotropic peptide has the amino acid sequence (SEQ. ID No. 12)

Any of the above methods may employ N-terminus histidine protecting groups (N-terminal protecting groups) selected from the group consisting of Boc (t-butyloxycarbonyl), CBz (benzyloxycarbonyl or Z), Dts (dithiasuccinoyl), Rdtc (R=Alkyl or Aryl, dtc=dithiocarbamate), DBFmoc (2,7-di-t-butylFmoc or 1,7-di-t-butylfluoren-9-ylmethoxycarbonyl), Alloc (allyloxycarbonyl), pNZ (p-nitrobenzyloxycarbonyl), Nsc ([[2-[(4-nitrophenyl)sulfonyl]-ethoxy]carbonyl]), Msc (2-methylsulfonylethoxycarbonyl), MBz (4-methoxy-CBz), Bpoc [(1-[1,1'-biphenyl]-4-yl-1-methylethoxy)carbonyl], Bnpeoc [[2,2-bis(4-nitrophenyl)ethoxy]-carbonyl], CBz [(phenylmethoxy)carbonyl], Aoc [(1,1-dimethylpropoxy)carbonyl], and Moz [[(4-methoxyphenyl)methoxy]carbonyl], wherein if the N-terminus histidine protecting group may be removed in the global side-chain deprotection step using acid, prior removal of the N-terminus histidine protecting group is not required.

In one aspect, the application provides a peptide of the amino acid sequence (SEQ. ID NO. 14)

wherein
Z is selected from H— and Fmoc-;
B' is —OH or solid phase resin;
$X^{17-18}$ is a dipeptide residue of a pseudoproline; and
one or more residues of said sequence optionally include side chain protection.

In another aspect, the application provides the above peptide, wherein the dipeptide residue of a pseudoproline is a Ser-Ser residue.

In one aspect, the application provides a peptide of the amino acid sequence (SEQ. ID NO. 15)

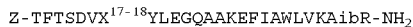

wherein
Z is selected from H— and Fmoc-;
$X^{17-18}$ is a dipeptide residue of a pseudoproline; and
one or more residues of said sequence optionally include side chain protection.

In another aspect, the application provides the above peptide, wherein the dipeptide residue of a pseudoproline is a Ser-Ser residue.

The present application relates to the preparation of insulinotropic peptides that are synthesized using a solid and solution phase ("hybrid") approach. Generally, the approach includes synthesizing three different peptide intermediate fragments using solid phase chemistry. Solution phase chemistry is then used to add additional amino acid material to one of the fragments. The fragments are then coupled together in the solution phase. The use of a pseudoproline in one of the fragments eases the solid phase synthesis of that fragment and also eases the subsequent solution phase coupling of this fragment to other fragments. The present invention is very useful for forming insulinotropic peptides such as GLP-1, GLP-1(7-36) and natural and non-natural counterparts of these, particularly GLP-1(7-36) and its natural and non-natural counterparts.

In one aspect, the application provides a method of making an insulinotropic peptide, comprising the steps of:
a) providing a first peptide fragment including the amino acid sequence of (SEQ ID NO. 16)

wherein
$X^{35}$ is an achiral, optionally sterically hindered amino acid residue;
Z is an N-terminal protecting group;
B' is a solid phase resin; and
one or more residues of said sequence optionally includes side chain protection;

b) cleaving the first peptide fragment of step a) from the solid phase resin to yield the first peptide fragment in solution (SEQ ID NO. 16)

$$\text{Z-FIAWLVKX}^{35}\text{-B'}$$

wherein B' is —OH;

c) coupling the first peptide fragment in solution to arginine amide in order to provide a second peptide fragment including the amino acid sequence of (SEQ ID NO. 17)

$$\text{Z-FIAWLVKX}^{35}\text{R-NH}_2$$

wherein

Z is an N-terminal protecting group;

$X^{35}$ is an achiral, optionally sterically hindered amino acid residue; and one or more residues of said sequence optionally includes side chain protection;

d) removing the N-terminal protecting group to afford a third peptide fragment including the amino acid sequence of (SEQ ID NO. 17)

$$\text{Z-FIAWLVKX}^{35}\text{R-NH}_2$$

wherein

Z is H—;

$X^{35}$ is an achiral, optionally sterically hindered amino acid residue; and one or more residues of said sequence optionally includes side chain protection.

The "N-terminal protecting group" is selected from the group consisting of Acr (acrylyl), Bz (benzoyl), Ac (acetyl), Trt (trityl), Boc (t-butyloxycarbonyl), CBz (benzyloxycarbonyl or Z), Dts (dithiasuccinoyl), Rdtc (R=Alkyl or Aryl, dtc=dithiocarbamate), DBFmoc (2,7-di-t-butylFmoc or 1,7-di-t-butylfluoren-9-ylmethoxycarbonyl), Alloc (allyloxycarbonyl), pNZ (p-nitrobenzyloxycarbonyl), Nsc ([[2-[(4-nitrophenyl)sulfonyl]ethoxy]carbonyl]), Msc (2-methylsulfonylethoxycarbonyl), MBz (4-methoxyCBz), Poc (2-phenylpropyl(2)-oxycarbonyl), Bpoc [(1-[1,1'-biphenyl]-4-yl-1-methylethoxy)carbonyl], Bnpeoc [[2,2-bis(4-nitrophenyl)ethoxy]carbonyl], CBz [(phenylmethoxy)carbonyl], Aoc [(1,1-dimethylpropoxy)carbonyl], and Moz [[(4-methoxyphenyl)methoxy]carbonyl]. Preferred N-terminal protecting groups are Fmoc, Bpoc, Trt, Poc and Boc.

In a preferred aspect, the application provides a method of making an insulinotropic peptide, comprising the steps of:

a) providing a first peptide fragment including the amino acid sequence of (SEQ ID NO. 16)

$$\text{Z-FIAWLVKX}^{35}\text{-B'}$$

wherein $X^{35}$ is an achiral, optionally sterically hindered amino acid residue;

Z is N-terminal protecting group Fmoc-;

B' is a solid phase resin; and one or more residues of said sequence optionally includes side chain protection;

b) cleaving the first peptide fragment of step a) from the solid phase resin to yield the first peptide fragment in solution (SEQ ID NO. 16)

$$\text{Z-FIAWLVKX}^{35}\text{-B'}$$

wherein B' is —OH;

c) coupling the first peptide fragment in solution to arginine amide in order to provide a second peptide fragment including the amino acid sequence of (SEQ ID NO. 17)

$$\text{Z-FIAWLVKX}^{35}\text{R-NH}_2$$

wherein

Z is N-terminal protecting group Fmoc-;

$X^{35}$ is an achiral, optionally sterically hindered amino acid residue; and one or more residues of said sequence optionally includes side chain protection;

d) removing the N-terminal protecting group to afford a third peptide fragment including the amino acid sequence of (SEQ ID NO. 17)

$$\text{Z-FIAWLVKX}^{35}\text{R-NH}_2$$

wherein

Z is H—;

$X^{35}$ is an achiral, optionally sterically hindered amino acid residue; and one or more residues of said sequence optionally includes side chain protection.

In one aspect, the application provides a peptide prepared according to the above method having the amino acid sequence (SEQ ID NO. 17)

$$\text{Z-FIAWLVKX}^{35}\text{R-NH}_2$$

wherein

Z is N-terminal protecting group Fmoc-; and $X^{35}$ is an achiral, optionally sterically hindered amino acid residue; and one or more residues of said sequence optionally includes side chain protection.

In one variation of the above peptide, $X^{35}$ is Aib.

In one aspect, the application provides a peptide prepared according to the above method having the amino acid sequence (SEQ ID NO. 16)

$$\text{Z-FIAWLVKX}^{35}\text{-B'}$$

wherein

B' is solid phase resin or —OH;

Z is N-terminal protecting group Fmoc-; and $X^{35}$ is an achiral, optionally sterically hindered amino acid residue; and one or more residues of said sequence optionally includes side chain protection.

In one variation of the above peptide, $X^{35}$ is Aib.

In one aspect, the application provides a method of making an insulinotropic peptide, comprising the steps of:
a) providing a peptide fragment including the amino acid sequence of (SEQ ID NO. 18)

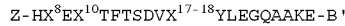

wherein
$X^8$ and $X^{10}$ are each independently achiral, optionally sterically hindered amino acid residues;
$X^{17-18}$ is a dipeptide residue of a pseudoproline;
Z is an N-terminal protecting group;
B' is a solid phase resin; and
one or more residues of said sequence optionally includes side chain protection; and
b) cleaving the peptide fragment of step a) from the solid phase resin to yield the peptide fragment in solution (SEQ ID NO. 18)

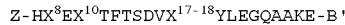

wherein B' is —OH.

In a preferred aspect, the application provides a method of making an insulinotropic peptide, comprising the steps of:
a) providing a peptide fragment including the amino acid sequence of (SEQ ID NO. 18)

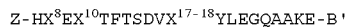

wherein
$X^8$ and $X^{10}$ are each independently achiral, optionally sterically hindered amino acid residues;
$X^{17-18}$ is a dipeptide residue of a pseudoproline;
Z is N-terminal protecting group Fmoc-;
B' is a solid phase resin; and
one or more residues of said sequence optionally includes side chain protection; and
b) cleaving the peptide fragment of step a) from the solid phase resin to yield the peptide fragment in solution (SEQ ID NO. 18)

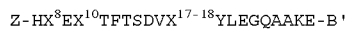

wherein B' is —OH.

In one aspect, the application provides a method comprising the steps of:
a) providing a first peptide fragment including the amino acid sequence of (SEQ ID NO. 16)

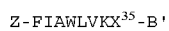

wherein
$X^{35}$ is an achiral, optionally sterically hindered amino acid residue;
Z is an N-terminal protecting group;
B' is a solid phase resin; and
one or more residues of said sequence optionally includes side chain protection;
b) cleaving the first peptide fragment of step a) from the solid phase resin to yield the first peptide fragment in solution (SEQ ID NO. 16)

wherein B' is —OH;

c) coupling the first peptide fragment in solution to arginine amide in order to provide a second peptide fragment including the amino acid sequence of (SEQ ID NO. 17)

wherein
Z is an N-terminal protecting group;
$X^{35}$ is an achiral, optionally sterically hindered amino acid residue; and
one or more residues of said sequence optionally includes side chain protection;
d) removing the N-terminal protecting group to afford a third peptide fragment including the amino acid sequence of (SEQ ID NO. 17)

wherein
Z is H—;
$X^{35}$ is an achiral, optionally sterically hindered amino acid residue; and
one or more residues of said sequence optionally includes side chain protection; and
e) providing a fourth peptide fragment including the amino acid sequence of (SEQ ID NO. 18)

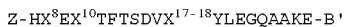

wherein
$X^8$ and $X^{10}$ are each independently achiral, optionally sterically hindered amino acid residues;
$X^{17-18}$ is a dipeptide residue of a pseudoproline;
Z is an N-terminal protecting group;
B' is a solid phase resin; and
one or more residues of said sequence optionally includes side chain protection; and
f) cleaving the fourth peptide fragment of step e) from the solid phase resin to yield the fourth peptide fragment in solution (SEQ ID NO. 18)

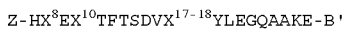

wherein B' is —OH.

In a preferred aspect, the application provides a method comprising the steps of:
a) providing a first peptide fragment including the amino acid sequence of (SEQ ID NO. 16)

wherein
$X^{35}$ is an achiral, optionally sterically hindered amino acid residue;
Z is N-terminal protecting group Fmoc-;
B' is a solid phase resin; and
one or more residues of said sequence optionally includes side chain protection;
b) cleaving the first peptide fragment of step a) from the solid phase resin to yield the first peptide fragment in solution (SEQ ID NO. 16)

wherein B' is —OH;

c) coupling the first peptide fragment in solution to arginine amide in order to provide a second peptide fragment including the amino acid sequence of (SEQ ID NO. 17)

Z-FIAWLVKX³⁵R-NH₂ wherein

Z is N-terminal protecting group Fmoc-;

X³⁵ is an achiral, optionally sterically hindered amino acid residue; and one or more residues of said sequence optionally includes side chain protection;

d) removing the N-terminal protecting group to afford a third peptide fragment including the amino acid sequence of (SEQ ID NO. 17)

Z-FIAWLVKX³⁵R-NH₂ wherein

Z is H—;

X³⁵ is an achiral, optionally sterically hindered amino acid residue; and one or more residues of said sequence optionally includes side chain protection; and e) providing a fourth peptide fragment including the amino acid sequence of (SEQ ID NO. 18)

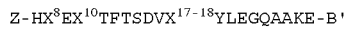
Z-HX⁸EX¹⁰TFTSDVX¹⁷⁻¹⁸YLEGQAAKE-B' wherein

X⁸ and X¹⁰ are each independently achiral, optionally sterically hindered amino acid residues;

X¹⁷⁻¹⁸ is a dipeptide residue of a pseudoproline;

Z is N-terminal protecting group Fmoc-;

B' is a solid phase resin; and one or more residues of said sequence optionally includes side chain protection; and f) cleaving the fourth peptide fragment of step e) from the solid phase resin to yield the fourth peptide fragment in solution (SEQ ID NO. 18)

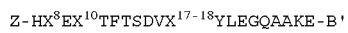
Z-HX⁸EX¹⁰TFTSDVX¹⁷⁻¹⁸YLEGQAAKE-B' wherein B' is —OH.

In one aspect, the application provides a method of making an insulinotropic peptide, comprising the step of:

a) coupling a first peptide fragment to a second peptide fragment in solution in order to provide a third peptide fragment including the amino acid sequence of (SEQ ID NO. 10)

Z-HX⁸EX¹⁰TFTSDVX¹⁷⁻¹⁸YLEGQAAKEFIAWLVKX³⁵R-NH₂ wherein

Z is an N-terminal protecting group;

X⁸ and X¹⁰ are each independently achiral, optionally sterically hindered amino acid residues;

X¹⁷⁻¹⁸ is a dipeptide residue of a pseudoproline;

X³⁵ is an achiral, optionally sterically hindered amino acid residue; and one or more residues of said sequence optionally includes side chain protection.

Preferably, the N-terminal protecting group is Fmoc.

In one aspect, the application provides a method comprising the step of:

a) providing a first peptide fragment including the amino acid sequence of (SEQ ID NO. 16)

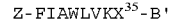
Z-FIAWLVKX³⁵-B' wherein

X³⁵ is an achiral, optionally sterically hindered amino acid residue;

Z is an N-terminal protecting group;

B' is a solid phase resin; and one or more residues of said sequence optionally includes side chain protection;

b) cleaving the first peptide fragment of step a) from the solid phase resin to yield the first peptide fragment in solution (SEQ ID NO. 16)

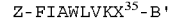
Z-FIAWLVKX³⁵-B' wherein B' is —OH;

c) coupling the first peptide fragment in solution to arginine amide in order to provide a second peptide fragment including the amino acid sequence of (SEQ ID NO. 17)

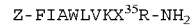
Z-FIAWLVKX³⁵R-NH₂ wherein

Z is an N-terminal protecting group;

X³⁵ is an achiral, optionally sterically hindered amino acid residue; and one or more residues of said sequence optionally includes side chain protection;

d) removing the N-terminal protecting group to afford a third peptide fragment including the amino acid sequence of (SEQ ID NO. 17)

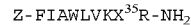
Z-FIAWLVKX³⁵R-NH₂ wherein

Z is H—;

X³⁵ is an achiral, optionally sterically hindered amino acid residue; and one or more residues of said sequence optionally includes side chain protection; and e) providing a fourth peptide fragment including the amino acid sequence of (SEQ ID NO. 18)

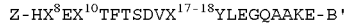
Z-HX⁸EX¹⁰TFTSDVX¹⁷⁻¹⁸YLEGQAAKE-B' wherein

X⁸ and X¹⁰ are each independently achiral, optionally sterically hindered amino acid residues; X¹⁷⁻¹⁸ is a dipeptide residue of a pseudoproline;

Z is an N-terminal protecting group;

B' is a solid phase resin; and one or more residues of said sequence optionally includes side chain protection; and f) cleaving the fourth peptide fragment of step e) from the solid phase resin to yield the fourth peptide fragment in solution (SEQ ID NO. 18)

Z-HX⁸EX¹⁰TFTSDVX¹⁷⁻¹⁸YLEGQAAKE-B' wherein B' is —OH;

g) coupling the fourth peptide fragment to the third peptide fragment in solution in order to provide a fifth peptide fragment including the amino acid sequence of (SEQ ID NO. 10)

wherein

Z is an N-terminal protecting group;

$X^8$ and $X^{10}$ are each independently achiral, optionally sterically hindered amino acid residues;

$X^{17-18}$ is a dipeptide residue of a pseudoproline;

$X^{35}$ is an achiral, optionally sterically hindered amino acid residue; and one or more residues of said sequence optionally includes side chain protection.

Preferably, the N-terminal protecting group is Fmoc.

In one aspect, the application provides a method comprising the step of:

a) providing a first peptide fragment including the amino acid sequence of (SEQ ID NO. 16)

wherein $X^{35}$ is an achiral, optionally sterically hindered amino acid residue;

Z is an N-terminal protecting group;

B' is a solid phase resin; and one or more residues of said sequence optionally includes side chain protection;

b) cleaving the first peptide fragment of step a) from the solid phase resin to yield the first peptide fragment in solution (SEQ ID NO. 16)

Z-FIAWLVKX$^{35}$-B', wherein B' is —OH;

c) coupling the first peptide fragment in solution to arginine amide in order to provide a second peptide fragment including the amino acid sequence of (SEQ ID NO. 17)

wherein

Z is an N-terminal protecting group;

$X^{35}$ is an achiral, optionally sterically hindered amino acid residue; and one or more residues of said sequence optionally includes side chain protection;

d) removing the N-terminal protecting group to afford a third peptide fragment including the amino acid sequence of (SEQ ID NO. 17)

wherein

Z is H—;

$X^{35}$ is an achiral, optionally sterically hindered amino acid residue; and one or more residues of said sequence optionally includes side chain protection; and e) providing a fourth peptide fragment including the amino acid sequence of (SEQ ID NO. 18)

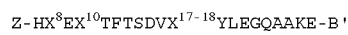

wherein $X^8$ and $X^{10}$ are each independently achiral, optionally sterically hindered amino acid residues;

$X^{17-18}$ is a dipeptide residue of a pseudoproline;

Z is an N-terminal protecting group;

B' is a solid phase resin; and one or more residues of said sequence optionally includes side chain protection; and f) cleaving the fourth peptide fragment of step e) from the solid phase resin to yield the fourth peptide fragment in solution (SEQ ID NO. 18)

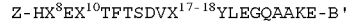

wherein B' is —OH;

g) coupling the fourth peptide fragment to the third peptide fragment in solution in order to provide a fifth peptide fragment including the amino acid sequence of (SEQ ID NO. 10)

wherein

Z is an N-terminal protecting group;

$X^8$ and $X^{10}$ are each independently achiral, optionally sterically hindered amino acid residues;

$X^{17-18}$ is a dipeptide residue of a pseudoproline;

$X^{35}$ is an achiral, optionally sterically hindered amino acid residue; and one or more residues of said sequence optionally includes side chain protection;

h) removing the N-terminal protecting group to afford a sixth peptide fragment including the amino acid sequence of (SEQ ID NO. 10)

wherein

Z is H—;

$X^8$ and $X^{10}$ are each independently achiral, optionally sterically hindered amino acid residues;

$X^{17-18}$ is a dipeptide residue of a pseudoproline;

$X^{35}$ is an achiral, optionally sterically hindered amino acid residue; and one or more residues of said sequence optionally includes side chain protection.

Preferably, the N-terminal protecting group is Fmoc.

In one aspect, the application provides a method comprising the step of:

a) providing a first peptide fragment including the amino acid sequence of (SEQ ID NO. 16)

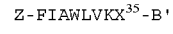

wherein $X^{35}$ is an achiral, optionally sterically hindered amino acid residue;

Z is an N-terminal protecting group Fmoc-;

B' is a solid phase resin; and one or more residues of said sequence optionally includes side chain protection;

b) cleaving the first peptide fragment of step a) from the solid phase resin to yield the first peptide fragment in solution (SEQ ID NO. 16)

Z-FIAWLVKX$^{35}$-B' wherein B' is —OH;
c) coupling the first peptide fragment in solution to arginine amide in order to provide a second peptide fragment including the amino acid sequence of (SEQ ID NO. 17)

Z-FIAWLVKX$^{35}$R-NH$_2$ wherein
Z is an N-terminal protecting group;
X$^{35}$ is an achiral, optionally sterically hindered amino acid residue; and
one or more residues of said sequence optionally includes side chain protection;
d) removing the N-terminal protecting group to afford a third peptide fragment including the amino acid sequence of (SEQ ID NO. 17)

Z-FIAWLVKX$^{35}$R-NH$_2$ wherein
Z is H—;
X$^{35}$ is an achiral, optionally sterically hindered amino acid residue; and
one or more residues of said sequence optionally includes side chain protection; and
e) providing a fourth peptide fragment including the amino acid sequence of (SEQ ID NO. 18)

Z-HX$^8$EX$^{10}$TFTSDVX$^{17-18}$YLEGQAAKE-B' wherein
X$^8$ and X$^{10}$ are each independently achiral, optionally sterically hindered amino acid residues;
X$^{17-18}$ is a dipeptide residue of a pseudoproline;
Z is N-terminal protecting group Fmoc-;
B' is a solid phase resin; and
one or more residues of said sequence optionally includes side chain protection; and
f) cleaving the fourth peptide fragment of step e) from the solid phase resin to yield the fourth peptide fragment in solution (SEQ ID NO. 18)

Z-HX$^8$EX$^{10}$TFTSDVX$^{17-18}$YLEGQAAKE-B' wherein B' is —OH;
g) coupling the fourth peptide fragment to the third peptide fragment in solution in order to provide a fifth peptide fragment including the amino acid sequence of (SEQ ID NO. 10)

Z-HX$^8$EX$^{10}$TFTSDVX$^{17-18}$YLEGQAAKEFIAWLVKX$^{35}$R-NH$_2$ wherein
Z is an N-terminal protecting group;
X$^8$ and X$^{10}$ are each independently achiral, optionally sterically hindered amino acid residues;
X$^{17-18}$ is a dipeptide residue of a pseudoproline;
X$^{35}$ is an achiral, optionally sterically hindered amino acid residue; and
one or more residues of said sequence optionally includes side chain protection;
h) removing the N-terminal protecting group to afford a sixth peptide fragment including the amino acid sequence of (SEQ ID NO. 10)

Z-HX$^8$EX$^{10}$TFTSDVX$^{17-18}$YLEGQAAKEFIAWLVKX$^{35}$R-NH$_2$ wherein
Z is H—;
X$^8$ and X$^{10}$ are each independently achiral, optionally sterically hindered amino acid residues;
X$^{17-18}$ is a dipeptide residue of a pseudoproline;
X$^{35}$ is an achiral, optionally sterically hindered amino acid residue; and
one or more residues of said sequence optionally includes side chain protection; and
i) contacting the insulinotropic peptide resulting from step h) with acid in order to deprotect the amino acid side chains to afford the deprotected insulinotropic peptide including amino acid sequence of (SEQ ID NO. 11)

Z-HX$^8$EX$^{10}$TFTSDVSSYLEGQAAKEFIAWLVKX$^{35}$R-NH$_2$ wherein
Z is H—; and
X$^8$, X$^{10}$ and X$^{35}$ are each independently achiral, optionally sterically hindered amino acid residues.

In one aspect, the application provides the above method wherein the deprotected insulinotropic peptide has the amino acid sequence (SEQ. ID No. 12)

HAibEGTFTSDVSSYLEGQAAKEFIAWLVKAibR

In one aspect, the application provides a peptide of the amino acid sequence (SEQ. ID NO. 18)

Z-HX$^8$EX$^{10}$TFTSDVX$^{17-18}$YLEGQAAKE-B' wherein
Z is selected from H— and Fmoc-;
B' is —OH or solid phase resin;
X$^{17-18}$ is a dipeptide residue of a pseudoproline; and
one or more residues of said sequence optionally include side chain protection.

In one variation of the above peptide, the dipeptide residue of a pseudoproline is a Ser-Ser residue.

In one aspect, any of the above methods may employ N-terminus histidine protecting groups (N-terminal protecting groups) selected from the group consisting of Boc (t-butyloxycarbonyl), CBz (benzyloxycarbonyl or Z), Dts (dithiasuccinoyl), Rdtc (R=Alkyl or Aryl, dtc=dithiocarbamate), DBFmoc (2,7-di-t-butylFmoc or 1,7-di-t-butylfluoren-9-yl-methoxycarbonyl), Alloc (allyloxycarbonyl), pNZ (p-nitrobenzyloxycarbonyl), Nsc ([[2-[(4-nitrophenyl)sulfonyl]ethoxy]carbonyl]), Msc (2-methylsulfonylethoxycarbonyl), MBz (4-methoxyCBz), Bpoc [(1-[1,1'-biphenyl]-4-yl-1-methylethoxy)carbonyl], Bnpeoc [[2,2-bis(4-nitrophenyl)ethoxy]carbonyl], CBz [(phenylmethoxy)carbonyl], Aoc [(1,1-dimethylpropoxy)carbonyl], and Moz [[(4-methoxyphenyl)methoxy]carbonyl], wherein if the N-terminus histidine protecting group may be removed in the global side-chain deprotection step using acid, prior removal of the N-terminus histidine protecting group is not required.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

The present invention is directed to synthetic methods for making peptides such as the glucagon-like peptide-1 (GLP-1), and natural and non-natural insulinotropically active counterparts thereof, using solid and/or solution phase techniques. Peptide molecules of the invention may be protected, unprotected, or partially protected. Protection may include N-terminus protection, side chain protection, and/or C-terminus protection. While the invention is generally directed at the synthesis of these glucagon-like peptides, their counterparts, fragments and their counterparts, and fusion products and their counterparts of these, the inventive teachings herein can also be applicable to the synthesis of other peptides, particularly those that are synthesized using a combination of solid phase and solution phase approaches. The invention is also applicable to the synthesis of peptide intermediate fragments associated with impurities, particularly pyroglutamate impurities. Preferred GLP-1 molecules useful in the practice of the present invention include natural and non-natural GLP-1 (7-36) and counterparts thereof.

As used herein, the term "including the amino acid sequence" preferably means "having the amino acid sequence".

As used herein, a "counterpart" refers to natural and non-natural analogs, derivatives, fusion compounds, salts, or the like of a peptide. As used herein, a peptide analog generally refers to a peptide having a modified amino acid sequence such as by one or more amino acid substitutions, deletions, inversions, and/or additions relative to another peptide or peptide counterpart. Substitutions may involve one or more natural or non-natural amino acids. Substitutions preferably may be conservative or highly conservative. A conservative substitution refers to the substitution of an amino acid with another that has generally the same net electronic charge and generally the same size and shape. For instance, amino acids with aliphatic or substituted aliphatic amino acid side chains have approximately the same size when the total number of carbon and heteroatoms in their side chains differs by no more than about four. They have approximately the same shape when the number of branches in their side chains differs by no more than about one or two. Amino acids with phenyl or substituted phenyl groups in their side chains are considered to have about the same size and shape. Listed below are five groups of amino acids. Replacing an amino acid in a compound with another amino acid from the same groups generally results in a conservative substitution.

Group I: glycine, alanine, valine, leucine, isoleucine, serine, threonine, cysteine, methionine and non-naturally occurring amino acids with $C_1$-$C_4$ aliphatic or $C_1$-$C_4$ hydroxyl substituted aliphatic side chains (straight chained or monobranched).

Group II: glutamic acid, aspartic acid and normaturally occurring amino acids with carboxylic acid substituted $C_1$-$C_4$ aliphatic side chains (unbranched or one branch point).

Group III: lysine, ornithine, arginine and normaturally occurring amino acids with amine or guanidino substituted $C_1$-$C_4$ aliphatic side chains (unbranched or one branch point).

Group IV: glutamine, asparagine and non-naturally occurring amino acids with amide substituted $C_1$-$C_4$ aliphatic side chains (unbranched or one branch point).

Group V: phenylalanine, phenylglycine, tyrosine and tryptophan.

As used herein, the term "counterpart" more preferably refers to the salts of a peptide, or to the derivatives thereof that are amidated at the C-terminus.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in their side chains. Examples of highly conservative substitutions include valine for leucine, threonine for serine, aspartic acid for glutamic acid and phenylglycine for phenylalanine.

A "peptide derivative" generally refers to a peptide, a peptide analog, or other peptide counterpart having chemical modification of one or more of its side groups, alpha carbon atoms, terminal amino group, and/or terminal carboxyl acid group. By way of example, a chemical modification includes, but is not limited to, adding chemical moieties, creating new bonds, and/or removing chemical moieties. Modifications at amino acid side groups include, without limitation, acylation of lysine e-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl (e.g., —CO-lower alkyl) modifications. Modifications of the terminal carboxy group include, without limitation, the amide, lower alkyl amide, dialkyl amide, and lower alkyl ester modifications. Thus, partially or wholly protected peptides constitute peptide derivatives.

In the practice of the present invention, a compound has "insulinotropic" activity if it is able to stimulate, or cause the stimulation of, or help cause the stimulation of the synthesis or expression of the hormone insulin. In preferred modes of practice, insulinotropic activity can be demonstrated according to assays described in U.S. Pat. Nos. 6,887,849 and 6,703,365.

In preferred embodiments, the present invention provides methodologies for synthesizing synthetic ($X^8$, $X^{10}$, $X^{35}$) GLP-1(7-36) peptides having the following formula (SEQ. ID NO. 19):

$HX^8EX^{10}TFTSDVSSYLEGQAAKEFIAWLVKX^{35}R-NH_2$ and counterparts thereof, wherein each of the symbols X at positions, 8, 10, and 35 independently denotes an achiral, optionally sterically hindered amino acid residue. Any of the $X^8$, $X^{10}$, and/or $X^{35}$ residues optionally may include side chain protecting group(s). Peptides according to this formula differ from the native GLP-1(7-36) at least in that the achiral, optionally sterically hindered $X^8$ and $X^{35}$ residues are substituted for the native amino acid residues at positions 8 and 35. The $X^{10}$ residue may be derived from the native achiral glycine or another achiral amino acid. The use of the achiral $X^8$, $X^{10}$, and $X^{35}$ amino acids not only help to stabilize the resultant peptide, but it has also now been discovered that the use of these amino acids as linker of building blocks also facilitate the synthesis route of the present invention as shown in Scheme 1 and described further below.

A particularly preferred embodiment of a ($X^8$, $X^{10}$, $X^{35}$) GLP-11(7-36) peptide that may be synthesized in accordance with principles of the present invention includes a peptide according to the formula (SEQ ID NO. 12):

HAibEGTFTSDVSSYLEGQAAKEFIAWLVKAibR-NH₂ and counterparts thereof, which preferably (as shown) is amidated at the C-terminus. This peptide uses the achiral residue of alpha-aminoisobutyric acid (shown schematically by the abbreviation Aib) as both $X^8$ and $X^{35}$, preferably has an amide at the C-terminus, uses a residue of the native G at the 10 position, and may be designated by the formula (Aib$^{8,35}$) GLP-1 (7-36)-NH₂. This notation indicates that an amino acid residue corresponding to the amino acid "Aib" appears at the 8 and 35 positions in place of the native alanine. The achiral alpha-aminoisobutric acid, also is known as methylalanine. The peptide according to SEQ ID NO. 12 is described in EP 1137667 B1. The presence of the Aib residues at the 8 and 35 positions slows metabolic degradation in the body, making this peptide much more stable in the body than the native GLP-1 (7-36) peptide.

The present invention provides improved methodologies for making GLP-1(7-36) peptides such as the (Aib$^{8,35}$)GLP-1(7-36)-NH₂. By way of example, Scheme 1 and Scheme 2 show two illustrative schemes for synthesizing GLP-1(7-36) peptides and their counterparts. Scheme 1 and Scheme 2 are believed to be particularly suitable for the scaled-up synthesis of GLP-1(7-36) peptides. Scaled-up procedures are typically performed to provide an amount of peptide useful for commercial distribution. For example the amount of peptide in a scaled-up procedure can be 500 g, or 1 kg per batch, and more typically tens of kg to hundreds of kg per batch or more. In preferred embodiments, the inventive methods can provide such improvements as reduction in processing (synthesis) time, improvements in the yield of products, improvements in product purity, and/or reduction in amount of reagents and starting materials required.

The synthesis shown in Scheme 1 uses a combination of solid and solution phase techniques to prepare the peptide product.

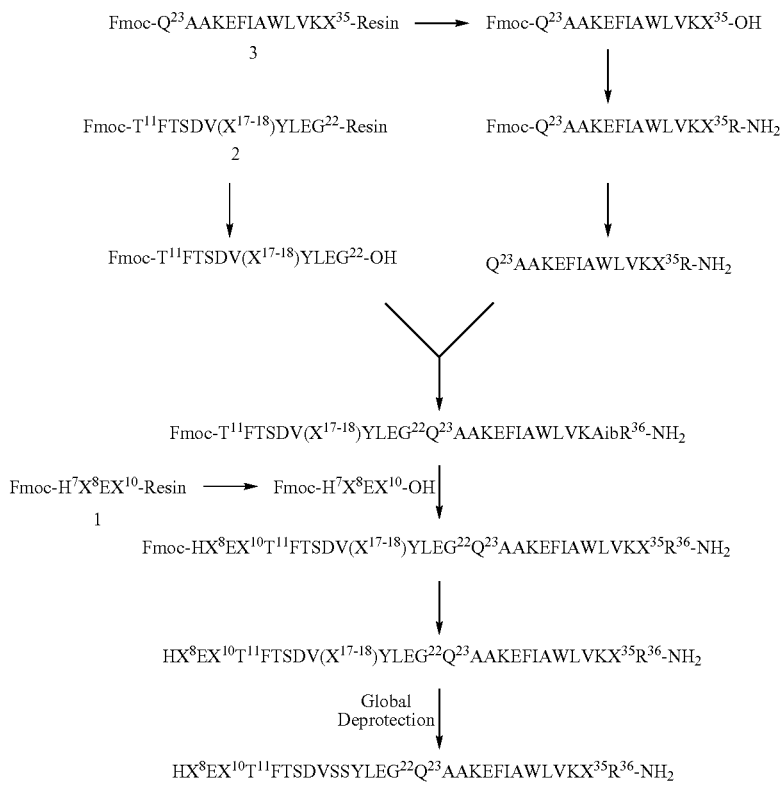

Scheme 1

As shown, Scheme 1 involves synthesizing peptide intermediate fragments 1, 2 and 3 on the solid phase. Fragment 1 is a peptide fragment including amino acid residues according to SEQ ID NO. 20:

HX⁸EX¹⁰ wherein $X^8$ and $X^{10}$ are as defined above, or is a counterpart thereof including the $X^8$ and $X^{10}$ residues. One or more of the amino acid residues may include side chain protecting groups in accordance with conventional practices. In some embodiments, the peptide fragment 12 may be resin bound via the C-terminus. This fragment optionally may bear N-terminus and/or C-terminus protection groups. Fmoc has been found to be a particularly useful N-terminus histidine protecting group with respect to solid phase synthesis and solution or solid phase coupling of the peptide fragment. Trt (trityl) has also been found to be a particularly useful N-terminus histidine protecting group with respect to solid phase synthesis and solution or solid phase coupling of the peptide fragment. Boc, CBz, DTS, Rdtc (R=Alkyl or Aryl), DBFmoc (2,7-di-t-butylFmoc), Alloc, pNZ (p-nitrobenzyl ester), Nsc ([[2-[(4-nitrophenyl)sulfonyl]ethoxy]carbonyl]-), Msc (2-methylsulfonylethoxycarbonyl), and MBz (4-methoxyCBz) are also particularly useful N-terminus histidine protecting groups with respect to solid phase synthesis and solution or solid phase coupling of the peptide fragment. [(1-[1,1'-biphenyl]-4-yl-1-methylethoxy)carbonyl], [[2,2-bis(4-nitrophenyl)ethoxy]carbonyl], [(phenylmethoxy)carbonyl], [(1,1-dimethylpropoxy)carbonyl], [[(4-methoxyphenyl)methoxy]carbonyl] are particularly useful N-terminus histidine protecting groups with respect to solid phase synthesis and solution or solid phase coupling of the peptide fragment.

Fragment 1 includes the 4 amino acid residues corresponding to the amino acids in the 7 through 10 positions of the native GLP-1(7-36) peptide, and therefore may be represented by the notation $(X^8, X^{10})GLP-1(7-10)$. In preferred embodiments, $X^8$ is Aib and $X^{10}$ is glycine according to SEQ ID NO. 21:

$$H^7 AibEG^{10}$$

or is a counterpart thereof including the Aib residue at the 10 position. The peptide fragment according to SEQ ID NO. 7 may be represented by the notation $(Aib^8)GLP-1(7-10)$ to note the substitution of Aib for the native alanine at the 8 position of the native GLP-1(7-10).

Solid phase synthesis is generally carried out in a direction from the C-terminus to the N-terminus of the fragment 1. Thus, the $X^{10}$ amino acid, which is present on the C-terminal portion of the fragment, is the first amino acid residue that is coupled to the solid phase resin support. Solid phase synthesis then proceeds by consecutively adding amino acid residues in a manner corresponding to the desired sequence. The synthesis of the peptide intermediate fragment is complete after the N-terminal residue (for example, the N-terminal histidine residue (H) has been added to the nascent peptide chain.

The selection and use of a peptide fragment according to SEQ ID NOS. 20 and 21 provides significant advantages within Scheme 1. Firstly, H (Histidine) tends to be a difficult amino acid residue to add to a growing peptide chain due, at least in part, to epimerization issues. However, fragment 1 is small enough to alleviate these concerns in large part. Yet, fragment 1 is long enough to have two chiral centers. Thus, a simple crystallization allows the fragment to be purified. If fragment 1 ended at Aib, the fragment would have only one chiral center and would be, as a consequence, more difficult to purify. Causing the achiral G to be positioned at the C-terminus also avoids racemization concerns that might otherwise be a concern if fragment 1 were to end at the C-terminus with the chiral E. In short, the selection of fragment 1 as a peptide building block makes it easier to build the fragment, purify it, and couple it to other peptide material. The fragment selection also enjoys low racemization of H. Surprisingly, H is added to this fragment with a very low level of epimerization, e.g., about 0.5% by weight in some modes of practice.

Fragment 2 is a peptide fragment including amino acid residues according to SEQ ID NO. 22:

$$T^{11}FTSD^{15}VX^{17-18}YL^{20}EG$$

wherein the residue denoted by the symbol $X^{17-18}$ is a dipeptide residue of a pseudoproline, defined further below, or is a counterpart thereof including the $X^{17-18}$ at the 17 and 18 positions. Fragment 2 includes amino acid residues generally corresponding to the amino acid residues in the 11 through 22 positions of the native GLP-1(7-36) peptide, except that the pseudoproline dipeptide residue $X^{17-18}$ is used instead of the SS (Ser-Ser) residues that occupy the corresponding 17 and 18 positions of the native GLP-1(7-36).

One or more of the amino acid residues of fragment 2 may include side chain protecting groups in accordance with conventional practices. In some embodiments, the peptide fragment 2 may be resin bound via the C-terminus. This fragment optionally may bear N-terminus and/or C-terminus protection groups. Fmoc has been found to be a particularly useful N-terminus protecting group with respect to solid phase synthesis of the peptide fragment. The peptide fragment according to SEQ ID NO. 22 may be referred to by the notation $(X^{17-18})GLP-1(11-22)$ to note the substitution of the $X^{17-18}$ pseudoproline residue for the Ser-Ser residue at the 17 and 18 positions.

As used in the practice of the present invention, the term pseudoproline refers to a dipeptide that includes a residue of a hydroxyl functional amino acid such as Ser or Thr in which the hydroxyl functional side chain is protected as a proline-like, TFA labile, oxazolidine ring between the alpha-amino and the side chain hydroxyl. As a consequence of the oxazolidine ring, the dipeptide functions as a reversible proline mimetic.

Generally, a typical pseudoproline residue as incorporated into a peptide may be represented by the formula

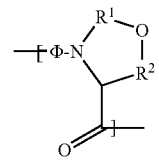

wherein Φ represents the residue of any amino acid and each of $R^1$ and $R^2$ is independently a suitable divalent linking moiety. Often, $R^1$ is a divalent moiety of the formula

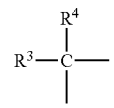

wherein each of $R^3$ and $R^4$ is independently a monovalent moiety such as H, or lower alkyl such as methyl. $R^3$ and $R^4$ also may be co-members of a ring structure. Desirably, each of $R^3$ and $R^4$ is methyl. In the case of an oxazolidinine ring-protected Ser, $R^2$ is the divalent moiety $CH_2$, while in the case of Thr, $R^2$ is the divalent moiety $(CH_3)CH$.

The term "lower alkyl" refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

During de-protection, the $R^1$ moiety is cleaved to provide a dipeptide residue according to the following formula:

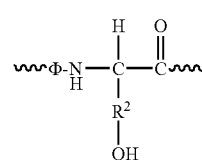

wherein Φ and R² are as defined above. As applied to fragment 2, the pseudoproline residue preferably corresponds to a Ser-Ser residue in which the Ser that is more proximal to the C-terminus is protected with the oxazolidine ring and has the following structure:

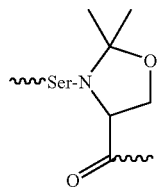

The hydroxyl-bearing side-chain of the Ser closer to the N-terminus is protected, such as by a t-Bu protection group. When the protecting oxazolidine ring structure and t-Bu are cleaved, the Ser-Ser residue results.

The use of such a proline mimetic as a building block in the synthesis of fragment 2 provides significant advantages in the context of the present invention. Firstly, the solid phase synthesis of fragment 2 is eased tremendously. When the pseudoproline is not used in the course of solid phase synthesis of fragment 2, there can be significant problems with Fmoc removals from residues 13 through 11. It is believed that this difficulty may be due to beta sheet formation. Use of the pseudoproline makes these Fmoc removals much easier by, it is believed, reducing the degree of beta sheet formation. Secondly, the subsequent solution phase coupling of fragment 2 to fragment 3, as depicted above in Scheme 1, is greatly eased. In the absence of the pseudoproline residue, the solubility of the fragment in typical solution phase coupling solvents is very poor. The pseudoproline enhances the solubility characteristics of fragment 2, (and longer fragments incorporating fragment 2), easing the subsequent solution phase coupling of fragment 1.

Solid phase synthesis is generally carried out in a direction from the C-terminus to the N-terminus of the fragment 1. Thus, the G amino acid, which is present on the C-terminal portion of the fragment, is the first amino acid residue that is coupled to the solid phase resin support. Solid phase synthesis then proceeds by consecutively adding amino acid residues in a manner corresponding to the desired sequence. However, the $X^{17-18}$ pseudoproline dipeptide is added to the growing chain in a position corresponding to the 17 and 18 positions of GLP-1(7-36) instead of consecutively adding a pair of the native Ser residues at the 17 and 18 positions. The synthesis of the peptide intermediate fragment is complete after the N-terminal residue (for example, the N-terminal threonine residue (T) has been added to the nascent peptide chain).

Fragment 3 is a peptide fragment, or counterpart thereof, including amino acid residues according to SEQ ID NO. 23:

$Q^{23}AA^{25}KEFIA^{30}WLVKX^{35}$ wherein $X^{35}$ is as defined above, or is a counterpart thereof including the $X^{35}$ residue. One or more of the amino acid residues may include side chain protecting groups in accordance with conventional practices. Fragment 3 includes the amino acid residues corresponding to the amino acids in the 23 through 35 positions of the native GLP-1(7-36) peptide, except that $X^{35}$ is at the 35 position in place of the native amino acid at that position. Fragment 3 may be represented by the notation $(X^{35})$GLP-1(23-35).

In some embodiments, the peptide fragment 3 may be resin bound via the C-terminus. This fragment optionally may bear side chain, N-terminus and/or C-terminus protection groups. Fmoc has been found to be a particularly useful N-terminus protecting group with respect to solid phase synthesis of the peptide fragment.

In preferred embodiments, $X^{35}$ is Aib according to SEQ ID NO. 24:

$Q^{23}AA^{25}KEFIA^{30}WLVKAib^{35}$ or a counterpart thereof including the Aib at the 35 position. The peptide fragment according to SEQ ID NO. 10 may be represented by the notation $(Aib^{35})$GLP-1(23-35) to note the substitution of Aib for the native amino acid at the 35 position of the native GLP-1(7-36).

Note that fragment 3 according to SEQ ID NOS. 23 and 24 does not yet include the R (Arg) residue in the 36 position at the C terminus. The Arg is subsequently coupled to the C terminus of fragment 3 in the solution phase, preferably using Arg without side chain protection. This strategy provides significant advantages within Scheme 1, because it avoids undesirable side reactions that tend to occur as a consequence of using protected Arg. For instance, upon de-protection of protected Arg, by-products of the de-protection may tend to react with other constituents of the peptide, e.g., tryptophan. This reduces the amount of desired peptide available in the crude for purification.

Solid phase synthesis is generally carried out in a direction from the C-terminus to the N-terminus of the fragment 3. Thus, the $X^{35}$ amino acid, which is present on the C-terminal portion of the fragment, is the first amino acid residue that is coupled to the solid phase resin support. Solid phase synthesis then proceeds by consecutively adding amino acid residues in a manner corresponding to the desired sequence. The synthesis of the peptide intermediate fragment is complete after the N-terminal residue (for example, the N-terminal glutamine residue (Q) has been added to the nascent peptide chain. Any of the amino acids used in the synthesis of fragment 3 may include side chain protection in accordance with conventional practices.

Due to steric hindrance proximal to the $X^{35}$-loaded support resin, the coupling of lysine (34) and valine (33) onto the growing peptide chain can be problematic. Even with an excess of amino acid, it is difficult to force these coupling reactions to completion. Solvent choice and/or end-capping can help to alleviate this problem. It has been found that the nature of the coupling solvent can impact the degree to which the coupling goes to completion. In one set of experiments, for example, coupling reactions were carried out in a 3:1 NMP/DCM, 1:1 NMP/DCM, 1:1 DMF/DCM, and 3:1 DMF/DCM. The ratios in these solvent combinations are on a volume basis. NMP refers to N-methylpyrrolidone, DCM refers to dichloromethane, and DMF refers to dimethylformamide. It was found that the coupling reactions proceeded farther to completion when using 1:1 DMF/DCM.

End-capping after each of the lysine and valine couplings can also be used to prevent unreacted resin-supported material from proceeding in further coupling reactions. The end-capped material is more easily removed during purification if desired. Conventional end-capping techniques may be used.

Continuing to refer to Scheme 1, fragments 1, 2, and 3, along with Arg, are assembled to complete the desired peptide.

Scheme 1 shows that Arg is added to the C-terminus of fragment 3 in the solution phase to yield the intermediate fragment 3'. Preferably, the Arg added to the peptide fragment in this way does not include side chain protection. Fragment 2 is then added to fragment 3' produce a larger, intermediate fragment incorporating amino acid residues according to SEQ ID NO. 25 in which the Ser-Ser at the 17 and 18 positions is still in the protected pseudoproline form:

TFTSD$^{15}$VX$^{17-18}$YL$^{20}$EG Q$^{23}$AA$^{25}$KEFIA$^{30}$WLVKX$^{35}$R-NH$_2$ wherein $X^{35}$ is as defined above and is preferably Aib, and $X^{17-18}$ is a pseudoproline dipeptide residue as defined above. The intermediate fragment may be designated by the notation $(X^{17-18}, X^{35})$ GLP-1(11-36). To the extent that the amino acids bear side chain protection, this protection desirably is maintained through this step.

Scheme 1 further shows that fragment 1 is then added to this intermediate fragment in solution to produce the desired peptide (SEQ ID NO. 26):

HX$^8$EX$^{10}$TFTSDVX$^{17-18}$YLEGQAAKEFIAWLVKX$^{35}$R-NH$_2$

In alternative preferred embodiments, the present invention provides methodologies for synthesizing synthetic $(X^8, X^{10}, X^{35})$GLP-1 (7-36) peptides having the following formula (SEQ. ID NO. 19):

HX$^8$EX$^{10}$TFTSDVSSYLEGQAAKEFIAWLVKX$^{35}$R-NH$_2$ and counterparts thereof, wherein each of the symbols X at positions, 8, 10, and 35 independently denotes an achiral, optionally sterically hindered amino acid residue. Any of the $X^8$, $X^{10}$, and/or $X^{35}$ residues optionally may include side chain protecting group(s). Peptides according to this formula differ from the native GLP-1(7-36) at least in that the achiral, optionally sterically hindered $X^8$ and $X^{35}$ residues are substituted for the native amino acid residues at positions 8 and 35. The $X^{10}$ residue may be derived from the native achiral glycine or another achiral amino acid. The use of the achiral $X^8$, $X^{10}$, and $X^{35}$ amino acids not only help to stabilize the resultant peptide, but it has also now been discovered that the use of these amino acids as building blocks also facilitate the facile synthesis route of the present invention as shown in Scheme 1 and described further below.

A particularly preferred embodiment of a $(X^8, X^{10}, X^{35})$ GLP-11 (7-36) peptide that may be synthesized in accordance with principles of the present invention includes a peptide according to the formula (SEQ ID NO. 12):

HAibEGTFTSDVSSYLEGQAAKEFIAWLVKAibR-NH$_2$ and counterparts thereof, which preferably (as shown) is amidated at the C-terminus. This peptide uses the achiral residue of alpha-aminoisobutyric acid (shown schematically by the abbreviation Aib) as both $X^8$ and $X^{35}$, preferably has an amide at the C-terminus, uses a residue of the native G at the 10 position, and may be designated by the formula (Aib$^{8,35}$) GLP-1(7-36)-NH$_2$. This notation indicates that an amino acid residue corresponding to the amino acid "Aib" appears at the 8 and 35 positions in place of the native alanine. The achiral alpha-aminoisobutric acid, also is known as methylalanine. The peptide according to SEQ ID NO. 4 is described in EP 1137667 B1. The presence of the Aib residues at the 8 and 35 positions slows metabolic degradation in the body, making this peptide much more stable in the body than the native GLP-1(7-36) peptide.

The synthesis shown in Scheme 2 uses a combination of solid and solution phase techniques to prepare the peptide product.

Scheme 2

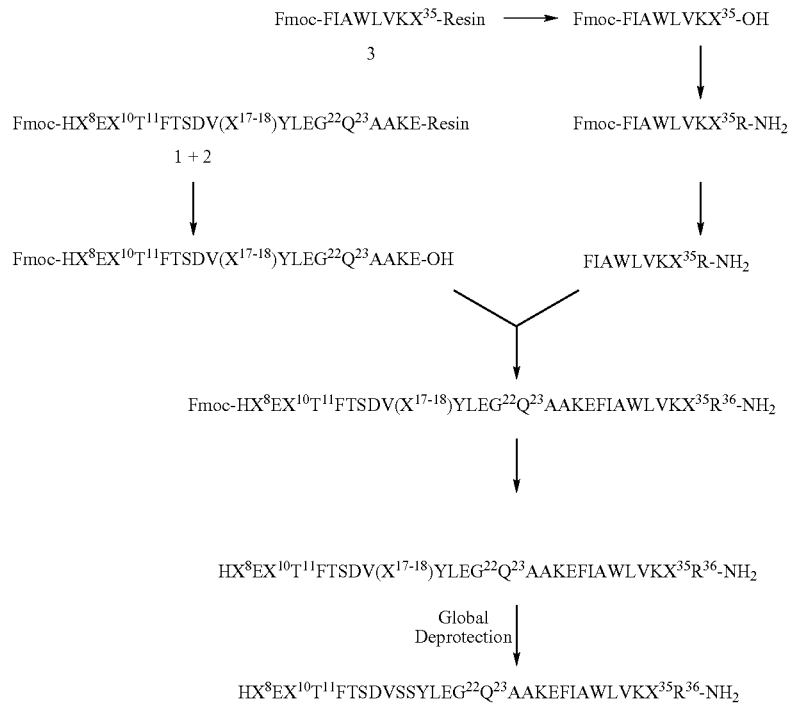

As shown, Scheme 2 involves synthesizing peptide intermediate fragments 1+2 and 3 on the solid phase. Fragment 1+2 is a peptide fragment including amino acid residues according to SEQ ID NO. 27:

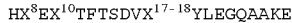

wherein $X^8$ and $X^{10}$ are as defined above, or is a counterpart thereof including the $X^8$ and $X^{10}$ residues. One or more of the amino acid residues may include side chain protecting groups in accordance with conventional practices. In some embodiments, the peptide fragment 12 may be resin bound via the C-terminus. This fragment optionally may bear N-terminus and/or C-terminus protection groups. Fmoc has been found to be a particularly useful N-terminus histidine protecting group with respect to solid phase synthesis and solution or solid phase coupling of the peptide fragment. Trt (trityl) has also been found to be a particularly useful N-terminus histidine protecting group with respect to solid phase synthesis and solution or solid phase coupling of the peptide fragment. Boc (t-butyloxycarbonyl), CBz (benzyloxycarbonyl or Z), Dts (dithiasuccinoyl), Rdtc (R=Alkyl or Aryl, dtc=dithiocarbamate), DBFmoc (2,7-di-t-butylFmoc or 1,7-di-t-butylfluoren-9-ylmethoxycarbonyl), Alloc (allyloxycarbonyl), pNZ (p-nitrobenzyloxycarbonyl), Nsc ([[2-[(4-nitrophenyl)sulfonyl]ethoxy]carbonyl]), Msc (2-methylsulfonylethoxycarbonyl), and MBz (4-methoxyCBz) are also particularly useful N-terminus histidine protecting groups with respect to solid phase synthesis and solution or solid phase coupling of the peptide fragment. Bpoc [(1-[1,1'-biphenyl]-4-yl-1-methylethoxy)carbonyl], Bnpeoc [[2,2-bis(4-nitrophenyl)ethoxy]carbonyl], CBz [(phenylmethoxy)carbonyl], Aoc [(1,1-dimethylpropoxy)carbonyl], and Moz [[(4-methoxyphenyl)methoxy]carbonyl] are particularly useful N-terminus histidine protecting groups with respect to solid phase synthesis and solution or solid phase coupling of the peptide fragment.

Fragment 1+2 includes the 20 amino acid residues corresponding to the amino acids in the 7 through 27 positions of the native GLP-1(7-36) peptide, and therefore may be represented by the notation $(X^8, X^{10}, X^{17-18})$GLP-1(7-27). In preferred embodiments, $X^8$ is Aib and $X^{10}$ is glycine according to SEQ ID NO. 28:

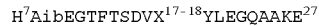

or is a counterpart thereof including the Aib residue at the 10 position. The peptide fragment according to SEQ ID NO. 28 may be represented by the notation $(Aib^8, X^{17-18})$GLP-1 (7-27) to note the substitution of Aib for the native alanine at the 8 position of the native GLP-1 (7-36). The residue denoted by the symbol $X^{17-18}$ is a dipeptide residue of a pseudoproline, defined further below, or is a counterpart thereof including the $X^{17-18}$ at the 17 and 18 positions.

Fragment 2 includes amino acid residues generally corresponding to the amino acid residues in the 11 through 27 positions of the native GLP-1(7-36) peptide, except that the pseudoproline dipeptide residue $X^{17-18}$ is used instead of the SS (Ser-Ser) residues that occupy the corresponding 17 and 18 positions of the native GLP-1(7-36).

One or more of the amino acid residues of fragment 2 may include side chain protecting groups in accordance with conventional practices. In some embodiments, the peptide fragment 2 may be resin bound via the C-terminus. This fragment optionally may bear N-terminus and/or C-terminus protection groups. Fmoc has been found to be a particularly useful N-terminus protecting group with respect to solid phase synthesis of the peptide fragment. The peptide fragment 2 according to SEQ ID NO. 29

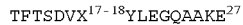

may be referred to by the notation $(X^{17-18})$GLP-1(11-27) to note the substitution of the $X^{17-18}$ pseudoproline residue for the Ser-Ser residue at the 17 and 18 positions.

As used in the practice of the present invention, the term pseudoproline refers to a dipeptide that includes a residue of a hydroxyl functional amino acid such as Ser or Thr in which the hydroxyl functional side chain is protected as a proline-like, TFA labile, oxazolidine ring between the alpha-amino and the side chain hydroxyl. As a consequence of the oxazolidine ring, the dipeptide functions as a reversible proline mimetic.

The use of such a proline mimetic as a building block in the synthesis of fragment 1+2 provides significant advantages in the context of the present invention. Firstly, the solid phase synthesis of fragment 2 is eased tremendously. When the pseudoproline is not used in the course of solid phase synthesis of fragment 2, there can be significant problems with Fmoc removals from residues 13 through 11. It is believed that this difficulty may be due to beta sheet formation. Use of the pseudoproline makes these Fmoc removals much easier by, it is believed, reducing the degree of beta sheet formation. In the absence of the pseudoproline residue, the solubility of the fragment in typical solution phase coupling solvents is very poor. The pseudoproline enhances the solubility characteristics of fragment 2, (and longer fragments incorporating fragment 2, such as fragment 1+2), easing the subsequent solution phase coupling of fragment 1+2.

Solid phase synthesis is generally carried out in a direction from the C-terminus to the N-terminus of the fragment 1+2. Thus, the $E^{27}$ amino acid, which is present on the C-terminal portion of the fragment, is the first amino acid residue that is coupled to the solid phase resin support. Solid phase synthesis then proceeds by consecutively adding amino acid residues in a manner corresponding to the desired sequence. However, the $X^{17-18}$ pseudoproline dipeptide is added to the growing chain in a position corresponding to the 17 and 18 positions of GLP-1(7-36) instead of consecutively adding a pair of the native Ser residues at the 17 and 18 positions. The synthesis of the peptide intermediate fragment is complete after the N-terminal residue (for example, the N-terminal threonine residue (T) has been added to the nascent peptide chain.

Fragment 3 is a peptide fragment, or counterpart thereof, including amino acid residues according to SEQ ID NO. 30:

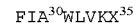

wherein $X^{35}$ is as defined above, or is a counterpart thereof including the $X^{35}$ residue. One or more of the amino acid residues may include side chain protecting groups in accordance with conventional practices. Fragment 3 includes the amino acid residues corresponding to the amino acids in the 28 through 35 positions of the native GLP-1(7-36) peptide, except that $X^{35}$ is at the 35 position in place of the native amino acid at that position. Fragment 3 according to SEQ ID NO. 30 may be represented by the notation $(X^{35})$GLP-1 (28-35).

In some embodiments, the peptide fragment 3 may be resin bound via the C-terminus. This fragment optionally may bear side chain, N-terminus and/or C-terminus protection groups.

Fmoc has been found to be a particularly useful N-terminus protecting group with respect to solid phase synthesis of the peptide fragment.

In preferred embodiments, $X^{35}$ is Aib according to SEQ ID NO. 31:

or a counterpart thereof including the Aib at the 35 position. The peptide fragment according to SEQ ID NO. 31 may be represented by the notation $(Aib^{35})GLP-1(28-35)$ to note the substitution of Aib for the native amino acid at the 35 position of the native GLP-1 (7-36).

Note that fragment 3 according to SEQ ID NOS. 30 and 31 does not yet include the R (Arg) residue in the 36 position at the C terminus. The Arg is subsequently coupled to the C terminus of fragment 3 in the solution phase, preferably using Arg without side chain protection. This strategy provides significant advantages within Scheme 2, because it avoids undesirable side reactions that tend to occur as a consequence of using protected Arg. For instance, upon de-protection of protected Arg, by-products of the de-protection may tend to react with other constituents of the peptide, e.g., tryptophan. This reduces the amount of desired peptide available in the crude for purification.

Fragment 3' according to SEQ ID NO. 32 is a peptide fragment, or counterpart thereof, including amino acid residues according to SEQ ID NO. 32:

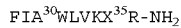

wherein $X^{35}$ is as defined above, or is a counterpart thereof including the $X^{35}$ residue. One or more of the amino acid residues may include side chain protecting groups in accordance with conventional practices. Fragment 3' includes the amino acid residues corresponding to the amino acids in the 28 through 36 positions of the native GLP-1 (7-36) peptide, except that $X^{35}$ is at the 35 position in place of the native amino acid at that position. Fragment 3' according to SEQ ID NO. 32 may be represented by the notation $(X^{35})GLP-1(28-36)$.

Solid phase synthesis is generally carried out in a direction from the C-terminus to the N-terminus of the fragment 3. Thus, the $X^{35}$ amino acid, which is present on the C-terminal portion of the fragment, is the first amino acid residue that is coupled to the solid phase resin support. Solid phase synthesis then proceeds by consecutively adding amino acid residues in a manner corresponding to the desired sequence. The synthesis of the peptide intermediate fragment is complete after the N-terminal residue (for example, the N-terminal glutamine residue (Q) has been added to the nascent peptide chain. Any of the amino acids used in the synthesis of fragment 3 may include side chain protection in accordance with conventional practices.

Due to steric hindrance proximal to the $X^{35}$-loaded support resin, the coupling of lysine (34) and valine (33) onto the growing peptide chain can be problematic. Even with an excess of amino acid, it is difficult to force these coupling reactions to completion. Solvent choice and/or end-capping can help to alleviate this problem. It has been found that the nature of the coupling solvent can impact the degree to which the coupling goes to completion. In one set of experiments, for example, coupling reactions were carried out in a 3:1 NMP/DCM, 1:1 NMP/DCM, 1:1 DMF/DCM, and 3:1 DMF/DCM. The ratios in these solvent combinations are on a volume basis. NMP refers to N-methylpyrrolidone, DCM refers to dichloromethane, and DMF refers to dimethylformamide. It was found that the coupling reactions proceeded farther to completion when using 1:1 DMF/DCM.

End-capping after each of the lysine and valine couplings can also be used to prevent unreacted resin-supported material from proceeding in further coupling reactions. The end-capped material is more easily removed during purification if desired. Conventional end-capping techniques may be used.

Continuing to refer to Scheme 2, fragments 1, 2, and 3, along with Arg, are assembled to complete the desired peptide.

Scheme 2 shows that Arg is added to the C-terminus of fragment 3 in the solution phase to yield the intermediate fragment 3' according to SEQ ID NO. 32

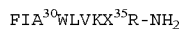

wherein $X^{35}$ is as defined above and is preferably Aib. Preferably, the Arg added to the peptide fragment in this way does not include side chain protection.

Fragment 1+2, in which the Ser-Ser at the 17 and 18 positions is still in the protected pseudoproline form, according to SEQ ID NO. 27:

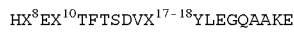

which may be designated by the notation $(X^{17-18}, X^{35})$ GLP-1(11-36), is then coupled to fragment 3' in the solution phase. To the extent that the other amino acids bear side chain protection, this protection desirably is maintained through this step. The desired peptide, incorporating fragments 1+2+3, according to SEQ ID NO. 26:

is then formed, wherein, in a preferred embodiment, $X^8$ is Aib, $X^{10}$ is the native G, and $X^{17-18}$ is a pseudoproline dipeptide residue as defined above.

In carrying out the reaction schemes of Schemes 1 and 2, solid phase and solution phase syntheses may be carried out by standard methods known in the industry. In representative modes of practice, peptides are synthesized in the solid phase using chemistry by which amino acids are added from the C-terminus to the N-terminus. Thus, the amino acid or peptide group proximal to the C-terminus of a particular fragment is the first to be added to the resin. This occurs by reacting the C-terminus functionality of the amino acid or peptide group with complementary functionality on the resin support. The N-terminus side of the amino acid or peptide group is masked to prevent undesired side reactions. The amino acid or peptide group desirably also includes side chain protection as well. Then successive amino acids or peptide groups are attached to the support-bound peptide material until the peptide of interest is formed. Most of these also include side chain protection in accordance with conventional practices. With each successive coupling, the masking group at the N-terminus end of the resin bound peptide material is removed. This is then reacted with the C-terminus of the next amino acid whose N-terminus is masked. The product of solid phase synthesis is thus a peptide bound to a resin support.

In order to minimize the influence of quality differences of the fragments such as amount of residual solvents, residual dibenzofulvene or variation in assay or quality, the concept was to use the total peptide assay of each fragment as a basis for calculation. As most of the peptidic impurities of Fragment 2 have more or less the same weight as Fragment 2 and react as Fragment 2 and most of the peptidic impurities of Fragment 3' have more or less the same weight as Fragment 3' and react as Fragment 3', the total peptide concept allows for adjusting the ratio of the reactants. For calculation purposes, dibenzofulvene is generally not taken into account as it is not a peptide and regarding mass massively overestimated by its UV-signal (same response factor as the fragments). Thus, the total peptide assay of the fragments can be calculated as follows: a) assay (%-mm)*(100–amount of dibenzofulvene in %-area)/[quality (%-area)] or b) sum of main component and all peptidic impurities in %-(w/w)–dibenzofulvene in %-(mm) (same response factor as peptide).

Any type of support suitable in the practice of solid phase peptide synthesis can be used. In preferred embodiments, the support comprises a resin that can be made from one or more polymers, copolymers or combinations of polymers such as polyamide, polysulfamide, substituted polyethylenes, polyethyleneglycol, phenolic resins, polysaccharides, or polystyrene. The polymer support can also be any solid that is sufficiently insoluble and inert to solvents used in peptide synthesis. The solid support typically includes a linking moiety to which the growing peptide is coupled during synthesis and which can be cleaved under desired conditions to release the peptide from the support. Suitable solid supports can have linkers that are photo-cleavable, TFA-cleavable, HF-cleavable, fluoride ion-cleavable, reductively-cleavable; Pd(O)-cleavable; nucleophilically-cleavable; or radically-cleavable. Preferred linking moieties are cleavable under conditions such that the side-chain groups of the cleaved peptide are still substantially globally protected.

In one preferred method of synthesis, the peptide intermediate fragments synthesized on an acid sensitive solid support that includes trityl groups, and more preferably on a resin that includes trityl groups having pendent chlorine groups, for example a 2-chlorotrityl chloride (2-CTC) resin (Barlos et al. (1989) Tetrahedron Letters 30(30):3943-3946). Examples also include trityl chloride resin, 4-methyltrityl chloride resin, 4-methoxytrityl chloride resin, 4-aminobutan-1-ol 2-chlorotrityl resin, 4-aminomethylbenzoyl 2-chlorotrityl resin, 3-aminopropan-1-ol 2-chlorotrityl resin, bromoacetic acid 2-chlorotrityl resin, cyanoacetic acid 2-chlorotrityl resin, 4-cyanobenzoic acid 2-chlorotrityl resin, glicinol 2-chlorotrityl resin, propionic 2-chlorotrityl resin, ethyleneglycol 2-chlorotrityl resin, N-Fmoc hydroxylamine 2-chlorotrityl resin, hydrazine 2-chlorotrityl resin. Some preferred solid supports include polystyrene, which can be copolymerized with divinylbenzene, to form support material to which the reactive groups are anchored.

Other resins that are used in solid phase synthesis include "Wang" resins, which comprise a copolymer of styrene and divinylbenzene with 4-hydroxymethylphenyloxymethyl anchoring groups (Wang, S. S. 1973, J. Am. Chem. Soc.), and 4-hydroxymethyl-3-methoxyphenoxybutyric acid resin (Richter et al. (1994), Tetrahedron Letters 35(27):4705-4706). The Wang, 2-chlorotrityl chloride, and 4-hydroxymethyl-3-methoxyphenoxy butyric acid resins can be purchased from, for example, Calbiochem-Novabiochem Corp., San Diego, Calif.

In order to prepare a resin for solid phase synthesis, the resin can be pre-washed in suitable solvent(s). For example, a solid phase resin such as a 2-CTC resin is added to a peptide chamber and pre-washed with a suitable solvent. The pre-wash solvent may be chosen based on the type of solvent (or mixture of solvents) that is used in the coupling reaction, or vice versa. Solvents that are suitable for washing, and also the subsequent coupling reaction include dichloromethane (DCM), dichloroethane (DCE), dimethylformamide (DMF), and the like, as well as mixtures of these reagents. Other useful solvents include DMSO, pyridine, chloroform, dioxane, tetrahydrofuran, ethyl acetate, N-methylpyrrolidone, and mixtures thereof. In some cases coupling can be performed in a binary solvent system, such as a mixture of DMF and DCM at a volume ratio in the range of 9:1 to 1:9, more commonly 4:1 to 1:4.

The syntheses of the present invention preferably are carried out in the presence of appropriate protecting groups unless otherwise noted. The nature and use of protecting groups is well known in the art. Generally, a suitable protecting group is any sort of group that that can help prevent the atom or moiety to which it is attached, e.g., oxygen or nitrogen, from participating in undesired reactions during processing and synthesis. Protecting groups include side chain protecting groups and amino- or N-terminal protecting groups. Protecting groups can also prevent reaction or bonding of carboxylic acids, thiols and the like.

A side chain protecting group refers to a chemical moiety coupled to the side chain (i.e., R group in the general amino acid formula $H_2N$—$C(R)(H)$—$COOH$) of an amino acid that helps to prevent a portion of the side chain from reacting with chemicals used in steps of peptide synthesis, processing, etc. The choice of a side chain-protecting group can depend on various factors, for example, type of synthesis performed, processing to which the peptide will be subjected, and the desired intermediate product or final product. The nature of the side chain protecting group also depends on the nature of the amino acid itself. Generally, a side chain protecting group is chosen that is not removed during deprotection of the α-amino groups during the solid phase synthesis. Therefore the α-amino protecting group and the side chain protecting group are typically not the same.

In some cases, and depending on the type of reagents used in solid phase synthesis and other peptide processing, an amino acid may not require the presence of a side-chain protecting group. Such amino acids typically do not include a reactive oxygen, nitrogen, or other reactive moiety in the side chain.

Examples of side chain protecting groups include acetyl (Ac), benzoyl (Bz), tert-butyl, triphenylmethyl (trityl), tetrahydropyranyl, benzyl ether (Bzl) and 2,6-dichlorobenzyl (DCB), t-butoxycarbonyl (Boc), nitro, p-toluenesulfonyl (Tos), adamantyloxycarbonyl, xanthyl (Xan), benzyl, 2,6-dichlorobenzyl, methyl, ethyl and t-butyl ester, benzyloxycarbonyl (cBz or Z), 2-chlorobenzyloxycarbonyl (2-Cl—Z), t-amyloxycarbonyl(Aoc), and aromatic or aliphatic urethan-type protecting groups. photolabile groups such as nitroveratryloxycarbonyl (NVOC); and fluoride labile groups such as 2-trimethylsilylethoxycarbonyl (TEOC).

Preferred side chain protecting groups for amino acids commonly used to synthesize GLP-1 peptides in the practice of the present invention are shown in the following Table A:

TABLE A

| Amino Acid | Side Chain Protecting group(s) |
|---|---|
| Aib | None |
| Ala | None |
| Arg | None |
| Asp | t-butyl ester (OtBu) |
| Gln | trityl (trt) |
| Glu | OtBu |
| Gly | None |
| His | trityl (trt) |

TABLE A-continued

| Amino Acid | Side Chain Protecting group(s) |
| --- | --- |
| Ile | None |
| Leu | None |
| Lys | t-butyloxycarbonyl (Boc) |
| Phe | None |
| Ser | t-butyl (tBu) |
| $X^{17-18}$ (corresponding to Ser-Ser) | oxazolidine ring between alpha nitrogen and OH of Ser closer to the C-terminus; tBu on other Ser |
| Thr | tBu |
| Trp | Boc |
| Tyr | tBu |
| Val | None |

An amino-terminal protecting group includes a chemical moiety coupled to the alpha amino group of an amino acid. Typically, the amino-terminal protecting group is removed in a deprotection reaction prior to the addition of the next amino acid to be added to the growing peptide chain, but can be maintained when the peptide is cleaved from the support. The choice of an amino terminal protecting group can depend on various factors, for example, type of synthesis performed and the desired intermediate product or final product.

Examples of amino-terminal protecting groups include (1) acyl-type protecting groups, such as formyl, acrylyl (Acr), benzoyl (Bz) and acetyl (Ac); (2) aromatic urethane-type protecting groups, such as benzyloxycarbonyl (Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (Boc), diisopropylmethoxycarbonyl, isopropyloxycarbonyl, ethoxycarbonyl, allyloxycarbonyl; (4) cycloalkyl urethan-type protecting groups, such as 9-fluorenyl-methyloxycarbonyl (Fmoc), cyclopentyloxycarbonyl, adamantyloxycarbonyl, and cyclohexyloxycarbonyl; and (5) thiourethan-type protecting groups, such as phenylthiocarbonyl. Preferred protecting groups include 9-fluorenyl-methyloxycarbonyl (Fmoc), 2-(4-biphenylyl)-propyl(2)oxycarbonyl (Bpoc), 2-phenylpropyl(2)-oxycarbonyl (Poc) and t-butyloxycarbonyl (Boc).

Fmoc or Fmoc-like chemistry is highly preferred for solid phase peptide synthesis, inasmuch as cleaving the resultant peptide in a protected state is relatively straightforward to carry out using mildly acidic cleaving agents. This kind of cleaving reaction is relatively clean in terms of resultant by-products, impurities, etc., making it technically and economically feasible to recover peptide on a large scale basis from both the swelling and shrinking washes, enhancing yield. As used herein, "large scale" with respect to peptide synthesis generally includes the synthesis of peptides in the range of at least 500 g, more preferably at least 2 kg per batch. Large-scale synthesis is typically performed in large reaction vessels, such as steel reaction vessels, that can accommodate quantities of reagents such as resins, solvents, amino acids, chemicals for coupling, and deprotection reactions, that are sized to allow for production of peptides in the kilogram to metric ton range.

Additionally, the Fmoc protecting group can be selectively cleaved from a peptide relative to the side chain protecting groups so that the side chain protection are left in place when the Fmoc is cleaved. This kind of selectivity is important during amino acid coupling to minimize side chain reactions. Additionally, the side chain protecting groups can be selectively cleaved to remove them relative to the Fmoc, leaving the Fmoc in place. This latter selectivity is very advantageously relied upon during purification schemes described further below.

The solid phase coupling reaction can be performed in the presence of one or more compounds that enhance or improve the coupling reaction. Compounds that can increase the rate of reaction and reduce the rate of side reactions include phosphonium and uronium salts that can, in the presence of a tertiary base, for example, diisopropylethylamine (DIEA) and triethylamine (TEA), convert protected amino acids into activated species (for example, BOP, PyBOP, HBTU, and TBTU, which generate HOBt esters, and DEPBT which generates an HOOBt ester). Other reagents help prevent racemization by providing a protecting reagent. These reagents include carbodiimides (for example, DCC or WSCDI) with an added auxiliary nucleophile (for example, 1-hydroxy-benzotriazole (HOBt), 1-hydroxy-azabenzotriazole (HOAt), or HOSu). The mixed anhydride method, using isobutyl chloroformate, with or without an added auxiliary nucleophile, may also be utilized, as can the azide method, due to the low racemization associated with it. These types of compounds can also increase the rate of carbodiimide-mediated couplings, as well as prevent dehydration of Asn and Gln residues.

After the coupling is determined to be complete, the coupling reaction mixture is washed with a solvent, and the coupling cycle is repeated for each of the subsequent amino acid residues of the peptide material. In order to couple the next amino acid, removal of the N-terminal protecting group (for example, an Fmoc group) from the resin-bound material is typically accomplished by treatment with a reagent that includes 20-50% (on a weight basis) piperidine in a solvent, such as N-methylpyrrolidone (NMP) or dimethylformamide (DMF). After removal of the Fmoc protecting group, several washes are typically performed to remove residual piperidine and Fmoc by-products (such as dibenzofulvene and its piperidine adduct).

The subsequent amino acids can be utilized at a stoichiometric excess of amino acids in relation to the loading factor of peptide material on the resin support. Generally, the amount of amino acids used in the coupling step is at least equivalent to the loading factor of the first amino acid on the resin (1 equivalent or more). Preferably the amount of amino acids used in the coupling step is at least 1.3 equivalent (0.3 excess) or more, and most preferably about 1.5 equivalent (0.5 excess) or more. In some cases, for example, the coupling step utilizes an amount equivalent of amino acids in the range between 1 and 3.

Following the final coupling cycle, the resin is washed with a solvent such as NMP, and then washed with an inert second solvent such as DCM. In order to remove the synthesized peptide material from the resin, a cleaving treatment is carried out in a manner such that the cleaved peptide material still bears sufficient side chain and terminus protecting groups. Leaving the protective groups in place helps to prevent undesirable coupling or other undesirable reactions of peptide fragments during or after resin cleavage. In the case when Fmoc or similar chemistry is used to synthesize the peptide, protected cleavage may be accomplished in any desired fashion such as by using a relatively weak acid reagent such as acetic acid or dilute TFA in a solvent such as DCM. The use of 0.5 to 10 weight percent, preferably 1 to 3 weight percent TFA in DCM is typical. See, e.g., U.S. Pat. No. 6,281,335.

Steps of cleaving the peptide intermediate fragment from the solid phase resin can proceed along the lines of an exemplary process as follows. However, any suitable process that effectively cleaves the peptide intermediate fragment from the resin can be used. For example, approximately 5 to 20, preferably about 10 volumes of a solvent containing an acidic cleaving reagent is added to the vessel containing the resin-bound peptide material. The resin, typically in the form of beads, is immersed in the reagent as a consequence. The cleaving reaction occurs as the liquid contents are agitated at a suitable temperature for a suitable time period. Agitation helps prevent the beads from clumping. Suitable time and temperature conditions will depend upon factors such as the acid reagent being used, the nature of the peptide, the nature of the resin, and the like. As general guidelines, stirring at from about −15° C. to about 5° C., preferably from about −10° C. to about 0° C. for about 5 minutes to two hours, preferably about 25 minutes to about 45 minutes would be suitable. Cleaving time may be in the range of from about 10 minutes to about 2 hours or even as much as a day. Cleaving is desirably carried out in such a chilled temperature range to accommodate a reaction exotherm that might typically occur during the reaction. In addition, the lower temperature of the cleavage reaction prevents acid sensitive side chain protecting groups, such as trt groups, from being removed at this stage.

At the end of the cleaving treatment, the reaction is quenched. This may be achieved, for example, by combining the cleaving reagent with a suitable base, such as pyridine or the like, and continuing to agitate and stir for an additional period such as for an additional 5 minutes to 2 hours, preferably about 20 minutes to about 40 minutes. Adding the base and continued agitation causes the temperature of the vessel contents to increase. At the end of agitation, the vessel contents may be at a temperature in the range of from about 0° C. to about 15° C., preferably about 5° C. to about 10° C.

Factors such as swelling and shrinking the resin in order to improve aspects of the peptide recovery can optionally be incorporated into the overall synthesis process. These techniques are described, for example, in U.S. Pat. Pub. No. 2005/0164912 A1.

In some aspects, the cleaved peptide fragments can be prepared for solution phase coupling to other peptide fragments and/or amino acids. Peptide coupling reactions in the solution phase are reviewed in, for example, *New Trends in Peptide Coupling Reagents*; Albericio, Fernando; Chinchilla, Rafeal; Dodsworth, David J.; and Najera, Armen; Organic Preparations and Procedures International (2003), 33(3), 203-303.

Coupling of peptide intermediate fragments to other fragments or amino acid(s) in the solution phase can be carried out using in situ coupling reagents, for example benzotriazol-1-yl-oxy-tris-(dimethylamino)phosphoniumhexafluorophosphate (BOP), benzotriazol-1-yl-oxy-tripyrrolidinophosphonium hexafluorophosphate (PyBOP), o-(benzotriazol-1-yl)-N,N,N',N'-tetramethyluronium hexafluorophosphate (HBTU), o-(7-azabenzotriazol-1-yl)-1,1,3,3-tetramethyluronium hexafluoroborate (HATU), o-(7-azabenzotriazol-1-yl)-1,1,3,3-tetramethyluronium tetrafluorophosphate (TATU), o-(1H-6-chloro-benzotriazol-1-yl)-1,1,3,3-tetramethyluronium hexafluorophosphate (HCTU), o-(1H-6-chloro-benzotriazol-1-yl)-1,1,3,3-tetramethyluronium tetrafluoroborate (TCTU), o-(benzotriazol-1-yl)oxybios-(pyrrolidino)-uronium hexafluorophosphate (HAPyU), dicyclohexylcarbodiimide (DCC), diisopropylcarbodiimide, 3-(diethoxyphosphoryloxy)-1,2,3-benzotriazine-4(3H)-one (DEPBT), water-soluble carbodiimide (WSCDI), o-(cyano-ethoxycarbonyl-methyleneamino)-N,N,N',N''-tetramethyluronium tetrafluoroborate (TOTU) or o-(benzotriazol-1-yl)-N,N,N',N'-tetramethyluronium tetrafluoroborate (TBTU). Other coupling techniques use preformed active esters such as hydroxysuccinimide (HOSu) and p-nitrophenol (HONP) esters; preformed symmetrical anhydrides; non-symmetrical anhydrides such as N-carboxyanhydrides (NCAs); or acid halides such as acyl fluoride as well as acyl chloride.

A suitable coupling solvent can be used in the solution phase coupling reaction. It is understood that the coupling solvent(s) used can affect the degree of racemization of the peptide bond formed; the solubility of the peptide and/or peptide fragments; and the coupling reaction rate. In some embodiments, the coupling solvent includes one or more water-miscible reagents. Examples of water-miscible solvents include, for example, DMSO, pyridine, chloroform, dioxane, tetrahydrofuran, ethyl acetate, N-methylpyrrolidone, dimethylformamide, dioxane, or mixtures thereof.

In other embodiments, the coupling reaction may include one or more non water-miscible reagents. An exemplary non water-miscible solvent is methylene chloride. In these embodiments, the non water-miscible solvent is preferably compatible with the deprotection reaction; for example, if a non water-miscible solvent is used preferably it does not adversely affect the deprotection reaction.

After the peptide of SEQ ID No. 10 is formed, the product can be subject to deprotection, purification, lyophilization, further processing (e.g., reaction with another peptide to form a fusion protein); combinations of these, and/or the like, as desired.

For example, according to the invention, the side-chain protecting groups are typically retained on the peptide intermediate fragments throughout solid phase synthesis and also into and throughout the solution phase coupling reactions. Generally, after solution phase step is completed, one or more deprotection steps may be performed to remove one or more protecting groups from the peptide.

The removal of side chain protecting groups by global deprotection typically utilizes a deprotection solution that includes an acidolytic agent to cleave the side chain protecting groups. Commonly used acidolytic reagents for global deprotection include neat trifluoroacetic acid (TFA), HCl, Lewis acids such as $BF_3Et_2O$ or $Me_3SiBr$, liquid hydrofluoric acid (HF), hydrogen bromide (HBr), trifluoromethanesulfonic acid, and combinations thereof. The deprotection solution also includes one or more suitable cation scavengers, for example, dithiothreitol (DTT), anisole, p-cresol, ethanedithiol, or dimethyl sulfide. The deprotection solution can also include water. As used herein, amounts of reagents present in the deprotection composition are typically expressed in a ratio, wherein the amount of an individual component is expressed as a numerator in "parts", such as "parts weight" or "parts volume" and the denominator is the total parts in the composition. For example, a deprotection solution containing $TFA:H_2O:DTT$ in a ratio of 90:5:5 (weight/weight/weight) has TFA at 90/100 parts by weight, $H_2O$ at 5/100 parts by weight, and DTT at 5/100 parts by weight.

The precipitation is typically done using an ether, e.g., diethyl ether or MTBE (Methyl Tert Butyl Ether). After precipitation, the peptide is desirably isolated and dried before being combined with other ingredients, lyophilized, packaged, stored, further processed, and/or otherwise handled. This may be accomplished in any suitable fashion. According to one suitable approach, the peptide is collected via filtering, washed with ample MTBE washes to reduce final salt content to a suitable level, and then dried.

The present invention also provides useful techniques for purifying a wide range of peptides, including GLP-1 peptides and their counterparts.

A particularly preferred purification process involves at least two purification passes through chromatographic media, wherein at least a first pass occurs at a first pH and at least a second pass occurs at a second pH. More preferably, the first pass occurs at an acidic pH, while the second pass occurs at a basic pH. In preferred embodiments, at least one pass under acidic conditions occurs prior to a pass occurring under basic conditions. An illustrative mode of practicing this purification approach can be described in the illustrative context of purifying fully protected peptide 11. Initially, the peptide is globally de-protected. Both N-terminus and side chain protecting groups are cleaved. A first chromatographic pass is carried out in a water/ACN gradient, using enough TFA to provide a pH of about 1 to 5, preferably about 2. A second pass is then carried out in a water/ACN gradient using a little ammonia and/or ammonium acetate, or the like, to provide a pH of around 8 to 9, preferably 8.5 to 8.9.

The pH values, whether acid or base, promote uniformity in that a uniform ionic species is present in each instance. Thus, the acidic pH desirably is sufficiently low so that substantially all of the amino acid residues in the peptide material are protonated. The basic pH is desirably high enough so that substantially all of the amino acid residues in the peptide material are deprotonated. The acid and base chromatography can be carried out in any order. It is convenient to do the basic chromatography last when the peptide acetate is a desired product inasmuch as the acetate may be the product of chromatography.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), (3-(Diethoxyphosphoryloxy)-1,2,3-benzotriazin-4(3H)-one) (DEPBT), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), ethylene glycol dimethyl ether (DME), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), (benzotriazol-1-yloxy)tripyrrolidinophosphonium hexafluorophosphate (PyBOP), room temperature (rt or RT), tert-butyldimethylsilyl or t-$BuMe_2Si$ (TBDMS), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TSOH or pTsOH), 4-Me-$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

The principles of the present invention will now be further illustrated with respect to the following illustrative examples. In the following all percentages and ratios are by volume unless otherwise expressly stated.

EXAMPLES

Examples 1-18 pertain the coupling reaction scheme described in Scheme 1 and Fragments 1, 2, 3, and 3' as defined therein.

Example 1

Solid Phase Synthesis of Fragment 1 with Fmoc Protection at the N-Terminus, and Side Chain Protection on the His and Glu A. Preparation of Fmoc-Gly-Loaded 2CTC Resin
Initially, Fmoc-Gly-loaded 2CTC resin was prepared. Amounts of reagents used are listed in following table:

| Preparation of Fmoc-Gly-2-Chlorotrityl Resin | | | | | |
|---|---|---|---|---|---|
| Materials | MW | Eq | mmol | Grams [g] | mL |
| 2-Chlorotritylchloride resin | — | — | 52.24 | 35.06 | — |
| Fmoc-Gly-OH | 297.3 | 1.0 | 13.06 | 3.88 | — |
| Diisopropylethylamine (DIEA) | 129.25 | 2.35 | 30.72 | 3.97 | |
| Dimethyl formamide (DMF) | | | | | 1270 |
| Dichloromethane (DCM) | | | | | 1785 |
| 9:1 by volume Methanol:DIEA | | | | | 350 |
| Isopropanol (IPA) | | | | | 1050 |

2-CTC resin was charged to a 500 mL peptide reactor and swelled with 400 mL DCM for 30 min at 25° C. The bed was drained and a solution of Fmoc-Gly-OH and DIEA in 8 volume of DMF:DCM (87.5:12.5) was added. The mixture was stirred under nitrogen for 2 hours at a temperature of 25° C.

The bed was drained and washed once with 350 mL DMF and once with 175 mL DMF. Then, remaining active sites on the 2-CTC resin were end-capped with 350 mL of MeOH:DIEA (9:1) solution for 1 hour. The bed was drained, washed with 250 mL DMF two times, and then with 350 mL DCM four times. The resin was de-swelled by washing with 3×350 mL IPA. The resin was dried to a constant weight to give 38.20 g of loaded resin. Analysis showed a loading factor of 0.18 mmol/g.

B. Solid Phase Synthesis
Solid phase synthesis was carried out starting with 20.0 g of Fmoc-Gly-2-CTC resin loaded at 0.18 mmol/g as prepared in Part A of this Example 1. The resin was swelled in DCM (200 mL) for 30 min at 25° C. The DCM solvent was drained and the resin was washed three times with NMP (5 vol. each wash).

The resin was then treated twice with 20% by volume piperidine in NMP (5 vol. each treatment) to remove Fmoc protecting groups. After the second 20% piperidine/NMP treatment, the resin was washed five times with NMP (5 vol. each wash) to a negative chloranil test.

To prepare the coupling solution, the amino acid (2.85 equiv.) and 6-Chloro-1-Hydroxybenzotriazole (6-Cl-HOBT, 2.85 equiv.) were weighed, dissolved in 2.55× volume of NMP then combined with DIEA (3.25 equiv.) at 5° C. to 10° C. TBTU (2.85 equiv.) was dissolved in 1.3× volume of NMP at 5° C. to 10° C. The two solutions were then combined. The resultant solution was added to the reaction vessel. The flask was rinsed with 1.3× volume of DCM added into the reactor, which was then stirred for 2-3 hours at 25° C.-27° C. The sample was pulled for Kaiser Test to check the reaction for completion. If the coupling reaction was incomplete after 3 hours (positive Kaiser Test), the reaction vessel was drained and recoupling was performed with fresh solution of activated amino acid. After completion of the coupling reaction, the coupling solution was drained and the resin was washed with NMP 4 times (5 vol. each wash). Then removal of the Fmoc protecting group and coupling reaction cycle was repeated for the remaining amino acids in the fragment (i.e., in the order of Glu(OtBu)→Aib→His(trt)).

Due to difficulty of the coupling reaction between activated Fmoc-His(trt)-OH and H-Aib-Glu(OtBu)-Gly-2-CTC and the instability of the activated Fmoc-His(trt)-OH, the coupling reaction was forced to completion by draining the reaction solution after one hour and immediately performing the recoupling reaction with a second, fresh activated Fmoc-His(trt)-OH solution.

All reagents used in Part B of this example are listed in following table:

| Amino Acid | g | 6-Cl-HOBT (g) | DIEA (g) | NMP (mL) | TBTU (g) | NMP (mL) | DCM (mL) | Coupling time (min) |
|---|---|---|---|---|---|---|---|---|
| Glu(OtBu) | 4.34 | 1.76 | 1.55 | 51.0 | 3.28 | 26.0 | 26.0 | 150 |
| Aib | 3.36 | 1.76 | 1.51 | 51.0 | 3.29 | 26.0 | 26.0 | 155 |
| His(trt) | 6.32 | 1.78 | 1.56 | 51.0 | 3.29 | 26.0 | 26.0 | 60 |
| His(trt) recoupling | 6.32 | 1.79 | 1.56 | 51.0 | 3.29 | 26.0 | 26.0 | 92 |

The resin-bound peptide fragment was washed with NMP (5 vol.) 4 times, DCM (6 vol.) 5 times, IPA (5 vol.) 3 times. The de-swelled resin was then dried at 35° C. under vacuum to give 22.58 g resin and resin-bound peptide.

C. Cleavage of the Fmoc and Side-Chain Protected Fragment from the Resin

The built resin from Part B above was swelled in DCM (12.5 volumes relative to the weight of resin used; 12.5 ml DCM per g of resin or 12.5 liters per kg) for 30 min at 25° C. and then washed with DCM 2 times (6.25 vol. each wash) to remove any NMP residue. The resin was cooled with the last DCM wash to −5° C. The DCM was drained and a cold solution of 1% TFA/DCM (10 vol. at −5° to −10° C.) was added and stirred for 30 min at 0° C. Pyridine (1.3 equiv. of TFA) was added to the reactor to neutralize TFA. The cleavage solution was filtered off and collected in a flask. While the vessel warmed up to 25° C., the resin was washed with DCM 7 times (7.5 vol.). The washes were combined with the cleavage solution. The DCM cleavage solution was combined with water (7.5 vol.). The resultant mixture was distilled under reduced pressure to remove DCM (350 torr at 28° C.). The peptide fragment precipitated out from the water when DCM was removed. The fragment was washed with water and dried at 30°-35° C. under vacuum. A total of 4.73 g of Fmoc-(Aib8) GLP-1(7-10)-OH was obtained.

Example 2

A. Preparation of Fmoc-Gly-Loaded 2CTC Resin

Fmoc-Gly-loaded 2CTC resin was prepared. The amounts of reagents used are listed in following table:

| Preparation of Fmoc-Gly-2-Chlorotrityl Resin | | | | |
|---|---|---|---|---|
| Materials | MW | Eq | mmol | grams | mL |
| 2-Chlorotritylchloride resin | — | — | 59.66 | 40.04 | — |
| Fmoc-Gly-OH | 297.3 | 1.0 | 29.84 | 8.87 | — |
| Diisopropylethylamine (DIEA) | 129.25 | 1.67 | 49.90 | 6.45 | |
| Dimethyl formamide (DMF) | | | | | 1580 |
| Dichloromethane (DCM) | | | | | 1840 |
| 9:1 Methanol:DIEA | | | | | 390 |
| Isopropanol (IPA) | | | | | 1050 |

2-CTC resin was charged to a 500-mL peptide reactor and swelled with 400 mL DCM for 30 min. The resin was drained, and a solution Fmoc-Gly-OH and DIEA in 8 volume of DMF: DCM (87.5:12.5 by volume) was added. The mixture was stirred under nitrogen for 2 hours at a temperature of 25° C.

The resin bed was drained and washed once with 400 mL DMF and once with 200 mL DMF. Then, remaining active sites on the 2-CTC resin were end-capped with 390 mL of MeOH:DIEA (9:1 by volume) solution for 1 hour. The bed was drained again, washed two times with 350 mL DMF, and washed four times with 350 mL DCM. The resin was then de-swelled by washing with 3×350 mL IPA. The resin was dried at 35° C. under vacuum to a constant weight to give 48.51 g of loaded resin. Analysis showed a loading factor of 0.54 mmol/g.

B. Solid Phase Synthesis

Solid phase synthesis was carried out starting with 27.59 g of Fmoc-Gly-2-CTC resin loaded at 0.54 mmol/g. The resin was swelled in DCM (300 mL) for 30 min at 25° C. The DCM solvent was drained, and the resin was washed and three times with NMP (5 vol. each wash).

The resin was then treated twice with 20% by volume piperidine in NMP (5 vol. each treatment) to remove Fmoc protecting groups. After the second 20% piperidine/NMP treatment, the resin was washed six times with NMP (5 vol. each wash) to a negative chloranil test.

To prepare the coupling solution, the amino acid (1.7 equiv.) and 6-chloro-1-Hydroxybenzotriazole (6-Cl-HOBT, 1.7 equiv.) were weighed, dissolved in 4.6× volume of NMP, and then combined with DIEA (1.9 equiv.) at 10° C. to 5° C. TBTU (1.7 equiv.) was dissolved in 2.28× volume of NMP at 10° C. to 5° C. The two solutions were then combined. The resultant solution was added to the reaction vessel. The flask was rinsed with 2.28 volumes of DCM into the reactor, which was then stirred for 2-3 hours at 25° C. to 27° C. The sample was pulled for a Kaiser Test to check the reaction for completion. After completion of the coupling reaction, the coupling solution was drained, and the resin was washed with NMP 4 times (5 vol. each wash). Removal of the Fmoc group and coupling reaction cycle was repeated for the remaining amino acids in the fragment (i.e., in the order of Glu(OtBu)→Aib→His(trt)).

All reagents used in this example are listed in following table:

| Amino Acid | g | 6-Cl-HOBT (g) | DIEA (g) | NMP (mL) | TBTU (g) | NMP (mL) | DCM (mL) | Coupling time (min) |
|---|---|---|---|---|---|---|---|---|
| Glu(OtBu) | 10.79 | 4.24 | 2.67 | 127 | 8.13 | 63 | 63 | 156 |
| Aib | 8.26 | 4.32 | 3.73 | 125 | 8.14 | 65 | 65 | 180 |
| His(trt) | 15.68 | 4.31 | 3.69 | 125 | 8.12 | 65 | 65 | 180 |

C. Cleavage of the Fragment from the Resin

The built resin was washed with NMP (5 vol.) 6 times and then DCM (6 vol.) 8 times to remove NMP residue. The resin was cooled with the last DCM wash to −5° C. After draining DCM, a cold (−5° C. to −10° C.) solution of 1% TFA/DCM (10 vol.) was added, and the resultant pot mixture was stirred for 30 min at 0° C. Pyridine (1.3 equiv., of TFA) was charged to the reactor to neutralize the TFA. The cleavage solution was collected in the flask. While the vessel warmed up to 25° C., the resin was washed with DCM (7.5 vol.) 11 times and drained into the cleavage solution. The DCM solution was combined with water (10 vol.). The resultant mixture was distilled under reduced pressure to remove DCM (350 torr at 28° C.). The fragment precipitated out from water when DCM was removed. The fragment was washed with water and dried at 30° C.-35° C. under vacuum. A total of 11.12 g Fmoc-(Aib$^8$)GLP-1(7-10)-OH (78.8% yield) was obtained.

Example 3

A. Preparation of Fmoc-Gly-Loaded 2CTC Resin

Fmoc-Gly-loaded 2CTC resin was prepared. The amounts of reagents used are listed in following table:

Preparation of Fmoc-Gly-2-Chlorotrityl Resin

| Materials | MW | Equiv. | mmol | grams [g] | mL |
|---|---|---|---|---|---|
| 2-Chlorotritylchloride resin | — | — | 60.88 | 40.86 | — |
| Fmoc-Gly-OH | 297.3 | 1.0 | 42.58 | 12.66 | — |
| Diisopropylethylamine (DIEA) | 129.25 | 1.48 | 63.21 | 8.17 | |

Preparation of Fmoc-Gly-2-Chlorotrityl Resin

| Materials | MW | Equiv. | mmol | grams [g] | mL |
|---|---|---|---|---|---|
| Dimethyl formamide (DMF) | | | | | 1380 |
| Dichloromethane (DCM) | | | | | 1840 |
| 9:1 Methanol:DIEA | | | | | 390 |
| Isopropanol (IPA) | | | | | 1000 |

2-CTC resin was charged to a 500-mL peptide reactor and swelled with 400 mL DCM for 30 min. The bed was drained, and a solution Fmoc-Gly-OH and DIEA in 8 volume of DMF:DCM (87.5:12.5) was added. The mixture was stirred under nitrogen for 2 hours at a temperature of 25° C.

The bed was drained and washed once with 400 mL DMF. Then, any remaining active sites on the 2-CTC resin were end-capped with 390 mL of MeOH:DIEA (9:1) solution for 1 hour. The bed was drained, washed two times with 350 mL DMF, and then four times with 350 mL DCM. The resin was de-swelled by washing with 4×250 mL IPA. The resin was dried at 35° C. under vacuum to a constant weight to give 52.02 g of loaded resin. Analysis showed a loading factor of 0.72 mmol/g.

B. Solid Phase Synthesis

Solid phase synthesis was carried out starting with 24.43 g of Fmoc-Gly-2-CTC resin loaded at 0.72 mmol/g. The resin was swelled in DCM (250 mL) for 30 min at 25° C. The DCM solvent was drained and the resin was washed and three times with NMP (5 vol. each wash).

The resin was then treated twice with 20% piperidine in NMP (5 vol. each treatment) to remove Fmoc protecting groups. After the second 20% piperidine/NMP treatment, the resin was washed six times with NMP (5 vol. each wash) to a negative chloranil test.

To prepare the coupling solution, the amino acid and 6-Chloro-1-Hydroxybenzotriazole (6-Cl-HOBT) were weighed, dissolved in NMP and then combined with DIEA at 5° C. to 10° C. TBTU was dissolved in NMP at 5° C. to 10° C. The two solutions were then combined. The resultant solution was added to a reaction vessel. The flask was rinsed with DCM (see following table for amounts) into the reactor, which was stirred for 2-6 hours at 25° C. to 27° C. The sample was pulled for Kaiser Test to check the reaction for completion. If the coupling reaction was incomplete after 3 hours (positive Kaiser Test), the reaction vessel was drained and a recoupling was performed with a fresh solution of activated amino acid. After the coupling reaction was completed, the coupling solution was drained and the resin was washed with NMP 4 times (5 vol. each wash). Then, removal of the Fmoc group and the coupling reaction cycle was repeated for the remaining amino acids in the fragment (i.e., in the order of Glu(OtBu)→Aib→His(trt)).

All reagents used in this example are listed in following table:

| Amino Acid | g/Eq | 6-Cl-HOBT (g/Eq) | DIEA (g/Eq) | NMP (mL) | TBTU (g/Eq) | NMP (mL) | DCM (mL) | Coupling time (min) |
|---|---|---|---|---|---|---|---|---|
| Glu(OtBu) | 12.40/1.65 | 4.95/1.65 | 4.29/1.85 | 145 | 9.37/1.65 | 70 | 70 | 180 |
| Aib | 9.48/1.65 | 4.96/1.65 | 4.23/1.85 | 140 | 9.33/1.65 | 70 | 70 | 352 |
| Aib recoupling | 4.73/0.83 | 2.48/0.83 | 2.15/0.92 | 72 | 4.85/0.83 | 36 | 36 | 120 |
| His(trt) | 21.18/1.94 | 5.80/1.94 | 4.99/2.14 | 140 | 10.98/1.94 | 70 | 70 | 180 |
| His(trt) recoupling | 10.80/0.97 | 2.90/0.97 | 2.48/1.07 | 72 | 5.49/0.97 | 36 | 36 | 180 |

C. Cleavage of the Fragment Fmoc-Aa(7-10)-OH from the Resin

The built resin was washed with NMP (5 vol.) 6 times and DCM (6 vol.) 7 times to remove NMP. The resin was cooled with the last DCM wash to −5° C. The DCM was drained, and the resin bed was washed with a cold (−5° to −10° C.) solution of 1% TFA/DCM (11.26 vol.) for 5 min at 0° C. The cleavage solution was collected in the flask, to which had been added pyridine (1.3 equiv. of total TFA) for neutralizing TFA. Then, the second portion of cold 1% TFA/DCM (6.14 vol.) was added to the reactor and stirred for 2 min. The second cleavage solution was again drained into the collecting flask. While the vessel warmed up to 25° C., the resin was washed with DCM 9 times (8.2 vol.) and drained into the cleavage solution. The DCM solution was combined with water (8.2 vol.). The resultant mixture was distilled under reduced pressure to remove DCM (350 torr at 28° C.). The fragment precipitated out from water when DCM was removed. The fragment was washed with water and dried at 30° C.-35° C. under vacuum. A total of 14.02 g of Fmoc-(Aib$^8$)GLP-1(7-10)-OH (86.6% yield) according to SEQ ID NO. 7 was obtained. Analysis showed a purity of 94.3% AN.

Example 4

Fmoc-Thr(tBu)-Phe-Thr(tBu)-Ser(OtBu)-Asp(OtBu)-

Val-Ser(OtBu)-Ser(ψMe,Me)-Tyr(tBu)-Leu-

Glu(OtBu)-Gly-OH

Solid Phase Synthesis of GPA Fragment 2

Solid phase synthesis of Fmoc-AA(11-22)-OH was carried out starting with 20.0 g of H-Gly-2-CT resin loaded at 0.43 mmole/g. The resin was swelled in DCM (200 mL) for 30 min at 25° C. The DCM solvent was drained and the resin was washed three times with NMP (6 volumes for each wash). All scaling of volumes are relative to the initial resin weight (20.0 g) or to the number of moles of loaded amino acid on the resin (8.6 mmoles).

To prepare the coupling solution, the amino acid (1.7 equiv.) and 1-hydroxybenzotriazole hydrate (HOBT, 1.7 equiv.) were weighed, dissolved in 3.4 volumes of NMP then activated by combining with an HBTU (1.7 equiv.) solution in NMP (1.32 volumes) and then adding DIEA (3.5 equiv.) at 0° C.-5° C. The resulting solution was added to reaction vessel containing the resin, the activation flask was rinsed with 1.57 volumes of DCM into reactor, which was then stirred for 4 hours at 25° C.-27° C. After 4 hours stirring coupling reaction mixture, the coupling solution was drained and the resin was washed with NMP 4 times (6 vol. each wash). The resin was then treated twice with 20% piperidine in NMP (6 vol. each treatment) to remove Fmoc protecting groups. After the second 20% piperidine/NMP treatment, the resin was washed nine times with NMP (6 vol. each wash). The removal of the Fmoc protecting group and coupling reaction cycles were repeated for the remaining amino acids in the fragment (i.e., in the order of Glu(OtBu)→Leu→Tyr(tBu)→Ser(OtBu)-Ser(ψMe,Me)→Val→Asp(OtBu)→Ser(OtBu)→Thr(tBu)→Phe→Thr(tBu)).

All reagents used in this example are listed in following table:

| | Coupling Reaction of the GPA Fmoc-AA(11-22)-OH | | | | | | | |
|---|---|---|---|---|---|---|---|---|
| Amino Acid | g | HOBT H$_2$O (g) | DIEA (mL) | NMP (mL) | HBTU (g) | NMP (mL) | DCM (mL) | Coupling time (min) |
| Glu(OtBu) | 6.50 | 2.26 | 5.2 | 68.0 | 5.55 | 26.3 | 31.4 | 240 |
| Leu | 5.17 | 2.24 | 5.2 | 68.0 | 5.55 | 26.3 | 31.4 | 240 |
| Tyr(tBu) | 6.75 | 2.25 | 5.2 | 68.0 | 5.55 | 26.3 | 31.4 | 240 |
| Ser(OtBu)-Ser(ψMe,Me) | 7.47 | 2.28 | 5.2 | 68.0 | 5.55 | 26.3 | 31.4 | 240 |
| Val | 4.99 | 2.25 | 5.2 | 68.0 | 5.55 | 26.3 | 31.4 | 240 |
| Asp(OtBu) | 6.04 | 2.26 | 5.2 | 68.0 | 5.55 | 26.3 | 31.4 | 240 |
| Ser(OtBu) | 5.63 | 2.26 | 5.2 | 68.0 | 5.55 | 26.3 | 31.4 | 240 |
| Thr(tBu) | 5.83 | 2.28 | 5.2 | 68.0 | 5.55 | 26.3 | 31.4 | 240 |
| Phe | 5.67 | 2.26 | 5.2 | 68.0 | 5.55 | 26.3 | 31.4 | 240 |
| Thr(tBu) | 5.85 | 2.25 | 5.2 | 68.0 | 5.55 | 26.3 | 31.4 | 240 |

The built resin was washed with NMP (6 vol.) 4 times and DCM (6 vol.) 7 times.

Cleavage of the Fragment 2 (Fmoc-AA(11-22)-OH) from Built Resin:

The built resin from above was cooled with the last DCM wash to −5° C. The DCM was drained and the cold solution of 1% v/v TFA/DCM (10 vol. at −5° to −10° C.) was added and stirred at 0° C. Pyridine (1.38 equiv. relative to TFA) was added to the cleavage receiver to neutralize the TFA. After 30 min stirring, the cleavage solution was collected in the cleavage receiver. Then another cold solution of 1% TFA/DCM (5 vol. at −5° to −10° C.) was added and stirred for 30 min at 0° C. Pyridine (1.38 equiv. to TFA) was added to cleavage vessel to neutralize TFA. While vessel warming up to 25° C., the resin was washed with DCM 6 times (6 vol.) and drained into the cleavage solution receiver. The resulting DCM cleavage and wash solution was concentrated (7.5 vol) and then combined with water (5 vol.). The bottom DCM layer was further concentrated (1.5 vol) and fed into heptane (20 vol) to precipitate out the product. The resulting mixture was distilled under reduced pressure to remove the remaining DCM (350-100 torr at 25° C.). The fragment 2 precipitated out from the heptane when the DCM was removed. The fragment 2 was washed with heptane and dried at 30° C. to 35° C. under vacuum. A total of 14.35 g of GPA Fmoc-AA(11-22)-OH with a purity of 88.4% AN was obtained, yield of 85.5%.

Example 5

The above batch build was repeated. After cleavage of the Fragment 2 from the built resin, the DCM solution was concentrated to 7.5 vol and washed with water (3 times with 5 volumes each). The bottom DCM layer was concentrated again to 3.75 vol. This DCM solution was combined with water (20 vol) and the remaining DCM removed under vacuum at 25° C. The precipitating product was then filtered and dried under vacuum at 35° C. This gave 14.95 g Fragment 2, 89% yield with 93.1% AN purity.

Example 6

Solid Phase Synthesis of side chain protected Fmoc-(Aib$^{35}$) GLP-1 (23-35)-OH (Fragment 3)

A. Preparation of Fmoc-Aib-Loaded 2CTC Resin

Fmoc-Aib-loaded 2CTC resin was prepared. The amounts of reagents used are listed in following table:

| Preparation of Fmoc-Aib-2-Chlorotrityl Resin | | | | | |
|---|---|---|---|---|---|
| Materials | MW | Eq | mmol | grams [g] | mL |
| 2-Chlorotritylchloride resin | — | — | 59.66 | 40.04 | — |
| Fmoc-Aib-OH | 325.5 | 1.0 | 14.91 | 4.85 | — |
| Diisopropylethylamine (DIEA) | 129.25 | 2.39 | 35.20 | 4.61 | |
| Dimethyl formamide (DMF) | | | | | 1480 |
| Dichloromethane (DCM) | | | | | 1840 |
| 9:1 Methanol:DIEA | | | | | 450 |
| Isopropanol (IPA) | | | | | 1050 |

2-CTC resin was charged to a 500 mL peptide reactor and swelled with 400 mL DCM for 30 min. The bed was drained, and a solution of Fmoc-Aib-OH and DIEA in 8 volume of DMF:DCM (87.5:12.5) was added. The mixture was stirred under nitrogen for 2 hours at a temperature of 25° C.

The bed was drained and washed with DMF, 400 mL once and 200 mL a second time. Then, any remaining active sites on the 2-CTC resin were end-capped with 400 mL of MeOH:DIEA (9:1) solution for 1 hour. The bed was drained. The resin was washed once with 450 mL DMF/MeOH/DIEA (4:0.9:0.1), once with 200 mL DMF, and four times with 350 mL DCM. The resin was de-swelled by washing with 3×350 mL IPA. The resin was dried to a constant weight to give 45.15 g of loaded resin. Analysis showed a loading factor of 0.24 mmol/g.

B. Solid Phase Synthesis 10.01 g of Fmoc-Aib-2-CTC resin with loading factor at 0.24 mmol/g were charged to a reaction vessel and swelled in DCM (120 mL) for 30 min at 25° C. The DCM solvent was drained, and the resin was washed three times with NMP (6 vol. each wash).

The resin was then treated twice with 5% by volume piperidine in NMP (6 vol. each treatment) to remove Fmoc protecting groups. After the second 5% piperidine/NMP treatment, the resin was washed four times with NMP (6 vol. each wash).

To prepare the coupling solution, the amino acid (1.875 equiv.) and 1-hydroxybenzotriazole monohydate (HOBT hydrate, 2.07 equiv.) were dissolved in 3.5× volume of NMP at 5° C. to 10° C. and then combined with a 16.1 mL solution of HBTU (2.0 equiv.) in NMP (1.5× vol.). Then 2.2 mL DIEA (2.63 equiv.) was added to the activation vessel at 10° C. to 5° C. The resultant solution was transferred to a reaction vessel. The activation vessel was rinsed with 1.5× volume of DCM into the reactor, which was then stirred for 2 hours at 25° C. The reaction vessel was drained. The coupling reaction was repeated one more time with fresh solution of activated amino acid (1.875 eq) After the second coupling reaction was completed, the coupling solution was drained and the resin was washed with NMP 4 times (6 vol. each wash). Then, removal of the Fmoc group and coupling reaction cycle was repeated for the remaining amino acids in the fragment (i.e., in the order of Lys(Boc)→Val→Leu→Trp(Boc)→Ala→Ile→Phe→Glu(OtBu)→Lys(Boc)→Ala→Ala→Gln(trt)).

All reagents used in this example are listed in following table:

| Coupling Reaction of Fmoc-AA(23-35)-OH | | | | | | | |
|---|---|---|---|---|---|---|---|
| Amino Acid | g | HOBT hydrate (g) | NMP (mL) | HBTU (g) | NMP (mL) | DCM (mL0 | DIEA (mL) | Coupling time (min) |
| Lys(Boc) | 2.12 | 0.76 | 30.0 | 1.83 | 15.0 | 15.0 | 1.1 | 120 |
| Lys(Boc) recoupling | 2.12 | 0.76 | 30.0 | 1.83 | 15.0 | 15.0 | 1.1 | 120 |
| Val | 1.53 | 0.76 | 30.0 | 1.83 | 15.0 | 15.0 | 1.1 | 120 |
| Val recoupling | 1.53 | 0.76 | 30.0 | 1.83 | 15.0 | 15.0 | 1.1 | 120 |
| Leu | 1.58 | 0.76 | 30.0 | 1.83 | 15.0 | 15.0 | 1.1 | 120 |
| Leu recoupling | 1.58 | 0.76 | 30.0 | 1.83 | 15.0 | 15.0 | 1.1 | 120 |
| Trp(Boc) | 2.37 | 0.76 | 30.0 | 1.83 | 15.0 | 15.0 | 1.1 | 120 |
| Trp(Boc) recoupling | 2.36 | 0.76 | 30.0 | 1.83 | 15.0 | 15.0 | 1.1 | 120 |
| Ala | 1.42 | 0.76 | 30.0 | 1.83 | 15.0 | 15.0 | 1.1 | 120 |
| Ala recoupling | 1.42 | 0.76 | 30.0 | 1.83 | 15.0 | 15.0 | 1.1 | 120 |
| Ile | 1.59 | 0.76 | 30.0 | 1.83 | 15.0 | 15.0 | 1.1 | 120 |
| Ile recoupling | 1.59 | 0.76 | 30.0 | 1.83 | 15.0 | 15.0 | 1.1 | 120 |
| Phe | 1.74 | 0.76 | 30.0 | 1.83 | 15.0 | 15.0 | 1.1 | 120 |

-continued

Coupling Reaction of Fmoc-AA(23-35)-OH

| Amino Acid | g | HOBT hydrate (g) | NMP (mL) | HBTU (g) | NMP (mL) | DCM (mL0 | DIEA (mL) | Coupling time (min) |
|---|---|---|---|---|---|---|---|---|
| Phe | 1.74 | 0.76 | 30.0 | 1.83 | 15.0 | 15.0 | 1.1 | 120 |
| recoupling | | | | | | | | |
| Glu(OtBu) | 1.93 | 0.76 | 30.0 | 1.83 | 15.0 | 15.0 | 1.1 | 120 |
| Glu(OtBu) | 1.92 | 0.76 | 30.0 | 1.83 | 15.0 | 15.0 | 1.1 | 120 |
| recoupling | | | | | | | | |
| Lys(Boc) | 2.12 | 0.76 | 30.0 | 1.83 | 15.0 | 15.0 | 1.1 | 120 |
| Lys(Boc) | 2.11 | 0.76 | 30.0 | 1.83 | 15.0 | 15.0 | 1.1 | 120 |
| recoupling | | | | | | | | |
| Ala | 1.41 | 0.76 | 30.0 | 1.83 | 15.0 | 15.0 | 1.1 | 120 |
| Ala | 1.40 | 0.76 | 30.0 | 1.83 | 15.0 | 15.0 | 1.1 | 120 |
| recoupling | | | | | | | | |
| Ala | 1.41 | 0.76 | 30.0 | 1.83 | 15.0 | 15.0 | 1.1 | 120 |
| Ala | 1.40 | 0.76 | 30.0 | 1.83 | 15.0 | 15.0 | 1.1 | 120 |
| recoupling | | | | | | | | |
| Gln(trt) | 2.77 | 0.76 | 30.0 | 1.83 | 15.0 | 15.0 | 1.1 | 120 |
| Gln(trt) | 2.76 | 0.76 | 30.0 | 1.83 | 15.0 | 15.0 | 1.1 | 120 |
| recoupling | | | | | | | | |

The built resin was isolated by washing with 4 times with NMP (6 vol.), 4 times with DCM (6 vol.), and 3 times with Isopropanol (IPA, 6 vol.). The built resin was dried at 35° C. under vacuum. 14.3 g built resin were obtained.

C. Cleavage of the Intermediate Fragment from Built Resin 6.6 g of built resin from above were swelled in 10× volume DCM for 30 min, and cooled to −10° C. The DCM was drained and a cold solution of 1% TFA/DCM (12 vol. at −5° C. to −10° C.) was added and stirred for 30 min at 0° C. The cleavage solution was collected in a flask containing pyridine (2-3 equiv. of TFA). While warming up to 25° C., the resin was stirred with 1% TFA/DCM (10× vol.) for 5 min and pyridine (2-3 equiv.) was added. After another 5 minutes, the solution was collected. The resin was washed with DCM 4 times (10 vol.). All DCM washes were combined with water (water/DCM=1/4). The resultant mixture was distilled under reduced pressure to remove DCM (350 torr at 28° C.). The fragment precipitated out from water when DCM was removed. The fragment was washed with water and dried at 30° C.-35° C. under vacuum. The cleavage procedure was repeated one more time. A total of 2.36 g of Fmoc-(Aib$^{35}$) GLP-1 (23-35)-OH was obtained (a 92% yield).

Example 7

A. Preparation of Fmoc-Aib-Loaded 2CTC Resin

Fmoc-Aib-loaded 2CTC resin was prepared. The amounts of reagents used in this example are listed in following table:

Preparation of Fmoc-Aib-2-Chlorotrityl Resin

| Materials | MW | Eq | mmol | grams (g) | mL |
|---|---|---|---|---|---|
| 2-Chlorotritylchloride resin | — | — | 59.67 | 40.05 | — |
| Fmoc-Aib-OH | 325.5 | 1.0 | 14.92 | 4.85 | — |
| Diisopropylethylamine (DIEA) | 129.25 | 2.35 | 35.20 | 4.55 | |
| Dimethyl formamide (DMF) | | | | | 1280 |
| Dichloromethane (DCM) | | | | | 1840 |
| 9:1 Methanol:DIEA | | | | | 400 |
| Isopropanol (IPA) | | | | | 1050 |

2-CTC resin was charged to a 500 mL peptide reactor and swelled with 400 mL DCM for 30 min. The bed was drained, and a solution Fmoc-Aib-OH and DIEA in 8 volume of DMF:DCM (87.5:12.5) was added. The mixture was stirred under nitrogen for 2 hours. at a temperature of 25° C.

The bed was drained and washed with 400 mL DMF. Then, any remaining active sites on the 2-CTC resin were end-capped with 400 mL of MeOH:DIEA (9:1) solution for 1 hour. The bed was drained, washed one time with 400 mL DMF, one time with 200 mL DMF, and four times with 350 mL DCM. The resin was de-swelled by washing with 3×350 mL IPA. The resin was dried to a constant weight to give 45.32 g of loaded resin. Analysis showed a loading factor of 0.30 mmol/g.

B. Solid Phase Synthesis

Solid phase synthesis was carried out starting with 15.0 g of Fmoc-Aib-2-CTC resin loaded at 0.30 mmole/g. The resin was swelled in DCM (150 mL) for 30 min at 25° C. The DCM solvent was drained and the resin was washed two times with DCM (6 vol. each wash), and three times with NMP (6 vol. each wash).

The resin was then treated twice with 20% piperidine in NMP (6 vol. each treatment) to remove Fmoc protecting groups. After the second 20% piperidine/NMP treatment, the resin was washed six times with NMP (6 vol. each wash) to a negative chloranil test.

To prepare the coupling solution, the amino acid (1.7 equiv.) and 6-Chloro-1-Hydroxybenzotriazole (6-Cl-HOBT, 1.7 equiv.) were weighed, dissolved in 2.6× volume of NMP at 10° C.-5° C., and then combined with DIEA (1.9 to 3.0 equiv.). TBTU or HBTU (1.7 equiv.) was dissolved in 1.33× volume of NMP at 10° C.-5° C. The two solutions were then combined. The resultant solution was added to a reaction vessel. The mixing flask was rinsed with 1.33× volume of DCM into the reactor, which was then stirred with resin for 2-3 hours at 25°-27° C. The sample was pulled for Kaiser Test to check the reaction completion. If the coupling reaction incomplete after 3 hours (positive Kaiser Test), the reaction vessel was drained, and recoupling was performed with fresh solution of activated amino acid. After the coupling reaction was completed, the coupling solution was drained and the resin was washed with NMP 4 times (6 vol. each wash). Then, the removal of the Fmoc group and coupling reaction cycle was repeated for the remaining amino acids in the fragment (i.e., in the order of Lys(Boc)→Val→Leu→Trp(Boc)→Ala→Ile→Phe→Glu(OtBu)→Lys(Boc)→Ala→Ala→Gln(trt)).

Due to a possible buttressing effect between 2-methylalanine (Aib) and 2-CTC resin, there is considerable difficulty to force the first two amino acid coupling reactions (Lys(Boc)-34 and Val-33) to completion. Therefore, both coupling reactions for (Lys(Boc)-34, Val-33) were performed three times (i.e., coupling was followed by two recouplings). Also, acetic anhydride was used to end-cap the unreacted resin-bound material after coupling reactions of Lys(Boc)-34 and Val-33. This has improved the efficiency of the subsequent purification by moving the impurities far from the desirable product during chromatographic purification.

All reagents used in this example are listed in following table:

| | | Coupling Reaction of the Fmoc-AA(23-35)-OH | | | | | | | |
|---|---|---|---|---|---|---|---|---|---|
| Amino Acid | g/ Eq | 6-Cl- HOBT (g/Eq) | DIEA (g/Eq) | NMP (mL) | TBTU (g/Eq) | HBTU (g/Eq) | NMP (mL) | DCM (mL) | Coupling time (min) |
| $1^{st}$ Lys(Boc) | 3.61/1.7 | 1.33/1.7 | 1.15/1.9 | 39.0 | 2.50/1.7 | — | 20.0 | 20.0 | 175 |
| $2^{nd}$ Lys(Boc) | 3.61/1.7 | 1.33/1.7 | 1.16/1.9 | 39.0 | 2.48/1.7 | — | 20.0 | 20.0 | 180 |
| $3^{rd}$ Lys(Boc) | 3.61/1.7 | 1.33/1.7 | 1.13/1.9 | 39.0 | 2.47/1.7 | — | 20.0 | 20.0 | 180 |
| Acetic Anhydride | 2.33/5.0 | — | 3.22/5.5 | 60.0 | — | — | 30.0 | — | 120 |
| $1^{st}$ Val | 2.62/1.7 | 1.33/1.7 | 1.13/1.9 | 39.0 | 2.51/1.7 | — | 20.0 | 20.0 | 170 |
| $2^{nd}$ Val | 2.62/1.7 | 1.33/1.7 | 1.17/1.9 | 39.0 | 2.49/1.7 | — | 20.0 | 20.0 | 180 |
| $3^{rd}$ Val | 2.63/1.7 | 1.32/1.7 | 3.67/1.9 | 39.0 | 2.50/1.7 | — | 20.0 | 20.0 | 141 |
| Acetic Anhydride | 4.69/10.0 | — | 7.13/12.0 | 60.0 | — | — | 30.0 | — | 153 |
| Leu | 2.73/1.7 | 1.35/1.7 | 1.12/1.9 | 39.0 | 2.50/1.7 | — | 20.0 | 20.0 | 180 |
| Trp(Boc) | 4.03/1.7 | 1.33/1.7 | 1.78/3.0 | 39.0 | 2.50/1.7 | — | 20.0 | 20.0 | 180 |
| Ala | 2.41/1.7 | 1.31/1.7 | 1.78/3.0 | 39.0 | — | 2.93/1.7 | 20.0 | 20.0 | 180 |
| Ile | 2.72/1.7 | 1.31/1.7 | 1.78/3.0 | 39.0 | — | 2.93/1.7 | 20.0 | 20.0 | 180 |
| Phe | 3.00/1.7 | 1.31/1.7 | 1.78/3.0 | 39.0 | — | 2.93/1.7 | 20.0 | 20.0 | 180 |
| Glu(OtBu) | 3.28/1.7 | 1.31/1.7 | 1.78/3.0 | 39.0 | — | 2.93/1.7 | 20.0 | 20.0 | 180 |
| Lys(Boc) | 3.61/1.7 | 1.31/1.7 | 1.78/3.0 | 39.0 | — | 2.93/1.7 | 20.0 | 20.0 | 180 |
| Ala | 2.40/1.7 | 1.31/1.7 | 1.78/3.0 | 39.0 | — | 2.93/1.7 | 20.0 | 20.0 | 180 |
| Ala | 2.41/1.7 | 1.31/1.7 | 1.78/3.0 | 39.0 | — | 2.93/1.7 | 20.0 | 20.0 | 180 |
| Gln(trt) | 4.72/1.7 | 1.31/1.7 | 1.78/3.0 | 39.0 | — | 2.93/1.7 | 20.0 | 20.0 | 180 |
| Gln(trt) | 4.72/1.7 | 1.31/1.7 | 1.78/3.0 | 39.0 | — | 2.93/1.7 | 20.0 | 20.0 | 180 |

C. Cleavage of the Fragment from the Built Resin

The built resin from above was washed with DCM 7 times (6 vol. each wash) to remove NMP residue, and the resin was cooled with the last DCM wash to −5° C.

The DCM was drained, and a cold solution of 1% TFA/DCM (12 vol. at −5° to −10° C.) was added and stirred for 30 min at 0° C. The cleavage solution was collected in a flask containing pyridine (1.3 equiv. of TFA). While the vessel warmed up to 25° C., the resin was washed with DCM 9 times (10 vol.) and drained into the cleavage solution. The DCM solution was combined with water (6 vol.). The resultant mixture was distilled under reduced pressure to remove DCM (350 torr at 28° C.). The fragment precipitated out from water when DCM was removed. The fragment was washed with and dried at 30°-35° C. under vacuum. For this example the cleavage procedure was repeated one more time. A total of 6.78 g of Fmoc-(Aib$^{35}$) GLP-1 (23-35)-OH was obtained (a 68.1% yield) with a purity of 87.3% AN.

Example 8

A. Preparation of Fmoc-Aib-Loaded 2CTC Resin

Fmoc-Aib-loaded 2CTC resin was prepared. The amounts of reagents used in this example are listed in following table:

| Preparation of Fmoc-Aib-2-Chlorotrityl Resin | | | | | |
|---|---|---|---|---|---|
| Materials | MW | Eq | mmol | Grams (g) | mL |
| 2-Chlorotritylchloride resin | — | — | 59.85 | 40.44 | — |
| Fmoc-Aib-OH | 325.5 | 1.0 | 20.95 | 6.82 | — |
| Diisopropylethylamine (DIEA) | 129.25 | 0.95 | 19.88 | 2.57 | |

-continued

| Preparation of Fmoc-Aib-2-Chlorotrityl Resin | | | | | |
|---|---|---|---|---|---|
| Materials | MW | Eq | mmol | Grams (g) | mL |
| Dimethyl formamide (DMF) | | | | | 1280 |
| Dichloromethane (DCM) | | | | | 1840 |
| 9:1 Methanol:DIEA | | | | | 400 |
| Isopropanol (IPA) | | | | | 1050 |

2-CTC resin was charged to a 500 mL peptide reactor and swelled with 400 DCM for 30 min. The bed was drained, and a solution of Fmoc-Aib-OH and DIEA in 8 volume of DMF:DCM (87.5:12.5) was added. The mixture was stirred under nitrogen for 2 hours at a temperature of 25° C.

The bed was drained and washed with 400 mL DMF. Then, any remaining active sites on the 2-CTC resin were end-capped with 400 mL of MeOH:DIEA (9:1) solution for 1 hour. The bed was drained, washed one time with 400 mL DMF, washed one time with 200 mL DMF, and washed four times with 350 mL DCM. The resin was de-swelled by washing with 3×350 mL IPA. The resin was dried to a constant weight to give 47.56 g of loaded resin. Analysis showed a loading factor of 0.37 mmol/g.

B. Solid Phase Synthesis

Solid phase synthesis was carried out starting with 25.0 g of Fmoc-Aib-2-CTC resin loaded at 0.37 mmol/g. The resin was swelled in DCM (250 mL) for 30 min at 25° C. The DCM solvent was drained, and the resin was washed two times with DCM (6 vol. each wash), and three times with NMP (6 vol. each wash).

The resin was then treated twice with 20% by volume piperidine in NMP (6 vol. each treatment) to remove Fmoc protecting groups. After the second 20% piperidine/NMP treatment, the resin was washed six times with NMP (6 vol. each wash) to a negative chloranil test.

To prepare the coupling solution, the amino acid and 6-chloro-1-hydroxybenzotriazole (6-Cl-HOBT) were weighed, dissolved in 3.2× volume of NMP (or DMF for Lys-34, Val-33, and Gln-23) then combined with DIEA at 10° C.-5° C. TBTU was dissolved in 1.6× volume of NMP (or DMF for Lys-34, Val-33, and Gln-23) at 10°-5° C. The two solutions were then combined. The resultant solution was added to reaction vessel, and the flask was rinsed with 1.6× volume of DCM into the reactor, which was stirred with resin for 2-3 hours at 25° C.-27° C. The sample was pulled for Kaiser Test to check the reaction completion. If the coupling reaction was incomplete after 3 hours (positive Kaiser Test), the reaction vessel was drained and recoupling was performed with fresh solution of activated amino acid. After the coupling reaction was completed, the coupling solution was drained, and the resin was washed with NMP 4 times (6 vol. each wash). Then, the deprotecting of the Fmoc group and coupling reaction cycle was repeated for remaining amino acid in the fragment (i.e., in the order of Lys(Boc)→Val→Leu→Trp(Boc)→Ala→Ile→Phe→Glu (OtBu)→Lys(Boc)→Ala→Ala→Gln(trt)).

Due to a possible buttressing effect between 2-methylalanine (Aib) and 2-CTC resin, there is considerable difficulty to force the first two amino acid coupling reactions (Lys(Boc)-34 and Val-33) to completion. The coupling conditions for Lys(Boc)-34, Val-33, and Gln(trt)-23 were modified by increasing the usages of both amino acid and 6-Cl-HOBT from 1.7 Eq to 2.5 Eq and DIEA from 1.9 Eq to 3.0 Eq. The solvent for coupling reaction was also changed from NMP to DMF in order to force the coupling reaction to completion. Also, in this example, acetic anhydride was used to end-cap the unreacted resin-bound material after coupling reactions of Lys(Boc)-34 and Val-33. This has improved the efficiency of the subsequent purification by moving the impurities far from the desirable product during chromatographic purification.

All reagents used in this example are listed in following table:

| Material | wt (g)/ Eq | 6-Cl-HOBT (g/Eq) | DIEA (g/Eq) | DMF (mL) | NMP (mL) | TBTU (g/Eq) | DMF (mL) | NMP (mL) | DCM (mL) | Coupling time (min) |
|---|---|---|---|---|---|---|---|---|---|---|
| Lys(Boc) | 10.84/2.5 | 3.93/2.5 | 3.63/3.0 | 80.0 | — | 7.44/2.5 | 40.0 | — | 40.0 | 170 |
| Acetic Anhydride | 4.72/5.0 | — | 6.61/5.5 | — | 100.0 | — | — | 50.0 | — | 120 |
| Val | 7.85/2.5 | 3.92/2.5 | 3.67/3.0 | 80.0 | — | 7.44/2.5 | 40.0 | — | 40.0 | 177 |
| Acetic Anhydride | 9.48/10.0 | — | 14.46/12.0 | — | 100.0 | — | — | 50.0 | — | 120 |
| Leu | 5.56/1.7 | 2.68/1.7 | 2.33/1.9 | — | 78.6 | 5.05/1.7 | — | 39.3 | 39.3 | 184 |
| Trp(Boc) | 8.30/1.7 | 2.70/1.7 | 2.28/1.9 | — | 78.6 | 5.05/1.7 | — | 39.3 | 39.3 | 180 |
| Ala | 4.92/1.7 | 2.68/1.7 | 2.30/1.9 | — | 78.6 | 5.05/1.7 | — | 39.3 | 39.3 | 177 |
| Ile | 5.56/1.7 | 2.70/1.7 | 2.26/1.9 | — | 78.6 | 5.06/1.7 | — | 39.3 | 39.3 | 168 |
| Phe | 6.10/1.7 | 2.70/1.7 | 2.31/1.9 | — | 78.6 | 5.06/1.7 | — | 39.3 | 39.3 | 168 |
| Glu(OtBu) | 6.72/1.7 | 2.67/1.7 | 2.29/1.9 | — | 78.6 | 5.05/1.7 | — | 39.3 | 39.3 | 168 |
| Lys(Boc) | 7.39/1.7 | 2.70/1.7 | 2.29/1.9 | — | 78.6 | 5.05/1.7 | — | 39.3 | 39.3 | 165 |
| Ala | 4.91/1.7 | 2.70/1.7 | 2.41/1.9 | — | 78.6 | 5.05/1.7 | — | 39.3 | 39.3 | 180 |
| Ala | 4.92/1.7 | 2.68/1.7 | 2.32/1.9 | — | 78.6 | 5.03/1.7 | — | 39.3 | 39.3 | 171 |
| Gln(trt) | 14.13/2.5 | 3.94/2.5 | 3.71/3.0 | 80.0 | — | 7.42/2.5 | 40.0 | — | 40.0 | 185 |

Coupling Reaction of the Fmoc-AA(23-35)-OH

C. Cleavage of the Fragment from Built Resin

The built resin from above was washed with DCM 6 times (6 vol. each wash) to remove NMP, and the resin was cooled with the last DCM wash to −5° C. The DCM was drained, and a cold solution of 1% TFA/DCM (10 vol. at −5° to −10° C.) was added and stirred for 30 min at 0° C. The cleavage solution was collected in a flask containing pyridine (1.3 equiv. of TFA). While the vessel warmed up to 25° C., the resin was washed with DCM 7 times (6 vol.) and drained into the cleavage solution. The DCM solution was combined with water (10 vol.). The resultant mixture was distilled under reduced pressure to remove DCM (350 torr at 28° C.). The fragment precipitated out from water when DCM was removed. The fragment was washed with and dried at 30° C.-35° C. under vacuum. For this example, the cleavage procedure was repeated one more time to achieve complete cleavage. A total of 12.36 g of Fmoc-(Aib$^{35}$) GLP-1 (23-35)-OH was obtained (a 59.35% yield) with a purity of 84.3% AN.

First GPA Solution Phase Synthesis of GPA Fragment 2+3', Fmoc-AA(11-36)-NH$_2$

Fmoc-Thr(tBu)-Phe-Thr(tBu)-Ser(OtBu)-Asp(OtBu)-

Val-Ser(OtBu)-Ser(ψMe,Me)-Tyr(tBu)-Leu-

Glu(OtBu)-Gly-Gln(trt)-Ala-Ala-Lys(Boc)-Glu(OtBu)-

Phe-Ile-Ala-Trp(Boc)-Leu-Val-Lys(Boc)-Aib-Arg-NH$_2$

Example 9

Solution Phase Synthesis of GPA Fragment 3'

The GPA Fragment 3, Fmoc-AA(23-35)-OH, (10.0 g, 1.0 equiv.) (Lot# B0705P001) and L-Argininamide Dihydrochloride (2.14 g, 2.0 equiv.) were mixed with DMSO (42 mL) and stirred at 23° C.-25° C. for 30 min. To this solution 1-hydroxybenzotriazole hydrate (HOBT, 2.0 equiv.) and HBTU (2.0 equiv.) in DMSO (42 mL) and DIEA (5.0 equiv.) were charged. The reaction was agitated at 25° C. and monitored by HPLC. After 22 hours, the reaction was complete. Then piperidine (5.0 equiv.) was added to the reaction solution. The removal of Fmoc protection group was done after 95 min at 25° C. A solution of MTBE (60 mL) and heptane (60 mL) was added to extract the reaction solution to remove excess piperidine. Then this two phase mixture was added to water (240 mL) to precipitate the product at 20° C.-22° C. After settling, the top MTBE/heptane layer was separated and bottom aqueous DMSO layer with the product was filtered and washed with additional MTBE/heptane. After vacuum drying at 35° C. the filter cake gave 11.1 g GPA Fragment 3'. HPLC analysis showed 72.9% AN Fragment 3' and 17% dibenzofulvene (DBF).

Example 10

Solution Phase Synthesis of GPA Fragment 2+3'

The GPA Fragment 3' (5.0 g) and Fragment 2 (4.35 g) were dissolved in DMF (30 mL). To this solution, a solution of HOBT hydrate (1.55 equiv.) and HBTU (1.56 equiv.) in DMF (20 mL) and DIEA (2.55 equiv.) were charged along with a DMF rinse (10 mL). The reaction was stirred at 25° C. and monitored by HPLC. After 145 min, additional Fragment 3' (0.5 g), HBTU (0.5 equiv.), and DIEA (1.3 equiv.) were added along with a DMF rinse (5 mL). The reaction was complete after overnight agitation. Piperidine (1.4 g) was charged to the reaction mixture. The Fmoc removal was done after 3 hours. The reaction mixture was quenched with water (140 mL) at 18°-26° C. The mixture was heated up to 40° C. then cooled to 20° C. The white solid formed was filtered and washed with water (twice, 100 mL each). The filter cake was air dried and then stirred with MTBE/heptane (1:1, 100 mL) at 40° C. for 15 min. After cooling to 25° C., the product was filtered, washed with MTBE/heptane (1:1, 4×50 mL), and vacuum dried at 35° C.-40° C. A total of 8.64 g, 97.7% yield, was obtained with a purity of 67.3% AN.

Solution Phase Synthesis of GPA Fragment 1+2+3' and Global De-Protection

Example 11

The Fragment 1 (0.93 g) was dissolved in DCM (20 mL). To this solution, Fragment 2+3' (4.02 g) was added along with a DCM (20 mL) rinse. HOBt hydrate (0.23 g, 1.5 equiv.) and HBTU (0.57 g, 1.5 equiv.) were charged with DCM (5 mL). Then, DIEA (0.95 mL, 2.0 equiv.) was charged to the agitated reaction mixture, which was a suspension. The reaction was agitated at 25° C. and monitored by HPLC. After 16 hours a reaction completion check indicated an excess of Fragment 2+3'. Additional Fragment 1 (0.081 g) and HBTU (0.068 g) were added using a DCM (5 mL) rinse. The reaction was stirred for an additional 68 hours. After the coupling reaction was complete, piperidine (0.6 mL) was charged to the reaction mixture. After stirring for 18 hours, the Fmoc removal was complete. The DCM then was stripped off the reaction mixture, under vacuum, until the residual volume was ~15 mL. The concentrated mixture was charged to a solution containing TFA (40 mL), DTT (2.1 g) and water (2.1 mL) at 15° C., followed by DCM rinses (2×5 mL). The reaction mixture was cooled to <5° C. after 6 hours agitation. Cold MTBE (160 mL, cooled in dry ice) was charged to the cleavage solution over 7 min. The quenched reaction mixture was allowed to warm up to 15° C. The resulting solid product was filtered, washed with MTBE (3×30 mL), and air dried overnight at ambient temperature. A 3.82 g of GPA crude (28.73% wt/wt) was obtained with a purity of 59.7% AN, 113% yield.

Synthesis of an Alternate Fragment 1

Example 12

Fragment 1 (Trt-His(Trt)-Aib-Glu(OtBu)-Gly-OH)

Starting with 7.0 g preloaded Fmoc-Gly-O-2-CT resin (loading 0.43 mmol/g), standard Fmoc chemistry was applied. The resin was first swelled in a 10 volumes (relative to the resin weight) of DCM for 30 min. Then DCM was drained and the resin was washed with 10 volumes of NMP for 4 times (5 min each).

Fmoc removal was accomplished by two treatments (10 and 20 minutes) of 10 volumes of a solution of 20% Piperidine in NMP(v/v). The Piperidine/NMP solution was drained after each treatment. The resin was then washed by NMP 6 times (10 volumes, 5 min/each). To prepare the coupling solution, the amino acid and HOBt, were weighed (2 equiv), dissolved in 25 mL of NMP containing HBTU (2 equiv), followed by an NMP/DCM (10 mL/15 mL) rinse. The resulting solution combined with DIEA (2 equiv) in NMP (5 mL) and was added to the reaction vessel containing the resin and mixed with the resin for 3 hours. After the coupling reaction was complete, the coupling solution was drained and the resin was washed with NMP 4 times (10× volume, 5 min/each).

The built peptide-resin was washed with DCM (4×70 mL, 5 min/each), and cooled to −5° C. The DCM was drained and the solution of 1% TFA/DCM (70 mL, cooled in dry ice) was added and stirred for 15 min. The cleavage solution was collected in a flask containing pyridine (2 mL). While the warming up to 20° C., the resin was washed with dry ice cooled 1% TFA/DCM (70 mL) over 20 min, and pyridine (4 mL) was added. After another 10 min of agitation, the solution was collected. The resin was then washed with DCM 4×70 mL, 5 min/each). The combined mixture of all the washes and the cleavage solutions was distilled at reduced pressure until to a volume of 100 mL was reached. The resultant solution was mixed with water (100 mL) and again distilled at reduced pressure. The peptide fragment crashed out from the water when the DCM was removed, and was filtered off. The solid peptide fragment was washed with water (3×50 mL) and air dried overnight at ambient temperature. The product (Alternate Fragment 1) weight was 0.58 g, 20% yield.

GPA Solid Phase Synthesis of GPA, all Couplings on Resin

Fmoc-His(trt)-Aib-Glu(OtBu)-Gly-Thr(tBu)-Phe-

Thr(tBU)-Ser(OtBU)-Asp(OtBu)-Val-Ser(OtBu)-

Ser(ψMe,Me)-Tyr(tBu)-Leu-Glu(OtBu)-Gly-Gln(trt)-

Ala-Ala-Lys(Boc)-Glu(OtBu)-Phe-Ile-Ala-Trp(Boc)-

Leu-Val-Lys(Boc)-Aib-OH

Solid Phase Synthesis of GPA Fragment 3 on 2CT Resin

```
Fmoc-Gln(trt)-Ala-Ala-Lys(Boc)-Glu(OtBu)-Phe-Ile-
Ala-Trp(Boc)-Leu-Val-Lys(Boc)-Aib-2-CT
```

Example 13

Solid phase synthesis of Fmoc-AA(23-35)-OH was carried out starting with 15.0 g of H-Aib-2-CT resin loaded at 0.46 mmole/g. The resin was swelled in DCM (120 mL) for 30 min at 25° C. The DCM solvent was drained and the resin was washed three times with NMP (6 vol. each wash).

To prepare the coupling solution, the amino acid and 1-hydroxybenzotriazole hydrate (HOBT) were weighed, dissolved in NMP (4 vol for Lys-34, Val-33, Lys-26, Ala-25, Ala-24, and Gln-23; 4.2 vol for Leu-32 to Glu-27) then combined with an HBTU solution in NMP (178.4 g/L) and DIEA at −5° C. to 0° C. The resulting solution was added to resin containing reaction vessel, the flask rinse with 2.0 volumes of DCM was added to the reactor, which was stirred with resin at 25° C.-27° C. Samples were pulled for Kaiser Test and/or HPLC to check the reaction completion. After the coupling reaction was complete (coupling times vary see table below), the coupling solution was drained and the resin was washed with NMP 4 times (6 vol. each). (NOTE: For Lys-34 and Val-33 the resin was end-capped with acetic anhydride (5.0 equiv.) and DIEA (10 equiv.) in NMP (100 mL) for 3 hours after the coupling.) The resin was then treated twice with 20% piperidine in NMP (6 vol. each treatment) to remove the Fmoc protecting group. (NOTE: For Glu-27 to Ala-24 the resin was treated twice with 20% piperidine 30% DMSO in NMP (6 vol. each treatment) to remove the Fmoc protecting groups.) After the second 20% piperidine/NMP (or piperidine/DMSO/NMP) treatment, the resin was washed nine times with NMP (6 vol. each wash). Then the coupling reaction, 4 NMP washes, deprotection and 9 NMP washes cycle was repeated for remaining amino acids in the fragment (i.e., in the order of Lys(Boc)→Val→Leu→Trp(Boc)→Ala→Ile→Phe→Glu(OtBu)→Lys(Boc)→Ala→Ala→Gln(trt).

All reagents used in this example are listed in following table:

| Material | wt (g)/Eq | HOBT (g/Eq) | DIEA (mL/Eq) | NMP (mL) | HBTU (g/Eq) | NMP (mL) | DCM (mL) | Coupling time (hr) | DeFmoc Time (min) |
|---|---|---|---|---|---|---|---|---|---|
| Lys(Boc) | 6.49/2.0 | 2.14/2.0 | 6.0/5.0 | 59.4 | 5.23/2.0 | 25.6 | 30.0 | 16.0 | — |
| Acetic Anhydride | 3.56/5.0 | — | 12.0/10.0 | 80.0 | — | 20.0 | — | 3.0 | 2 × 30 |
| Val | 4.70/2.0 | 2.13/2.0 | 6.0/5.0 | 59.4 | 5.23/2.0 | 25.6 | 30.0 | 16.0 | — |
| Acetic Anhydride | 3.58/5.0 | — | 12.0/10.0 | 80.0 | — | 20.0 | — | 3.0 | 2 × 30 |
| Leu | 4.16/1.7 | 1.81/1.7 | 4.8/4.0 | 63.0 | 4.44/1.7 | 22.0 | 30.0 | 5.0 | 2 × 30 |
| Trp(Boc) | 6.21/1.7 | 1.80/1.7 | 4.8/4.0 | 63.0 | 4.44/1.7 | 22.0 | 30.0 | 5.0 | 2 × 30 |
| Ala | 3.89/1.7 | 1.81/1.7 | 4.8/4.0 | 63.0 | 4.44/1.7 | 22.0 | 30.0 | 5.0 | 2 × 30 |
| Ile | 4.15/1.7 | 1.83/1.7 | 4.8/4.0 | 63.0 | 4.44/1.7 | 22.0 | 30.0 | 5.0 | 2 × 30 |
| Phe | 4.55/1.7 | 1.82/1.7 | 4.8/4.0 | 63.0 | 4.44/1.7 | 22.0 | 30.0 | 5.0 | 2 × 30 |
| Glu(OtBu) | 5.22/1.7 | 1.81/1.7 | 4.8/4.0 | 63.0 | 4.44/1.7 | 22.0 | 30.0 | 5.0 | 2 × 30 |
| Lys(Boc) | 6.49/2.0 | 2.13/2.0 | 6.0/5.0 | 59.4 | 5.23/2.0 | 25.6 | 30.0 | 5.0 | 2 × 0 |
| Ala | 4.56/2.0 | 2.13/2.0 | 6.0/5.0 | 59.4 | 5.23/2.0 | 25.6 | 30.0 | 16.0 | 2 × 60 |
| Ala | 4.56/2.0 | 2.13/2.0 | 6.0/5.0 | 59.4 | 5.23/2.0 | 25.6 | 30.0 | 16.0 | 2 × 60 |
| Gln(trt) | 8.47/2.0 | 2.14/2.0 | 6.0/5.0 | 59.4 | 5.23/2.0 | 25.6 | 30.0 | 12.0 | |
| Gln(trt) recouple | 7.20/1.7 | 1.83/1.7 | 4.8/4.0 | 63.0 | 4.44/1.7 | 22.0 | 30.0 | 12.0 | |

The built resin from above was washed with NMP 4 times (6 vol. each wash), DCM 7 times (6 vol. each wash), and IPA 3 times (6 vol. each wash) and dried under vacuum at 35° C. Which produced 27.01 g of Fmoc-AA(23-35)-O-2CT resin with a purity of 88.7% AN, a 78.9% yield based on the weight increase of the resin.

Solid Phase Synthesis of GPA fragment 1+2+3

```
Fmoc-His(trt)-Aib-Glu(OtBu)-Gly-Thr(tBu)-Phe-
Thr(tBu)-Ser(OtBu)-Asp(OtBu)-Val-Ser(OtBu)-
Ser(ψMe,Me)-Tyr(tBu)-Leu-Glu(OtBu)-Gly-Gln(trt)-
Ala-Ala-Lys(Boc)-Glu(OtBu)-Phe-Ile-Ala-Trp(Boc)-
Leu-Val-Lys(Boc)-Aib-OH
```

Example 14

Solid phase synthesis of Fmoc-AA(7-35)-OH was carried out starting with 12.0 g of Fmoc-AA(23-35)-O-2-CT resin. The resin was swelled in DCM (120 mL) for 30 min at 25° C. The DCM solvent was drained and the resin was washed and three time with NMP (4.16 vol. each wash).

The resin was then treated four times (30 min each) with 20% piperidine 30% DMSO in NMP (6 vol. each treatment) to remove Fmoc protecting groups. After the 4th 20% piperidine 30% DMSO in NMP treatment, the resin was washed nine times with NMP (4.16 vol. each wash).

To prepare the coupling solution for Fragment 2: Fragment 2 (7.83 g, 1.3 equiv.) and 6-Cl-hydroxybenzotriazole (6-Cl-HOBT; 0.69 g, 1.3 equiv.) were weighed out, dissolved in DMSO (4.16 vol) then combined with an HBTU solution in NMP (10.7 mL of an 174.07 g HBTU/L solution, 1.3 equiv.) and DIEA (1.9 mL) at 15° C. in a flask. The resultant solution was added to resin containing reaction vessel, the flask was rinsed with DCM (11.1 mL) into the reactor, which was stirred at 25° C. Samples were pulled for HPLC to check the reaction completion. After 17 hours agitation, analysis showed a 73.8% conversion for the coupling reaction. Kicker charges of HBTU (1.58 g) and DIEA (0.706 g)

were added and the pot mixture was stirred at 30° C. After another 25.5 hrs agitation, HPLC analysis of a reaction sample indicated that the coupling reaction was 92% complete. The coupling solution was drained and the resin was washed with NMP 4 times (4.166 vol. each wash). The deprotection of the Fmoc group was achieved by treating twice (30 min each) with 20% v/v piperidine and 30% v/v DMSO in NMP (4.16 vol. each treatment). After the second 20% piperidine 30% DMSO in NMP treatment, the resin was washed nine times with NMP (4.16 vol. each wash).

To prepare the coupling solution for Fragment 1: Fragment 1 (3.81 g, 1.3 equiv) and 6-Cl-hydroxybenzotriazole (6-Cl-HOBT; 0.70 g, 1.3 equiv.) were weighed out, dissolved in DMSO (4.16 vol) then combined with an HBTU solution in NMP (10.7 mL of an 174.07 g HBTU/L solution, 1.3 equiv.) and DIEA (1.9 mL) at 15° C. in a flask. The resulting solution was added to the reaction vessel, the flask rinsed into the reactor with DCM (11.1 mL), which was stirred with the resin at 25° C. Samples were pulled for HPLC to check the reaction completion. After 16.5 hours of agitation, analysis showed complete conversion of the coupling reaction. The coupling solution was drained and the resin was washed with NMP 4 times (4.166 vol. each wash).

The built resin from above was washed with DCM 7 times (4.16 vol. each wash) to remove NMP and resin was cooled with the last of DCM to −5° C. The DCM was drained and the cold solution of 2% TFA/DCM (5 vol. at −5° C. to 0° C.) was added and stirred for 15 min at 0° C. The cleavage solution was collected in the flask containing pyridine (1.33 equiv. relative to the total TFA used). Then another 2% TFA/DCM (5 vol. at −5° C. to 0° C.) was added and stirred for 30 min at 0° C. The second cleavage solution was collected in the flask containing pyridine. While vessel warming up to 25° C., the resin was washed with DCM 7 times (5 vol.) and drained into the cleavage solution receiver. Pyridine (0.37 equiv. to the total TFA used) was added the cleavage vessel during $2^{nd}$ DCM wash. The combined DCM solution was concentrated to 10 vol, washed with water (5 vol), and mixed with another 5 volumes of water. The resultant mixture was distilled under reduced pressure to remove DCM (350 torr at 28° C.). The fragment precipitated out from water when the DCM was removed. The fragment was washed with water and dried at 30° C.-35° C. under vacuum. 8.76 g of Fragment 1+2+3 were obtained, a 63.3% yield from H-Aib-O-2CT resin or a 80.2% actual yield from Fmoc-AA(23-35)-0-2CT resin. Analysis showed a purity of 64.6% AN.

Synthesis of Fragment 1+2+3' and Global De-Protection

Example 15a

The GPA Fragment 1+2+3 (4.48 g) was dissolved in DMSO (50 mL). To this solution, H-Arg (2HCl)—NH$_2$ (0.99 g, 4 equiv), HOBt Hydrate (0.61 g, 4 equiv.), HBTU (1.52 g, 4 equiv.), and DIEA (0.87 mL, 5 equiv.) was charged. The reaction was agitated at 25° C. and monitored by HPLC. Overnight reaction completion check indicated that the coupling was done. Piperidine (1 mL) was charged to the reaction mixture. After stirring overnight the Fmoc removal was done. The reaction mixture was then charged to a vessel containing water (150 mL) at 15° C. over 5 minutes. The quenched mixture was warmed up to 40° C. for 0.5 hour, then cooled down to 15° C. The solid was filtered, washed with water (3×30 mL), air dried to provide 4.34 g solid, 98% yield. 4.0 g of this solid was dissolved in DCM (18 mL). To this solution, a solution containing TFA (40 mL), DTT (2.1 g) and water (2.1 mL) was charged. The resulting mixture was stirred at 15° C. for 6 hours before it was cooled to −1° C. Cold MTBE (160 mL, cooled in dry ice) was charged to the cleavage solution over 15 min. The quenched reaction mixture was allowed to warm to 15° C. The solid product was filtered, washed with MTBE (3×30 mL), and air dried overnight at ambient temperature. Obtained was 3.33 g of GPA crude, 100% yield, (23.08% wt/wt) with a purity of 44.9% AN.

Synthesis of Fragment 1+2+3' and Global De-Protection

Example 15b

To a 100 mL flask with magnetic stirrer and thermometer under Argon was added 1.40 g Fragment 1 in 30.0 mL THF. 232 mg HOBt and 917.3 mg HBTU were then added. 436.5 µL DIEA was then added and the reaction was slightly exothermic with the temperature rising about 1° C. 3.00 g Fragment 2+3' in THF was then added. Another 3.00 g Fragment 2+3' in THF was then added. 1.2 mL piperidine was then added and the reaction was slightly exothermic with the temperature rising about 1.5° C., forming a clear yellow solution which was allowed to stir overnight. The solution was then distilled at 42° C./200-100 mbar in a 250 mL flask. 26.25 mL DCM was then added and the solution distilled at 42° C./400-100 mbar. 22.5 mL DCM was then removed over 20 min. In a 500-1000 mL double jacketed flask was added 4.313 g DTT added with 4.313 mL water and 76.9 mL TFA solution. The solution was then cooled to 15° C. and the DCM solution was then added dropwise over 10 min. The reaction was exothermic with the temperature rising to 17° C., white smoke developing, and the solution becoming intensely yellow. 3.75 mL DCM was then added to rinse. The mixture was then allowed to stir at 15° C. for 6 h. Precipitation occurred and the mixture then filtered to give 0.237 g nearly white paste. 360 mL MTBE was then added dropwise over 5 min to the filter cake to form a white suspension, with the temperature rising to 18° C. The suspension was then allowed to stir for 30 min and then filtered. 225 mL MTBE was then added to the paste, again filtered, and dried over 14 h at 42° C./20 mbar to yield a total of 5.787 g product as a white powder. HPLC (Analytic): 51.2% (m/m %), 79.8% (area %) water:: 2.0%; Ethanol: <100%, DCM:<60 ppm; MTBE: 3.2%; THF: <70 ppm; TFA: 8.4%.

GPA Solution Phase Synthesis of GPA Fragment 2+3', Fmoc-AA(11-36)-NH$_2$

H-Thr(tBu)-Phe-Thr(tBu)-Ser(OtBu)-Asp(OtBu)-Val-

Ser(OtBu)-Ser(ψMe,Me)-Tyr(tBu)-Leu-Glu(OtBu)-

Gly-Gln(trt)-Ala-Ala-Lys(Boc)-Glu(OtBu)-Phe-Ile-

Ala-Trp(Boc)-Leu-Val-Lys(Boc)-Aib-Arg-NH$_2$

Example 16

Solid Phase Synthesis of GPA fragment 2+3

```
Fmoc-Thr(tBu)-Phe-Thr(tBu)-Ser(OtBu)-Asp(OtBu)-
Val-Ser(OtBu)-Ser(ψMe,Me)-Tyr(tBu)-Leu-Glu(OtBu)-
Gly-Gln(trt)-Ala-Ala-Lys(Boc)-Glu(OtBu)-Phe-Ile-
Ala-Trp(Boc)-Leu-Val-Lys(Boc)-Aib-OH
```

Solid phase synthesis of Fmoc-AA(7-35)-OH was carried out starting with 12.53 g of Fmoc-AA(23-35)-O-2-CT resin. The resin was swelled in DCM (100 mL) for 30 min at 25° C. The DCM solvent was drained and the resin was washed three times with NMP (4.4 vol. each wash).

The resin was then treated two times (60 min each) with 20% piperidine 30% DMSO in NMP (4.4 vol. each) to remove the Fmoc protecting groups. After the 2nd 20% piperidine 30% DMSO in NMP treatment, the resin was washed nine times with NMP (4.4 vol. each).

To prepare the coupling solution for Fragment 2: Fragment 2 (8.10 g, 1.3 equiv.) and 6-Cl-hydroxybenzotriazole (6-Cl-HOBT; 0.74 g, 1.3 equiv.) were weighed out, dissolved in DMSO (2.66 vol) then combined with diisopropylcarbodiimide (DIC; 0.52 g, 1.3 equiv.) at 15° C. in a flask. The resultant solution was added to the resin containing reaction vessel and the flask was rinsed with DCM (12.7 mL) into the reactor, which was stirred at 30° C. Samples were pulled for HPLC to check for reaction completion. After 25 hours of agitation, analysis showed a 65.6% conversion for the coupling reaction. A kicker charge of DIC (0.55 g) was added and the stirring was continued at 30° C. After another 21 hrs agitation, HPLC analysis of a reaction sample indicated that the coupling reaction was 86% complete. The coupling solution was drained and the resin was washed with NMP 4 times (4.166 vol. each). A re-coupling reaction was then performed by treating the resin with another solution of Fragment 2 (4.04 g, 0.65 equiv.), 6-Cl-HOBT (0.43 g; 0.65 equiv.) in DMSO (33 mL) and DIC (0.26 g. 0.65 equiv.) in DCM (12.7 mL) at 30° C. for 48 hr. HPLC analysis showed 90.8% conversion.

After draining the re-coupling solution, the built resin from above was washed with NMP 4 times (4.4 vol each) and DCM 7 times (4.4 vol. each) to remove the NMP and the resin was cooled with the last DCM wash to −5° C. The DCM was drained and a cold solution of 2% TFA/DCM (4.96 vol. at −5° to 0° C.) was added and stirred for 15 min at 0° C. The cleavage solution was collected in a flask containing pyridine (1.3 equiv. relative to the total TFA used). Then another 2% TFA/DCM (4.96 vol. at −5° C. to 0° C.) was added and stirred for 30 min at 0° C. The second cleavage solution was also collected in the flask containing pyridine. While vessel warming up to 25° C., the resin was washed with DCM 7 times (5 vol. each) and each wash was drained into the cleavage solution receiver. Pyridine (0.25 equiv. to the total TFA used) was added the cleavage vessel during the $2^{nd}$ DCM wash. The combined DCM solution was concentrated to 10 volumes (125 mL), washed with water (4 vol), and mixed with another 10 volumes of water. The resultant mixture was distilled under reduced pressure to remove the DCM (350-75 torr at 28° C.). The fragment precipitated out from water as the DCM was removed. The fragment was washed with water and dried at 30° C.-35° C. under vacuum. 8.19 g of Fragment 2+3 (Fmoc-AA(11-35)-OH) were obtained, a 64.2% yield from H-Aib-O-2CT resin or a 79.5% actual yield from Fmoc-AA(23-35)-O-2CT resin. Analysis showed a purity of 64.7% AN.

Example 17

Solution Phase Synthesis of GPA Fragment 2+3'

```
H-Thr(tBu)-Phe-Thr(tBu)-Ser(OtBu)-Asp(OtBu)-Val-
Ser(OtBu)-Ser(ψMe,Me)-Tyr(tBu)-Leu-Glu(OtBu)-Gly-
Gln(trt)-Ala-Ala-Lys(Boc)-Glu(OtBu)-Phe-Ile-Ala-
Trp(Boc)-Leu-Val-Lys(Boc)-Aib-Arg-NH₂
```

The GPA Fragment 2+3, Fmoc-AA(11-35)-OH, (4.00 g, 1.0 equiv.) and L-Argininamide Dihydrochloride (0.498 g, 2.0 equiv.) were mixed with DMSO (30 mL) and stirred at 23° C.-25° C. for 30 min. To this solution 1-hydroxybenzotriazole hydrate (HOBT, 2.0 equiv.) and HBTU (2.0 equiv.) in DMSO (15 mL) and DIEA (5.5 equiv.) were charged. The reaction was agitated at 25° C. and monitored by HPLC. After 16 hours, 9.1% AN of Fragment 2+3 were still not reacted. Kicker charges of Argininamide Dihydrochloride (0.136 g), HBTU (0.193 g), and DIEA (0.166 g) were added to the reaction solution, which was then agitated for another 15.3 hour. That led a 97.6% completion of the coupling reaction. Then piperidine (7.7 equiv.) was added to the reaction solution. The removal of Fmoc protection group was complete after 90 min at 27° C. The reaction mixture was quenched with water (100 mL) at 15° C.-27° C. The mixture was heated up to 40° C. then cooled to 25° C. The white solid formed was filtered and washed with water (twice, 50 mL each). The filter cake was air dried, then washed, with stirring, with MTBE/heptane (1:1, 100 mL) at 25° C. for 3 hrs. The pot mixture was heated to 40° C. and stirred for 15 minutes. After cooling to 25° C., the product was filtered and washed with MTBE/heptane (1:1, 2×50 mL), and vacuum dried at 35° C.-40° C. A total of 4.22 g, a 107.2% actual yield was obtained with a purity of 63.7% AN.

GPA Solution Phase Synthesis of GPA Fragment 2+3', Fmoc-AA(11-36)-NH₂

Example 18

Fragment 2 (15.0 g, 7.211 mmol) (7.21 mmol total peptide, 1.0 equiv.) is treated with 7.32 mL of a solution containing HOBT (0.1104 g, 0.721 mmol) in 7.23 mL DMF in a reactor and dissolved in 150 mL 2-methyl-tetrahydrofuran (MeTHF) at r.t. The reactor is a 1000 mL double-walled reactor with stopcock at the base, stirrer, PT-100 thermometer, jacketed coil condenser, nitrogen blanket, dropping funnel, and thermostat. The resulting solution is cooled down the to an inner temperature of 0° C. to 5° C. and kept stirring.

In a separate reactor containing 138 mL DMF and 30 mL MeTHF, Fragment 3' (7.355 mmol total peptide, 1.02 equiv.) is added and heated to 35-40° C. and stirred until dissolved. The reactor is a 250 mL double-walled reactor with stopcock at the base, stirrer, PT-100 thermometer, nitrogen blanket, dropping funnel, and thermostat. The resulting solution is cooled down the to an inner temperature of 0° C. to 5° C. and kept stirring.

The solution is then added to the solution containing Fragment 2 in the first reactor at inner temperature of 0° C. to 5° C. and the second reactor rinsed with 30 mL DMF. The cold solution is then treated with 17.45 mL of a solution containing HBTU (3.56 g, 9.37 mmol) and 14 mL DMF over 15 min, and then subsequently with DIEA (1.72 mL, 10.09 mmol) in 30 mL DMF over 10 min whereupon the Fmoc-protected intermediate is formed. The resulting solution is stirred at 0° C. to 5° C. for 30 minutes until reaction complete. The Fmoc-protecting group is then cleaved by adding piperidine (3.06 mL, 31.0 mmol) and heating up to 35±2° C. and kept stirring for approx 1.5 to 2 h until cleavage is complete.

To quench and to carry out the extraction, 375 mL water is added to the tempered solution in the reactor and stirred for approx 5 to 15 minutes (pH approx. 9.9) at an internal temperature of 20° C. to 25° C., then allowed to sit without stirring for at least 60 minutes, and then the phases separated (org. phase=ca. 100 mL). The lower, aqueous phase is then treated a second time with 90 mL Methyl-THF and the mixture stirred for approx 5 to 15 minutes (pH approx. 9.9) at an internal temperature of 25±2° C., and then allowed to sit without stirring for at least 60 minutes, and the two clear phases are then separated (aqueous phase approx. 690 g).

The two organic phases are then combined (approx. 180 to 200 mL) and concentrated under reduced pressure (approx. 120 mbar) and a maximal jacket temperature of 40° C. as long as the residue is still fluid. The residue is then dissolved, at an inner temperature of 20° C. to 40° C. and a maximal jacket temperature of 40° C., in 180 mL Methyl-THF. The solution is then concentrated under reduced pressure (approx. 120 mbar) and a maximal jacket temperature of 40° C. while the residue is still fluid. The residue is then dissolved, at an inner temperature of 20° C. to 40° C. and a maximal jacket temperature of 40° C., in 180 mL Methyl-THF. The solution is then concentrated under reduced pressure (approx. 120 mbar) and a maximal jacket temperature of 40° C. as long as the residue is still well stirable (oil). The residue is then dissolved at an inner temperature of 20° C. to 40° C. and a maximal jacket temperature of 40° C., in 130 mL Methyl-THF then cooled down to 25+2° C. and sampled. The azeotropic distillation, and dilution with Me-THF (see above) is repeated until the sample corresponds.

n-Heptane (750 mL) is then added into a crystallizer (a 1000 mL double-walled reactor with stopcock at the base, stirrer, PT-100 thermometer, jacketed coil condenser, nitrogen blanket, distillation head, dropping funnel, and thermostat) and the product solution in Me-THF prepared above (ca. 200 mL) added at an internal temperature or 25±3° C. over a period of 1 to 2 h. The product precipitates immediately and the transfer line rinsed with max. 10 mL Methyl-THF. The mixture is then stirred for at least 1 h at 25±3° C. The product is then filtered using a suction filter and washed with n-Heptane (150 ml) and the product dried under vacuum (<20 mbar) at an external temperature of no more than 35° C. for 12 h. The procedure gives approx. 30 to 32 g of slightly off-white product. Yield: approx. 75% from fragment 2 or 77% from fragment 3'.

Examples 19-29 Pertain the Coupling Reaction Scheme as Described in Scheme 2 and the Fragments 1, 2, 3, and 3' are as Defined Therein Solid Phase Synthesis of GPA Alternative Fragment 3, Fmoc-AA(28-35)-OH Fmoc-Phe-Ile-Ala-Trp(Boc)-Leu-Val-Lys(Boc)-Aib-OH Example 19

Solid Phase Synthesis of GPA Alternative Fragment 3, Fmoc-AA(28-35-O-2CT Resin

Fmoc-Phe-Ile-Ala-Trp(Boc)-Leu-Val-Lys(Boc)-Aib-2-CT resin

Solid phase synthesis of Fmoc-AA(28-35)-O-2CT resin was carried out on a Roche Peptide Synthesizer. Fmoc-Aib-2-CT resin (15.02 g) with a loading of 0.36 mmol/g was charged to the reaction vessel and swelled in DCM (150 mL) for 30 min at 25° C. The DCM solvent was drained and the resin was washed three times with DMF (90 mL each wash).

All Fmoc deprotections of the resin were carried out by treating the resin twice with 20% (v/v) piperidine in DMF (90 mL each treatment) to remove Fmoc protecting groups. After the second piperidine/DMF treatment, the resin was washed nine times with DMF (100 mL each wash).

To prepare the activated ester solution, the amino acid and 1-hydroxybenzotriazole hydrate (HOBT.H$_2$O) were weighed, dissolved in DMF in a flask then sequentially combined with a stock HBTU solution (0.503 mmoles/mL) in DMF and DIEA at 0° C.-5° C. The resultant solution was added to reaction vessel, the preparation flask was rinsed with DCM into reactor, which was then stirred with the resin for 4-16 hours at 25° C. A sample was taken for Kaiser Test or HPLC analysis to confirm reaction completion. After the coupling reaction was complete, the coupling solution was drained and the resin was washed with NMP 4 times (100 mL each wash). If the coupling was incomplete after 16 hours the resin was end-capped by reaction with acetic anhydride and DIEA in DMF and DCM for 3 hours. The sequence of removing the Fmoc group and coupling the next amino acid was repeated for remaining amino acids in the fragment (i.e., in the order of Lys(Boc)→Val→Leu→Trp(Boc)→Ala→Ile→Phe.

All reagent amounts used in this example are listed in the following table:

| Material | A.A wt (g)/Eq | HOBT H$_2$O (g)/Eq | DMF (mL) | DIEA (mL)/ Eq | HBTU Sol'n (mL)/ Eq | DCM (mL) | Coupling time (min) |
|---|---|---|---|---|---|---|---|
| Fmoc-Lys(Boc)-OH | 5.97/2.35 | 1.94/2.35 | 36.8 | 4.7/5.0 | 25.2/2.35 | 21.4 | 960 |
| Acetic Anhydride | 2.81/5.0 | — | 82.8 | 9.4/10.0 | — | — | 180 |
| Fmoc-Val-OH | 4.31/2.35 | 1.97/2.35 | 36.8 | 4.7/5.0 | 25.2/2.35 | 21.4 | 960 |

-continued

| Material | A.A wt (g)/Eq | HOBT H$_2$O (g)/Eq | DMF (mL) | DIEA (mL)/Eq | HBTU Sol'n (mL)/Eq | DCM (mL) | Coupling time (min) |
|---|---|---|---|---|---|---|---|
| Acetic Anhydride | 2.79/5.0 | — | 82.8 | 9.4/10.0 | — | — | 180 |
| Fmoc-Leu-OH | 3.26/1.7 | 1.42/1.7 | — | 3.8/4.0 | 18.2/1.7 | 21.4 | 240 |
| Fmoc-Trp(Boc)-OH | 4.83/1.7 | 1.42/1.7 | — | 3.8/4.0 | 18.2/1.7 | 21.4 | 240 |
| Fmoc-Ala-OH | 3.05/1.7 | 1.42/1.7 | — | 3.8/4.0 | 18.2/1.7 | 21.4 | 240 |
| Fmoc-Ile-OH | 3.27/1.7 | 1.43/1.7 | — | 3.8/4.0 | 18.2/1.7 | 21.4 | 240 |
| Fmoc-Phe-OH | 3.57/1.7 | 1.43/1.7 | — | 3.8/4.0 | 18.2/1.7 | 21.4 | 240 |

After completion of the solid phase synthesis the resin was washed with DMF (4×100 mL), DCM (7×100 mL), and iso-propanol (3×100 mL). The built resin is vacuum dried (19.35 g) and held for cleavage.

Example 20

Cleavage of the GPA Intermediate Fragment Fmoc-AA(28-35)-OH from Built Resin

The built resin, 19.0 g, from Example 19 was swelled in DCM (150 mL) for 30 min at 25° C. Then the mixture was cooled to −5° C. The DCM was drained and the resin was treated with the cold solution of 2% TFA/DCM (2×7.5 vol) twice with stirring for 30 min at 0° C. The cleavage solutions were collected in a flask containing pyridine (1.3 equiv. relative to the total TFA used). While the vessel was warming up to 25° C., the resin was washed with DCM 6 times (150 mL) and drained into a receiving vessel. The DCM solutions were combined, concentrated, and mixed with water (150 mL). The resultant mixture was again distilled under reduced pressure to remove the remaining DCM (350-50 torr at 25° C.). The fragment precipitated from the water as the DCM was removed. The fragment was filtered, washed with and dried at 30° C.-35° C. under vacuum. A 92.7% yield of GPA alternative fragment 3 (Fmoc-AA(28-35)-OH) was obtained with a purity of 95.2% AN.

Example 21

Solid Phase Synthesis of the GPA Alternative Fragment 3 Fmoc-AA(28-35)-O-2CT Resin Fmoc-Phe-Ile-Ala-Trp(Boc)-Leu-Val-Lys(Boc)-Aib-O-2CT resin Solid phase synthesis of Fmoc-AA(28-35)-O-2CT resin was carried out on a Roche Peptide Synthesizer. H-Aib-2-O-CT resin (25.01 g) with loading of 0.59 mmol/g (batch # B006010051) was charged to the reaction vessel and swelled in DCM (250 mL) for 30 min at 25° C. The DCM solvent was drained and the resin was washed three times with NMP (150 mL each wash).

All Fmoc deprotections of the resin were carried out by treating the resin twice with 20% (v/v) piperidine in NMP (140 mL each treatment) to remove the Fmoc protecting groups. After the second piperidine/NMP treatment, the resin was washed nine times with NMP (140 mL each wash).

To prepare the activated ester solution, the Fmoc amino acid and HOBT.H$_2$O were weighed, dissolved in NMP then sequentially combined with an HBTU solution (0.46 mmole/mL) in NMP and DIEA at 0° C.-5° C. The resultant solution was added to the reaction vessel, the flask was rinsed with NMP into the reactor, which was stirred with the resin for 4-16 hours at 25° C. A sample was taken for Kaiser Test or HPLC analysis to check for reaction completion. After the coupling reaction was complete, the coupling solution was drained and the resin was washed with NMP 4 times (140 mL each wash). If the coupling was still incomplete at 16 h the resin was washed (4×140 mL NMP), end-capped by reaction with acetic anhydride and DIEA for 2 h, then washed with NMP 4 times (140 mL each wash). Then the sequence of removal of the Fmoc group, washing, coupling reaction, and washing was repeated for remaining amino acids in the fragment (i.e., in the order of Lys(Boc)→Val→Leu→Trp(Boc)→Ala→Ile→Phe).

All reagent amounts used in this example are listed in following table:

| Material | A.A wt (g/Eq) | HOBT H$_2$O (g/Eq) | NMP (mL) | DCM (mL) | DIEA (mL/Eq) | HBTU Sol'n (mL/Eq) | Coupling time (min) |
|---|---|---|---|---|---|---|---|
| Fmoc-Lys(Boc)-OH | 13.86/2.0 | 0.24/0.1 | 88 | — | 6.4/2.5 | 64.2/2.0 | 720 |
| Acetic Anhydride | 4.62/3.0 | — | — | 112.5 | 12.8/5.0 | — | 120 |
| Fmoc-Val-OH | 4.31/2.35 | 0.26/0.1 | 88 | — | 6.4/2.5 | 64.2/2.0 | 720 |

| Material | A.A wt (g/ Eq) | HOBT H$_2$O (g/Eq) | NMP (mL) | DCM (mL) | DIEA (mL/Eq) | HBTU Sol'n (mL/ Eq) | Coupling time (min) |
|---|---|---|---|---|---|---|---|
| Acetic Anhydride | 4.60/3.0 | — | — | 112.5 | 12.8/5.0 | — | 120 |
| Fmoc-Leu-OH | 8.85/1.7 | 0.22/0.085 | 96 | — | 5.5/2.13 | 54.6/1.7 | 240 |
| Fmoc-Trp(Boc)-OH | 13.22/1.7 | 0.21/0.085 | 96 | — | 5.5/2.13 | 54.6/1.7 | 240 |
| Fmoc-Ala-OH | 8.28/1.7 | 0.21/0.085 | 96 | — | 5.5/2.13 | 54.6/1.7 | 240 |
| Fmoc-Ile-OH | 8.85/1.7 | 0.19/0.085 | 96 | — | 5.5/2.13 | 54.6/1.7 | 240 |
| Fmoc-Phe-OH | 9.73/1.7 | 0.21/0.085 | 96 | — | 5.5/2.13 | 54.6/1.7 | 240 |

After completion of the solid phase synthesis the resin was washed with NMP (4×150 mL) and DCM (7×150 mL).

Cleavage of the GPA Alternative Fragment 3 (Fmoc-AA (28-35)-OH) from the Built Resin:

The built resin from Example 21 was cooled in DCM (150 mL) over 30 min to −5° C. Then the DCM was drained and the resin was treated twice with a cold solution of 2% TFA/DCM (2×250 mL) with stirring for 30 min at 0° C. The cleavage solutions were collected in a flask containing pyridine (1.3 equiv. relative to the total TFA). While the vessel was warming up to 25° C., the resin was washed with DCM 6 times (150 mL each wash) and the washes combined with the cleavage solution. The combined DCM solution was concentrated under vacuum, and mixed with water (150 mL). The resultant mixture was distilled under reduced pressure to remove DCM (350-50 torr at 25° C.). The fragment precipitated out from the water as the DCM was removed. The fragment was filtered, washed with and dried at 30° C.-35° C. under vacuum. A 96.9% yield of GPA alternative fragment 3 (Fmoc-AA(28-35)-OH) was obtained with a purity of 96.1% AN.

Solid Phase Synthesis of the GPA Alternative Fragment 1+2, Fmoc-AA(7-27)-OH

```
Fmoc-His(trt)-Aib-Glu(OtBu)-Gly-Thr(tBu)-Phe-

Thr(tBu)-Ser(tBu)-Asp(OtBu)-Val-Ser(tBu)-

Ser(ψMe,Me pro)-Tyr(tBu)-Leu-Glu(OtBu)-

Gly-Gln(trt)-Ala-Ala-Lys(Boc)-Glu(OtBu)-OH
```

Example 22

Solid Phase Synthesis of the GPA Alternative Fragment 1+2, Fmoc-AA(7-27)-O-2CT Resin

```
Fmoc-His(trt)-Aib-Glu(OtBu)-Gly-Thr(tBu)-Phe-

Thr(tBu)-Ser(tBu)-Asp(OtBu)-Val-Ser(tBu)-

Ser(ψMe,Me pro)-Tyr(tBu)-Leu-Glu(OtBu)-Gly-

Gln(trt)-Ala-Ala-Lys(Boc)-Glu(OtBu)-O-2CT resin
```

Solid phase synthesis of Fmoc-AA(7-27)-O-2CT resin was carried out on a Roche Peptide Synthesizer. Fmoc-Glu (OtBu)-O-2CT resin (10.04 g) with loading factor of 0.41 mmol/g (393-150) was charged to a reaction vessel and swelled with DCM (150 mL) for 30 min at 25° C. The DCM solvent was drained and the resin was washed three times with DMF (90 mL each wash).

Then the swelled and washed Fmoc-Glu(OtBu)-O-2CT resin was deprotected with piperidine in DMF. All Fmoc deprotections of the resin were carried out by treating the resin twice with 20% piperidine in DMF (80 mL) for 30 min to remove the Fmoc protecting groups. After the second piperidine/DMF treatment (30 min), the resin was washed nine times with DMF (90 mL each wash).

To prepare the coupling solution, 2.0 equiv. amino acid and 2.0 equiv. HOBT.H$_2$O were weighed, dissolved in DMF in a flask then sequentially combined with 2.0 equiv. HBTU solution (0.503 mmol/mL) in DMF and 4.5 equiv. DIEA at 0° C.-5° C. The resultant solution was added to the reaction vessel, the flask was rinsed with DCM into the reactor, which was stirred with resin for 4 hours at 25° C. A sample was taken for Kaiser Test or HPLC analysis to check the reaction completion. After the coupling reaction was complete, the coupling solution was drained and the resin was washed with NMP 4 times (90 mL each wash). Then the removal of the Fmoc group and coupling reaction cycle was repeated for the remaining amino acids in the fragment (i.e., in the order of Lys(Boc)→Ala→Ala→Gln(trt)→Gly→Glu(OtBu)→Leu→Tyr(tBu)→Ser(tBu)-Ser(ψMe,Me)→Val→Asp (OtBu)→Ser(tBu)→Thr(tBu)→Phe→Thr(tBu)→Frag.1.)

For the final coupling 1.6 equiv. of GPA Fragment 1 (Fmoc-AA(7-10)-OH, Fmoc-His(trt)-Aib-Glu(OtBu)-Gly-OH), 1.5 equiv. HOBT.H$_2$O, 1.5 equiv. HBTU, and 3.38 equiv. DIEA were used. This reaction mixture was stirred for 16 hours to reach completion.

All reagent amounts used in this example are listed in following table:

| Material | A.A wt (g/Eq) | HOBT H$_2$O (g/Eq) | DMF (mL) | DIEA (mL/Eq) | HBTU Sol'n (mL/Eq) | DCM (mL) | Coupling time (min) |
|---|---|---|---|---|---|---|---|
| Fmoc-Lys(Boc)-OH | 3.86/2.0 | 1.27/2.0 | 33.5 | 3.2/4.5 | 16.3/2.0 | 17.8 | 240 |
| Fmoc-Ala-OH•H2O | 2.71/2.0 | 1.27/2.0 | 33.5 | 3.2/4.5 | 16.3/2.0 | 17.8 | 240 |
| Fmoc-Ala-OH•H2O | 2.71/2.0 | 1.28/2.0 | 33.5 | 3.2/4.5 | 16.3/2.0 | 17.8 | 240 |
| Fmoc-Gln(trt)-OH | 5.08/2.0 | 1.29/2.0 | 33.5 | 3.2/4.5 | 16.3/2.0 | 17.8 | 240 |
| Fmoc-Gly-OH | 2.44/2.0 | 1.27/2.0 | 33.5 | 3.2/4.5 | 16.3/2.0 | 17.8 | 240 |
| Fmoc-Glu(OtBu)-OH | 3.52/2.0 | 1.28/2.0 | 33.5 | 3.2/4.5 | 16.3/2.0 | 17.8 | 240 |
| Fmoc-Leu-OH | 2.91/2.0 | 1.28/2.0 | 33.5 | 3.2/4.5 | 16.3/2.0 | 17.8 | 240 |
| Fmoc-Tyr(tBu)-OH | 3.78/2.0 | 1.28/2.0 | 33.5 | 3.2/4.5 | 16.3/2.0 | 17.8 | 240 |
| Fmoc-Ser(tBu)-Ser(ψMe,Me)-OH | 4.19/2.0 | 1.28/2.0 | 33.5 | 3.2/4.5 | 16.3/2.0 | 17.8 | 240 |
| Fmoc-Val-OH | 2.82/2.0 | 1.28/2.0 | 33.5 | 3.2/4.5 | 16.3/2.0 | 17.8 | 240 |
| Fmoc-Asp(OtBu)-OH | 3.38/2.0 | 1.28/2.0 | 33.5 | 3.2/4.5 | 16.3/2.0 | 17.8 | 240 |
| Fmoc-Ser(tBu)-OH | 3.16/2.0 | 1.28/2.0 | 33.5 | 3.2/4.5 | 16.3/2.0 | 17.8 | 240 |
| Fmoc-Thr(tBu)-OH | 3.26/2.0 | 1.29/2.0 | 33.5 | 3.2/4.5 | 16.3/2.0 | 17.8 | 240 |
| Fmoc-Phe-OH | 3.21/2.0 | 1.29/2.0 | 33.5 | 3.2/4.5 | 16.3/2.0 | 17.8 | 240 |
| Fmoc-Thr(tBu)-OH | 3.27/2.0 | 1.28/2.0 | 33.5 | 3.2/4.5 | 16.3/2.0 | 17.8 | 240 |
| Frag. 1 (Fmoc-His(trt)-Aib-Glu(OtBu)-Gly-OH) | 6.23/1.6 | 0.96/1.5 | 23.9 | 2.4/3.38 | 12.2/1.5 | 13.4 | 960 |

After completion of the solid phase synthesis the resin was washed with DMF (6×90 mL), DCM (7×90 mL), and isopropanol (3×90 mL). Then the built resin was vacuum dried and held for cleavage.

Example 23

Cleavage of the GPA Intermediate Fragment 1+2 Fmoc-AA(7-27)-OH from Built Resin

The built resin, (18.24 g), from Example 22 was swelled in DCM (200 mL) for 30 min at 25° C. Then the mixture was cooled to −5° C. The DCM was drained and the resin was treated with a cold solution of 1% TFA/DCM (3×100 mL) three times by stirring for 30 min at 0° C. The cleavage solution was collected in a flask containing pyridine (1.4 equiv. relative to the total TFA). While the vessel was warming up to 25° C., the resin was washed with DCM 3 times (100 mL). All DCM solutions were combined, concentrated, and mixed with water (100 mL). The resultant mixture was distilled under reduced pressure to remove DCM (350-50 torr at 25° C.). The fragment precipitated out from the water as the DCM was removed. The fragment was filtered, washed with water and dried at 30° C.-35° C. under vacuum. A 67.6% yield of GPA alternative fragment 1+2 (Fmoc-AA(7-27)-OH) was obtained with a purity of 85.3% AN.

Example 24

Solid Phase Synthesis of the GPA Alternative fragment 1+2, Fmoc-AA(7-27)-O-2CT Resin

```
Fmoc-His(trt)-Aib-Glu(OtBu)-Gly-Thr(tBu)-Phe-
Thr(tBu)-Ser(tBu)-Asp(OtBu)-Val-Ser(tBu)Ser(ψMe,Me
pro)-Tyr(tBu)-Leu-Glu(OtBu)-Gly-Gln(trt)-Ala-Ala-
Lys(Boc)-Glu(OtBu)-O-2CT
```

Solid phase synthesis of Fmoc-AA(7-27)-O-2CT resin was repeated on Roche Peptide Synthesizer at the scale of 20.0 g of Fmoc-Glu(OtBu)-O-2CT resin with loading factor at 0.50 mmol/g (393-53). The resin was swelled in DCM (200 mL) for 30 min at 25° C. The DCM solvent was drained and the resin was washed three times with DMF (120 mL each wash).

Then the swelled and washed Fmoc-Glu(OtBu)-O-2CT resin was deprotected with piperidine in DMF. All deprotections of resin were carried out by treating the resin twice with 20% piperidine in DMF (120 mL each treatment) for 30 min to remove the Fmoc protecting groups. After the second piperidine/DMF treatment (30 min), the resin was washed nine times with DMF (120 mL each wash).

To prepare the coupling solution, 2.0 equiv. amino acid (or GPA Fragment 1) and 2.0 equiv. HOBT.H₂O were weighed, dissolved in DMF then sequentially combined with 2.0 equiv. HBTU solution (0.503 mmoles/mL) in DMF and 4.5 equiv. of DIEA at 0° C.-5° C. The resultant solution was added to reaction vessel, flask was then rinsed with DCM into the reactor, which was stirred with the resin for 4 hours at 25° C. A sample was taken for Kaiser Test or HPLC analysis to check the reaction completion. After the coupling reaction was complete, the coupling solution was drained and the resin was washed with NMP 4 times (180 mL each wash). Then the de-protection of the Fmoc group and coupling reaction cycle was repeated for remaining amino acids in the fragment (i.e., in the order of Lys(Boc)→Ala Ala→Gln(trt)→Gly→Glu (OtBu)→Leu→Tyr(tBu)→Ser((tBu)Ser(ψMe,Me)→ Val→Asp(OtBu)→Ser(tBu)→Thr(tBu)→Phe→ Thr(tBu)→Frag. 1.)

Only 1.5 equiv. of Fragment 1 (Fmoc-AA(7-10)-OH), HOBT.H₂O, HBTU, and 3.38 equiv. of DIEA were used for the final coupling. This reaction mixture was stirred for 16 hours.

All reagent amounts used in this example are listed in following table:

After completion of the solid phase synthesis the resin was washed with DMF (4×120 mL) and DCM (8×120 mL). The mixture was cooled to −5° C. during the last DCM wash in preparation for cleavage.

Cleavage of the GPA Intermediate Fragment Fmoc-AA(7-27)-OH from Built Resin:

After the reactor temperature of the built resin in DCM from above reached −5° C., the DCM was drained and the resin was treated with a cold solution of 1% TFA/DCM (3×200 mL) three times with stirring for 30 min at 0° C. The cleavage solution was collected in a flask containing pyridine (1.4 equiv. based on the total TFA used). While the vessel was warming to 25° C., the resin was washed with DCM 5 times (200 mL each). All DCM solutions were combined, concentrated, and mixed with water (200 mL) and isopropanol (80 mL). The resultant mixture was distilled under reduced pressure to remove DCM (350-50 torr at 25° C.). The fragment precipitated out as the DCM was removed. The fragment was filtered, washed with and dried at 30° C.-35° C. under vacuum. A 77.7% yield of GPA alternative fragment 1+2 (Fmoc-AA(7-27)-OH) was obtained with a purity of 86.4% AN.

| Material | A.A wt (g/Eq) | HOBT H₂O (g/Eq) | DMF (mL) | DIEA (mL/Eq) | HBTU Sol'n (mL/Eq) | DCM (mL) | Coupling time (min) |
|---|---|---|---|---|---|---|---|
| Fmoc-Lys(Boc)-OH | 9.38/2.0 | 3.07/2.0 | 60.0 | 7.8/4.5 | 36.9/2.0 | 32.8 | 240 |
| Fmoc-Ala-OH | 6.60/2.0 | 3.09/2.0 | 60.0 | 7.8/4.5 | 36.9/2.0 | 32.8 | 240 |
| Fmoc-Ala-OH | 6.63/2.0 | 3.07/2.0 | 60.0 | 7.8/4.5 | 36.9/2.0 | 32.8 | 240 |
| Fmoc-Gln(trt)-OH | 12.22/2.0 | 3.07/2.0 | 60.0 | 7.8/4.5 | 36.9/2.0 | 32.8 | 240 |
| Fmoc-Gly-OH | 5.97/2.0 | 3.05/2.0 | 60.0 | 7.8/4.5 | 36.9/2.0 | 32.8 | 240 |
| Fmoc-Glu(OtBu)-OH | 8.53/2.0 | 3.05/2.0 | 60.0 | 7.8/4.5 | 36.9/2.0 | 32.8 | 240 |
| Fmoc-Leu-OH | 7.06/2.0 | 3.06/2.0 | 60.0 | 7.8/4.5 | 36.9/2.0 | 32.8 | 240 |
| Fmoc-Tyr(tBu)-OH | 9.22/2.0 | 3.06/2.0 | 60.0 | 7.8/4.5 | 36.9/2.0 | 32.8 | 240 |
| Fmoc-Ser(tBu)Ser(ψMe,Me)-OH | 10.21/2.0 | 3.07/2.0 | 60.0 | 7.8/4.5 | 36.9/2.0 | 32.8 | 240 |
| Fmoc-Val-OH | 6.79/2.0 | 3.08/2.0 | 60.0 | 7.8/4.5 | 36.9/2.0 | 32.8 | 240 |
| Fmoc-Asp(OtBu)-OH | 8.23/2.0 | 3.07/2.0 | 60.0 | 7.8/4.5 | 36.9/2.0 | 32.8 | 240 |
| Fmoc-Ser(tBu)-OH | 7.69/2.0 | 3.06/2.0 | 60.0 | 7.8/4.5 | 36.9/2.0 | 32.8 | 240 |
| Fmoc-Thr(tBu)-OH | 7.97/2.0 | 3.06/2.0 | 60.0 | 7.8/4.5 | 36.9/2.0 | 32.8 | 240 |
| Fmoc-Phe-OH | 7.76/2.0 | 3.06/2.0 | 60.0 | 7.8/4.5 | 36.9/2.0 | 32.8 | 240 |
| Fmoc-Thr(tBu)-OH | 7.97/2.0 | 3.06/2.0 | 60.0 | 7.8/4.5 | 36.9/2.0 | 32.8 | 240 |
| Frag. 1 (Fmoc-His(trt)-Aib-Glu(OtBu)-Gly-OH) | 14.21/1.5 | 2.30/1.5 | 45.0 | 5.9/4.0 | 27.6/1.7 | 25.3 | 960 |

The Solution Phase Synthesis of the GPA Alternative Fragment 3', H-AA(28-36)-NH$_2$ H-Phe-Ile-Ala-Trp(Boc)-Leu-Val-Lys(Boc)-Aib-Arg-NH$_2$

Example 25

The alternative fragment 3 (Fmoc-AA(28-35)-OH, 6.11 g, 4.42 mmoles Example 20 and argininamide dihydrochloride (H-Arg (2HCl)—NH2, 2.18 g, 8.84 mmoles, 2 equiv.) were dissolved in DMF (42 mL). To this solution, a solution of HOBt.H$_2$O (0.67 g, 1 equiv) and HBTU (3.38 g, 2 equiv) in DMF (42 mL), and DIEA (3.44 mL, 4 equiv) were sequentially charged along with 15 mL of DMF. The reaction mixture was agitated at 25° C. and monitored by HPLC. The reaction was complete after stirring for 21 hours. Then piperidine (2.26 g, 6 equiv) was added to the reaction mixture. The Fmoc removal was incomplete after stirring at 35° C. for one hour. The additional piperidine (2.33 g, 6.2 equiv) was added and stirring continued another 1.75 hours. The reaction mixture was quenched with water (240 mL) to form a white solid. Pyridine hydrochloride (8.33 g, 16.3 equiv) was charged to the precipitated reaction mixture to neutralize the piperidine. The white solid was filtered, washed with water (400 mL) and partially dried overnight. The wet filter cake was re-slurried with 100 mL MTBE/n-heptane (1:1=vol:vol), filtered, washed with MTBE/n-heptane (1:1=vol:vol; 2×25 mL), and vacuum dried to give GPA alternative Fragment 3' H-AA(28-36)-NH$_2$ (6.22 g, yield 106.9%). HPLC analysis showed a purity of 87% AN.

Example 26

The alternative fragment 3 (Fmoc-AA(28-35)-OH, 6.12 g, 4.42 mmoles Example 21 and argininamide dihydrochloride (H-Arg (2HCl)—NH2, 2.19 g, 8.84 mmoles, 2 equiv.) were dissolved in DMF (42 mL). To this solution, a solution of HOBt.H$_2$O (0.67 g, 1 equiv) and HBTU (3.38 g, 2 equiv) in DMF (42 mL), and DIEA (3.44 mL, 4 equiv) were sequentially charged along with 15 mL of DMF. The reaction was agitated at 25° C. and monitored by HPLC. The reaction was done overnight (16.3 hours). Then piperidine (4.52 g, 12 equiv) was added to the reaction mixture. The Fmoc removal was completed after stirring at 25° C. for 35 min. The reaction mixture was quenched with water (200 mL). DCM (180 mL) was charged to extract the precipitated product. The bottom DCM layer was washed with water twice (2×100 mL) and concentrated to a volume of 50 mL. This concentrated DCM solution was fed portion-wise to heptane 150 mL to precipitate the product. The DCM was distilled under vacuum. MTBE 120 mL was charged to the precipitation mixture. The white solid formed was filtered, washed with MTBE/n-heptane (1:1=vol:vol; 2×50 mL), and vacuum dried to give the GPA alternative Fragment 3' H-AA(28-36)-NH$_2$ (6.54 g, weight yield 112.4%). HPLC analysis showed a purity of 92.1% AN.

The Solution Phase Synthesis of GPA Crude

Example 27

The GPA Fragment 1+2 (Fmoc-AA(7-27)-OH) (0.383 g) from Example 23 and Fragment 3' (H-AA(28-36)-NH2) (0.203 g) from Example 24 was dissolved in a solution of DMSO (2 mL) and NMP (4 mL) and stirred for 1 hour. To this solution, HOBt hydrate (0.040 g) and HBTU (0.092 g) were charged. Then, DIEA (0.080 mL) was charged to the reaction mixture. The reaction was agitated at ambient temperature and monitored by HPLC. After stirring for 68 h reaction completion check indicated that the reaction was done. Piperidine (0.1 mL) was charged to the reaction mixture. After 16 h of stirring, the Fmoc removal was done. The reaction mixture then was quenched by charging into water (40 mL). After 30 min stirring, the solid was isolated by filtering, washing with water (20 mL) and drying overnight. The isolated solid then was charged to a solution containing TFA (4 mL), DCM (1.5 mL), dithiothreitol (DTT), (0.2 g) and water (0.2 mL) at ambient temperature. After 6 hours of agitation, the reaction mixture was quenched by charging cold (−20° C.) MTBE (40 mL). The quenched reaction mixture was stirred for 30 min. The solid product was filtered, washed with MTBE (2×10 mL), and dried overnight at ambient temperature. A 0.42 g of GPA crude (28.2% wt/wt) was obtained with a purity of 49.5% AN (D-Glu-27 isomer, 7.9%).

Example 28

The GPA Fragment 1+2 (Fmoc-AA(7-27)-OH) (0.382 g) from batch Example 23 and Fragment 3' (H-AA(28-36)-NH2) (0.202 g) from Example 25 was dissolved in the solution of DMSO (2 mL) and NMP (4 mL) and stirred for 0.5 hour. To this solution, HOBt hydrate (0.041 g) and DEPBT (0.085 g) were charged. Then, DIEA (0.080 mL) was charged to the reaction mixture. The reaction was stirred at ambient temperature and monitored by HPLC. Overnight reaction completion check indicated that the reaction was complete. Piperidine (0.1 mL) was charged to the reaction mixture. After 68 hours of stirring, the Fmoc removal was done. The reaction mixture then was quenched by charging into water (40 mL). After 15 min stirring, the solid was isolated by filtering, washing with water (20 mL) and drying overnight. The isolated solid then was charged to a solution containing TFA (4 mL), DCM (1.5 mL), DTT (0.2 g) and water (0.2 mL) at ambient temperature. After 6 hours agitation, the reaction mixture was quenched by charging cold (−20° C.) MTBE (40 mL). The quenched reaction mixture was stirred for 30 min. The solid product was filtered, washed with MTBE (2×10 mL), and dried overnight at ambient temperature. A weight of 0.43 g of GPA crude (31.4% wt/wt) was obtained with a purity of 51.3% AN (D-Glu-27 epimer, 4.5%).

Example 29

Step A. Coupling Reaction of Fragment 1+2 with Fragment 3' in THF with HOBt, HBTU and DIEA Into a 100 mL 4-necked flask with 37.5 mL THF at 22° C.-27° C. internal temperature Fragment 1+2 (6.20 g, 2.32 mmol) was added in three portions within 10 min. Into a 20 mL round bottomed flask HOBt hydrate (309 mg, 1.98 mmol) and HBTU (1223 mg, 3.16 mmol) were added. 10.0 mL THF was added and the reaction mixture was stirred at 22° C.-27° C. internal temperature for 10 min. This coupling reagent suspension was added to the peptide solution, the flask was rinsed with 3.0 mL THF, and the reaction mixture was stirred for 10 min. DIEA (0.582 mL, 3.31 mmol) was then added and stirred for 10 min. Within 1 h, Fragment 3' (6.10 g, 2.72 mmol) was added in 3 portions. The fragment leftovers were rinsed with 10.0 mL THF. The reaction mixture was stirred intensively at 25° C.-27° C. internal temperature for 24 h.

Step B. FMOC-Group Removal with Piperidine

Piperidine (1.60 mL, 16.0 mmol) was then added and the reaction mixture was stirred intensively for 6 h at 25° C.-27° C. internal temperature. The reaction mixture was then transferred to a 250 mL round bottomed flask and solvent removed in vacuo at 42° C. bath temperature/200-100 mbar.

Step C. Solvent Exchange with Methylene Chloride

The residue was then dissolved in 35.0 mL methylene chloride which was then removed in vacuo at 42° C. bath temperature/400-100 mbar. The residue was then dissolved in 30.0 mL methylene chloride.

Step D. Global Deprotection with TFA/DTT/Water

Into a 1000 mL double jacketed flask (5.75 g, 37.1 mmol) DTT, 5.75 mL $H_2O$ and (102.5 mL, 1220 mmol) TFA were added and the solution was cooled to 15° C. internal temperature. The peptide solution was then added within 10-15 min and the addition funnel was rinsed with 5.0 mL methylene chloride. The intensive yellow reaction solution was stirred at 14° C.-16° C. internal temperature for 10.5 h.

Step E. Precipitation of the Peptide Upon Addition of MTBE

The reaction mixture was then cooled to 0° C. internal temperature, and 480 mL MTBE (pre-cooled to 0-5° C.) was added continuously within 10 min and the internal temperature allowed to rise to 22° C. The suspension was then stirred for 2 h at 16° C.-18° C. internal temperature and then filtered. The still moist filter cake was washed 3 times with 300 mL MTBE (3×100 mL). Then the flask was rinsed, the filter cake slurried and filtered. The filter cake was then sucked dry after the last washing and the residue was dried over night at 38° C.-42° C./20-30 mbar. (chem. yield: 58-65%, assay: 39-43%).

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A peptide of the amino acid sequence SEQ ID NO: 15)

$$Z\text{-TFTSDVX}^{17\text{-}18}\text{YLEGQAAKEFIAWLVKAibR-NH}_2$$

wherein

Z is selected from H- and Fmoc-;
$X^{17\text{-}18}$ is a dipeptide residue of a pseudoproline; and one or more residues of said sequence optionally include side chain protection.

2. The peptide of claim 1, wherein the dipeptide residue of a pseudoproline is a Ser-Ser residue of a pseudoproline.

* * * * *

```
SEQUENCE LISTING

<160> NUMBER OF SEQ ID NOS: 32

<210> SEQ ID NO 1
<211> LENGTH: 37
<212> TYPE: PRT
<213> ORGANISM: Homo sapiens

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 30
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15
```

```
Gln Ala Ala Lys Glu Phe Ile Ala Trp Leu Val Lys Gly Arg
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..()
<223> OTHER INFORMATION: Xaa is Aib
<220> FEATURE:
<221> NAME/KEY: MISC_FEATURE
<222> LOCATION: (29)..()
<223> OTHER INFORMATION: Xaa is Aib

<400> SEQUENCE: 4

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 5
<211> LENGTH: 13
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (13)..(13)
<223> OTHER INFORMATION: Xaa is an achiral amino acid
<220> FEATURE:
<221> NAME/KEY: MISC_FEATURE
<222> LOCATION: (13)..(13)
<223> OTHER INFORMATION: is substituted by B' being a solid phase resin
      or -OH

<400> SEQUENCE: 5

Gln Ala Ala Lys Glu Phe Ile Ala Trp Leu Val Lys Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (13)..(13)
<223> OTHER INFORMATION: Xaa is an achiral amino acid
<220> FEATURE:
<221> NAME/KEY: MISC_FEATURE
<222> LOCATION: (14)..(14)
<223> OTHER INFORMATION: amidated Arginine (Argininamide)

<400> SEQUENCE: 6

Gln Ala Ala Lys Glu Phe Ile Ala Trp Leu Val Lys Xaa Arg
1               5                   10
```

```
<210> SEQ ID NO 7
<211> LENGTH: 12
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (7)..(7)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (8)..(8)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (12)..(12)
<223> OTHER INFORMATION: is substituted by B' being a solid phase resin
      or -OH

<400> SEQUENCE: 7

Thr Phe Thr Ser Asp Val Xaa Xaa Tyr Leu Glu Gly
1               5                   10

<210> SEQ ID NO 8
<211> LENGTH: 26
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (7)..(7)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (8)..(8)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (25)..(25)
<223> OTHER INFORMATION: Xaa is an achiral amino acid
<220> FEATURE:
<221> NAME/KEY: MISC_FEATURE
<222> LOCATION: (26)..(26)
<223> OTHER INFORMATION: amidated Arginine (Argininamide)

<400> SEQUENCE: 8

Thr Phe Thr Ser Asp Val Xaa Xaa Tyr Leu Glu Gly Gln Ala Ala Lys
1               5                   10                  15

Glu Phe Ile Ala Trp Leu Val Lys Xaa Arg
            20                  25

<210> SEQ ID NO 9
<211> LENGTH: 4
<212> TYPE: PRT
<213> ORGANISM: Artificial Sequence
<220> FEATURE:
<223> OTHER INFORMATION: Chemically synthesized peptide
```

```
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (2)..(2)
<223> OTHER INFORMATION: Xaa is an achiral amino acid
<220> FEATURE:
<221> NAME/KEY: MISC_FEATURE
<222> LOCATION: (4)..(4)
<223> OTHER INFORMATION: Xaa is an achiral amino acid
<220> FEATURE:
<221> NAME/KEY: MISC_FEATURE
<222> LOCATION: (4)..(4)
<223> OTHER INFORMATION: is substituted by B' being a solid phase resin
      or -OH

<400> SEQUENCE: 9

His Xaa Glu Xaa
1

<210> SEQ ID NO 10
<211> LENGTH: 30
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (2)..(2)
<223> OTHER INFORMATION: Xaa is an achiral amino acid
<220> FEATURE:
<221> NAME/KEY: MISC_FEATURE
<222> LOCATION: (4)..(4)
<223> OTHER INFORMATION: Xaa is an achiral amino acid
<220> FEATURE:
<221> NAME/KEY: MISC_FEATURE
<222> LOCATION: (11)..(11)
<223> OTHER INFORMATION: Xaa is an amino acid of a pseudoproline
      dipeptide (residues 11-12)
<220> FEATURE:
<221> NAME/KEY: MISC_FEATURE
<222> LOCATION: (12)..(12)
<223> OTHER INFORMATION: Xaa is an amino acid of a pseudoproline
      dipeptide (residues 11-12)
<220> FEATURE:
<221> NAME/KEY: MISC_FEATURE
<222> LOCATION: (29)..(29)
<223> OTHER INFORMATION: Xaa is an achiral amino acid
<220> FEATURE:
<221> NAME/KEY: MISC_FEATURE
<222> LOCATION: (30)..(30)
<223> OTHER INFORMATION: amidated arginine (Argininamide)

<400> SEQUENCE: 10

His Xaa Glu Xaa Thr Phe Thr Ser Asp Val Xaa Xaa Tyr Leu Glu Gly
1               5                   10                  15

Gln Ala Ala Lys Glu Phe Ile Ala Trp Leu Val Lys Xaa Arg
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
```

```
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (2)..(2)
<223> OTHER INFORMATION: Xaa is an achiral amino acid
<220> FEATURE:
<221> NAME/KEY: MISC_FEATURE
<222> LOCATION: (4)..(4)
<223> OTHER INFORMATION: Xaa is an achiral amino acid
<220> FEATURE:
<221> NAME/KEY: MISC_FEATURE
<222> LOCATION: (29)..(29)
<223> OTHER INFORMATION: Xaa is an achiral amino acid
<220> FEATURE:
<221> NAME/KEY: MISC_FEATURE
<222> LOCATION: (30)..(30)
<223> OTHER INFORMATION: amidated arginine (argininamide)

<400> SEQUENCE: 11

His Xaa Glu Xaa Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (29)..(29)
<223> OTHER INFORMATION: Xaa is Aib
<220> FEATURE:
<221> NAME/KEY: MISC_FEATURE
<222> LOCATION: (30)..(30)
<223> OTHER INFORMATION: amidated Arginine (Argininamide)

<400> SEQUENCE: 12

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 13
<211> LENGTH: 25
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (7)..(7)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (8)..(8)
<223> OTHER INFORMATION: Xaa is an amino acid of a pseudoproline
      dipeptide (residues 7-8)
<220> FEATURE:
<221> NAME/KEY: MISC_FEATURE
```

```
<222> LOCATION: (22)..(22)
<223> OTHER INFORMATION: Xaa is an achiral amino acid
<220> FEATURE:
<221> NAME/KEY: MISC_FEATURE
<222> LOCATION: (25)..(25)
<223> OTHER INFORMATION: Xaa is an achiral amino acid
<220> FEATURE:
<221> NAME/KEY: MISC_FEATURE
<222> LOCATION: (25)..(25)
<223> OTHER INFORMATION: is substituted by B' being a solid phase resin
      or -OH

<400> SEQUENCE: 13

Thr Phe Thr Ser Asp Val Xaa Xaa Tyr Leu Glu Gly Gln Ala Ala Lys
1               5                   10                  15

Glu Phe Ile Ala Trp Leu Val Lys Xaa
            20                  25

<210> SEQ ID NO 14
<211> LENGTH: 25
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (7)..(7)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (8)..(8)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (25)..(25)
<223> OTHER INFORMATION: Xaa is Aib
<220> FEATURE:
<221> NAME/KEY: MISC_FEATURE
<222> LOCATION: (25)..(25)
<223> OTHER INFORMATION: is substituted by B' being a solid phase resin
      or -OH

<400> SEQUENCE: 14

Thr Phe Thr Ser Asp Val Xaa Xaa Tyr Leu Glu Gly Gln Ala Ala Lys
1               5                   10                  15

Glu Phe Ile Ala Trp Leu Val Lys Xaa
            20                  25

<210> SEQ ID NO 15
<211> LENGTH: 26
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (7)..(7)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (8)..(8)
```

```
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (25)..(25)
<223> OTHER INFORMATION: Xaa is Aib
<220> FEATURE:
<221> NAME/KEY: MISC_FEATURE
<222> LOCATION: (26)..(26)
<223> OTHER INFORMATION: amidated arginine (Argininamide)

<400> SEQUENCE: 15

Thr Phe Thr Ser Asp Val Xaa Xaa Tyr Leu Glu Gly Gln Ala Ala Lys
1               5                   10                  15

Glu Phe Ile Ala Trp Leu Val Lys Xaa Arg
            20                  25

<210> SEQ ID NO 16
<211> LENGTH: 8
<212> TYPE: PRT
<213> ORGANISM: Artificial sequence
<220> FEATURE:
<223> OTHER INFORMATION: Chemically synthesized petide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (8)..(8)
<223> OTHER INFORMATION: Xaa is an achiral amino acid
<220> FEATURE:
<221> NAME/KEY: MISC_FEATURE
<222> LOCATION: (8)..(8)
<223> OTHER INFORMATION: is substituted by B' being a solid phase resin
      or -OH

<400> SEQUENCE: 16

Phe Ile Ala Trp Leu Val Lys Xaa
1               5

<210> SEQ ID NO 17
<211> LENGTH: 9
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (8)..(8)
<223> OTHER INFORMATION: Xaa is an achiral amino acid
<220> FEATURE:
<221> NAME/KEY: MISC_FEATURE
<222> LOCATION: (9)..(9)
<223> OTHER INFORMATION: amidated arginine (argininamide)

<400> SEQUENCE: 17

Phe Ile Ala Trp Leu Val Lys Xaa Arg
1               5

<210> SEQ ID NO 18
<211> LENGTH: 21
<212> TYPE: PRT
<213> ORGANISM: Artificial sequence
<220> FEATURE:
<223> OTHER INFORMATION: Chemically synthesized peptide
<220> FEATURE:
```

```
<221> NAME/KEY: MISC_FEATURE
<222> LOCATION: (1)..(1)
<223> OTHER INFORMATION: is substituted by Z being an N-terminal
      protecting group or hydrogen
<220> FEATURE:
<221> NAME/KEY: MISC_FEATURE
<222> LOCATION: (2)..(2)
<223> OTHER INFORMATION: Xaa is an achiral amino acid
<220> FEATURE:
<221> NAME/KEY: MISC_FEATURE
<222> LOCATION: (4)..(4)
<223> OTHER INFORMATION: Xaa is an achiral amino acid
<220> FEATURE:
<221> NAME/KEY: MISC_FEATURE
<222> LOCATION: (11)..(11)
<223> OTHER INFORMATION: Xaa is an amino acid of a pseudoproline
      dipeptide (residues 11-12)
<220> FEATURE:
<221> NAME/KEY: MISC_FEATURE
<222> LOCATION: (12)..(12)
<223> OTHER INFORMATION: Xaa is an amino acid of a pseudoproline
      dipeptide (residues 11-12)
<220> FEATURE:
<221> NAME/KEY: MISC_FEATURE
<222> LOCATION: (21)..(21)
<223> OTHER INFORMATION: is substituted by B' being a solid phase resin
      or -OH

<400> SEQUENCE: 18

His Xaa Glu Xaa Thr Phe Thr Ser Asp Val Xaa Xaa Tyr Leu Glu Gly
1               5                   10                  15

Gln Ala Ala Lys Glu
            20

<210> SEQ ID NO 19
<211> LENGTH: 30
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Xaa is an achiral amino acid
<220> FEATURE:
<221> NAME/KEY: MISC_FEATURE
<222> LOCATION: (4)..(4)
<223> OTHER INFORMATION: Xaa is an achiral amino acid
<220> FEATURE:
<221> NAME/KEY: MISC_FEATURE
<222> LOCATION: (29)..(29)
<223> OTHER INFORMATION: Xaa is an achiral amino acid
<220> FEATURE:
<221> NAME/KEY: MISC_FEATURE
<222> LOCATION: (30)..(30)
<223> OTHER INFORMATION: amidated arginine (argininamide)

<400> SEQUENCE: 19

His Xaa Glu Xaa Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 20
<211> LENGTH: 4
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Xaa is an achiral amino acid
<220> FEATURE:
```

```
<221> NAME/KEY: MISC_FEATURE
<222> LOCATION: (4)..(4)
<223> OTHER INFORMATION: Xaa is an achiral amino acid

<400> SEQUENCE: 20

His Xaa Glu Xaa
1

<210> SEQ ID NO 21
<211> LENGTH: 4
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Xaa is Aib

<400> SEQUENCE: 21

His Xaa Glu Gly
1

<210> SEQ ID NO 22
<211> LENGTH: 12
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (7)..(7)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (8)..(8)
<223> OTHER INFORMATION: Xaa is an amino acid of a pseudoproline
      dipeptide (residues 7-8)

<400> SEQUENCE: 22

Thr Phe Thr Ser Asp Val Xaa Xaa Tyr Leu Glu Gly
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (13)..(13)
<223> OTHER INFORMATION: Xaa is an achiral amino acid

<400> SEQUENCE: 23

Gln Ala Ala Lys Glu Phe Ile Ala Trp Leu Val Lys Xaa
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Chemicallly synthesized peptide
<220> FEATURE:
<221> NAME/KEY: MISC_FEATURE
<222> LOCATION: (13)..(13)
<223> OTHER INFORMATION: Xaa is Aib

<400> SEQUENCE: 24
```

```
Gln Ala Ala Lys Glu Phe Ile Ala Trp Leu Val Lys Xaa
1               5                   10
```

```
<210> SEQ ID NO 25
<211> LENGTH: 26
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (7)..(7)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (8)..(8)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (25)..(25)
<223> OTHER INFORMATION: Xaa is an achiral amino acid
<220> FEATURE:
<221> NAME/KEY: MISC_FEATURE
<222> LOCATION: (26)..(26)
<223> OTHER INFORMATION: amidated arginine (argininamide)

<400> SEQUENCE: 25

Thr Phe Thr Ser Asp Val Xaa Xaa Tyr Leu Glu Gly Gln Ala Ala Lys
1               5                   10                  15

Glu Phe Ile Ala Trp Leu Val Lys Xaa Arg
            20                  25
```

```
<210> SEQ ID NO 26
<211> LENGTH: 30
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Xaa is an achiral amino acid
<220> FEATURE:
<221> NAME/KEY: MISC_FEATURE
<222> LOCATION: (4)..(4)
<223> OTHER INFORMATION: Xaa is an achiral amino acid
<220> FEATURE:
<221> NAME/KEY: MISC_FEATURE
<222> LOCATION: (11)..(11)
<223> OTHER INFORMATION: Xaa is an amino acid of a pseudoproline
      dipeptide (residues 11-12)
<220> FEATURE:
<221> NAME/KEY: MISC_FEATURE
<222> LOCATION: (12)..(12)
<223> OTHER INFORMATION: Xaa is an amino acid of a pseudoproline
      dipeptide (residues 11-12)
<220> FEATURE:
<221> NAME/KEY: MISC_FEATURE
<222> LOCATION: (29)..(29)
<223> OTHER INFORMATION: Xaa is an achiral amino acid
<220> FEATURE:
<221> NAME/KEY: MISC_FEATURE
<222> LOCATION: (30)..(30)
<223> OTHER INFORMATION: amidated arginine (argininamide)

<400> SEQUENCE: 26

His Xaa Glu Xaa Thr Phe Thr Ser Asp Val Xaa Xaa Tyr Leu Glu Gly
1               5                   10                  15

Gln Ala Ala Lys Glu Phe Ile Ala Trp Leu Val Lys Xaa Arg
            20                  25                  30
```

```
<210> SEQ ID NO 27
<211> LENGTH: 21
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Xaa is an achiral amino acid
<220> FEATURE:
<221> NAME/KEY: MISC_FEATURE
<222> LOCATION: (4)..(4)
<223> OTHER INFORMATION: Xaa is an achiral amino acid
<220> FEATURE:
<221> NAME/KEY: MISC_FEATURE
<222> LOCATION: (11)..(11)
<223> OTHER INFORMATION: Xaa is an amino acid of a pseudoproline
      dipeptide (residues 11-12)
<220> FEATURE:
<221> NAME/KEY: MISC_FEATURE
<222> LOCATION: (12)..(12)
<223> OTHER INFORMATION: Xaa is an amino acid of a pseudoproline
      dipeptide (residues 11-12)

<400> SEQUENCE: 27

His Xaa Glu Xaa Thr Phe Thr Ser Asp Val Xaa Xaa Tyr Leu Glu Gly
1               5                   10                  15

Gln Ala Ala Lys Glu
            20

<210> SEQ ID NO 28
<211> LENGTH: 21
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (11)..(11)
<223> OTHER INFORMATION: Xaa is an amino acid of a pseudoproline
      dipeptide (residues 11-12)
<220> FEATURE:
<221> NAME/KEY: MISC_FEATURE
<222> LOCATION: (12)..(12)
<223> OTHER INFORMATION: Xaa is an amino acid of a pseudoproline
      dipeptide (residues 11-12)

<400> SEQUENCE: 28

His Xaa Glu Gly Thr Phe Thr Ser Asp Val Xaa Xaa Tyr Leu Glu Gly
1               5                   10                  15

Gln Ala Ala Lys Glu
            20

<210> SEQ ID NO 29
<211> LENGTH: 17
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (7)..(7)
<223> OTHER INFORMATION: Xaa is an amino acid of a pseudoproline
      dipeptide (residues 7-8)
<220> FEATURE:
<221> NAME/KEY: MISC_FEATURE
<222> LOCATION: (8)..(8)
<223> OTHER INFORMATION: Xaa is an amino acid of a pseudoproline
      dipeptide (residues 7-8)
```

```
<400> SEQUENCE: 29

Thr Phe Thr Ser Asp Val Xaa Xaa Tyr Leu Glu Gly Gln Ala Ala Lys
1               5                   10                  15

Glu

<210> SEQ ID NO 30
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (8)..(8)
<223> OTHER INFORMATION: Xaa is an achiral amino acid

<400> SEQUENCE: 30

Phe Ile Ala Trp Leu Val Lys Xaa
1               5

<210> SEQ ID NO 31
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (8)..(8)
<223> OTHER INFORMATION: Xaa is Aib

<400> SEQUENCE: 31

Phe Ile Ala Trp Leu Val Lys Xaa
1               5

<210> SEQ ID NO 32
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (8)..(8)
<223> OTHER INFORMATION: Xaa is an achiral amino acid
<220> FEATURE:
<221> NAME/KEY: MISC_FEATURE
<222> LOCATION: (9)..(9)
<223> OTHER INFORMATION: amidated arginine (argininamide

<400> SEQUENCE: 32

Phe Ile Ala Trp Leu Val Lys Xaa Arg
1               5
```